US009352069B2

(12) United States Patent
Dickinson et al.

(10) Patent No.: US 9,352,069 B2
(45) Date of Patent: May 31, 2016

(54) GERMANIUM-BASED GLASS POLYALKENOATE CEMENT

(71) Applicant: DALHOUSIE UNIVERSITY, Halifax (CA)

(72) Inventors: Victoria Dickinson, Halifax (CA); Daniel Boyd, Halifax (CA); Brett Dickey, Halifax (CA); Sharon Kehoe, Halifax (CA)

(73) Assignee: DALHOUSIE UNIVERSITY, Halifax (CA)

( * ) Notice: Subject to any disclaimer, the term of this patent is extended or adjusted under 35 U.S.C. 154(b) by 0 days.

(21) Appl. No.: 14/397,965

(22) PCT Filed: May 3, 2013

(86) PCT No.: PCT/IB2013/001166
§ 371 (c)(1),
(2) Date: Oct. 30, 2014

(87) PCT Pub. No.: WO2013/164696
PCT Pub. Date: Nov. 7, 2013

(65) Prior Publication Data
US 2015/0126640 A1    May 7, 2015

Related U.S. Application Data

(60) Provisional application No. 61/643,077, filed on May 4, 2012, provisional application No. 61/642,444, filed on May 3, 2012.

(51) Int. Cl.
| | |
|---|---|
| *C08L 33/08* | (2006.01) |
| *A61L 24/00* | (2006.01) |
| *A61B 17/58* | (2006.01) |
| *C03C 3/253* | (2006.01) |
| *C03C 12/00* | (2006.01) |
| *A61L 24/02* | (2006.01) |
| *A61L 24/12* | (2006.01) |
| *A61L 24/04* | (2006.01) |
| *C03C 3/062* | (2006.01) |
| *C03C 3/078* | (2006.01) |
| *C03C 4/00* | (2006.01) |

(52) U.S. Cl.
CPC ............ *A61L 24/0089* (2013.01); *A61B 17/58* (2013.01); *A61L 24/02* (2013.01); *A61L 24/046* (2013.01); *A61L 24/12* (2013.01); *C03C 3/062* (2013.01); *C03C 3/078* (2013.01); *C03C 3/253* (2013.01); *C03C 4/0007* (2013.01); *C03C 12/00* (2013.01); *A61L 2400/06* (2013.01); *A61L 2430/02* (2013.01); *C03C 2204/00* (2013.01)

(58) Field of Classification Search
None
See application file for complete search history.

(56) References Cited

U.S. PATENT DOCUMENTS

| 4,495,298 | A  | * | 1/1985  | Yamagishi ............... C03C 3/062 |
|---|---|---|---|---|
| | | | | 359/654 |
| 7,981,972 | B2 | * | 7/2011  | Towler .................. A61L 24/0089 |
| | | | | 522/150 |
| 2002/0041436 | A1 | | 4/2002 | Kondo et al. |
| 2004/0079258 | A1 | | 4/2004 | Hoescheler et al. |
| 2005/0242725 | A1 | | 11/2005 | Hasegawa et al. |
| 2008/0182920 | A1 | | 7/2008 | Towler et al. |
| 2010/0035214 | A1 | * | 2/2010  | Reynaud ................. A61C 13/30 |
| | | | | 433/220 |
| 2011/0009511 | A1 | | 1/2011 | Hill et al. |
| 2015/0126640 | A1 | * | 5/2015 | Dickinson ............... A61B 17/58 |
| | | | | 523/116 |

FOREIGN PATENT DOCUMENTS

WO    WO2008090533 A2    7/2008

OTHER PUBLICATIONS

Boyd, D., et al., Zinc-based glass polyalkenoate cements with improved setting times and mechanical properties. Acta biomaterialia, 2008. 4(2):p. 425-31.
Rajmohan, N., P. Frugier, and S. Gin, Composition effects on synthetic glass alteration mechanisms: Part 1. Experiments. Chemical Geology, 2010. 279: p. 106-119.
Angeli, F., et al., Influence of zirconium on the structure of pristine and leached soda-lime borosilicate glasses: Towards a quantitative approach by 170 MQMAS NMR. Journal of Non-Crystalline Solids, 2008. 354(31): p. 3713-3722.
Neve, A.D., V. Piddock, and E.C. Combe, The effect of glass heat treatment on the properties of a novel polyalkenoate cement. Clinical Materials, 1993. 12(2): p. 113-115.
Boyd, D., et al., Comparison of an experimental bone cement with surgical Simplex P, Sineplex and Cortoss. Journal of material science. Materials in medicine, 2008. 19(4): p. 1745-52.
Clarkin, O., D. Boyd, and M.R. Towler, Strontium-based glass polyalkenoate cements for luting applications in the skeleton. Journal of biomaterials applications, 2010. 24(6): p. 483-502.
Clarkin, O.M., Boyd, and M.R. Towler, Comparison of failure mechanisms for cements used in skeletal luting applications. Journal of materials science. Materials in medicine, 2009. 20(8): p. 1585-94.
ISO9917, Dentistry—Water-based cements, 2007.
Williams, J-A., R.W. Billington, and G.J. Pearson, The effect of the disc support system on biaxial tensile strength of a glass ionomer cement. Dental Materials, 2002. 18(5): p. 376-379.

(Continued)

*Primary Examiner* — Peter A Salamon
(74) *Attorney, Agent, or Firm* — David A. Nauman; Borden Ladner Gervais LLP

(57) ABSTRACT

Disclosed herein are compositions and methods for making germanium-based glass polyalkenoate cements. Also disclosed are methods for their use as bone cements for bone augmentation procedures.

30 Claims, 45 Drawing Sheets

(56) References Cited

OTHER PUBLICATIONS

Higgs, W.A.J., et al., A simple method of determining the modulus of orthopedic bone cement. Journal of biomedical materials research, 2001. 58(2): p. 188-195.
ISO6872, Dentistry—Ceramic materials, 2008.
Tsigkou o. Jones JR, Polak JM, Stevens MM. Differentiation of fetal osteoblasts and formation of mineralized bone nodules by 45S5 Bioglass (R) conditioned medium in the absence of osteogenic supplements. Biomaterials. 2009, 30:3542-50.
International Search Report and Written Opinion dated Sep. 6, 2013 on corresponding International Application No. PCT/IB2013/001166.
International Preliminary Report on Patentability Chapter I for corresponding International Application No. PCT/IB2013/001166, issued Nov. 4, 2014.
Extended European Search Report and Opinion issued on corresponding European Patent Application No. 137851374 dated Feb. 9, 2016.

* cited by examiner

GERMANIUM-BASED GLASS POLYALKENOATE CEMENT

CROSS-REFERENCE TO RELATED APPLICATIONS

This application is a U.S. National Entry of PCT Patent Application No. PCT/IB2013/001166, filed May 3, 2013, which claims the benefit of priority of U.S. Provisional Application No. 61/642,444, filed May 3, 2012, and U.S. Provisional Application No. 61/643,077, filed May 4, 2012, which are incorporated herein by reference.

FIELD

The disclosure relates to germanium-based glass polyalkenoate cements useful as bone cements, including for vertebroplasty, fracture stabilizations, and repair of skeletal implants.

BACKGROUND

Glass polyalkenoate cements (GPC) (also referred to as glass ionomer cements) are frequently used in dentistry as restorative and luting agents. GPCs are theoretically attractive for other clinical uses, such as orthopedics, because they set with a negligible exotherm. This is important because materials which generate heat upon setting can lead to thermal necrosis of adjacent healthy tissue. Additionally, GPCs bond with hydroxyapatite (present in both teeth and bones) and thus the set GPC is less likely to loosen over time. Finally, GPCs can be modified to release therapeutically beneficial ions over time. However, conventional GPCs are based on aluminosilicate glasses which are contraindicated in orthopedics as release of $Al^{3+}$ in vivo leads to significant adverse effects for the patient. Fatal aluminum-induced encephalopathy, impaired osteoblastic function and hindered bone mineralization have been reported when using GPCs that include aluminum. GPCs free of aluminum have been attempted but those materials were not suitable as they set too quickly and did not provide sufficient handling time prior to setting to be able to deploy them. Some materials that did have longer handling times before setting had lower mechanical strength and thus were unsuitable for that reason.

What is needed are new GPCs for orthopedic applications that do not release aluminum ions but whose characteristics allow sufficient time to handle the material prior to setting and deliver sufficient mechanical strength.

SUMMARY

Novel germanium GPCs provide working times between 5 and 10 minutes, setting times between 14 and 36 minutes, and compression strengths in excess of 30 MPa for the first 30 days. These handling characteristics and mechanical properties make these GPCs clinically viable as injectable bone cements and are achieved without the use of aluminum.

In a first aspect, disclosed herein is a composition comprising a glass powder, which comprises 0.1-0.75 mole fraction $GeO_2$; 0.11-0.53 mole fraction ZnO; and 0.01-0.2 mole fraction CaO.

In some embodiments, the composition further comprise 0.025-0.12 mole fraction SrO. In some embodiments, the compositions further comprise 0.005-0.08 mole fraction each of $ZrO_2$ and $Na_2O$. In some embodiments, the compositions comprise 0.1-0.75 mole fraction $GeO_2$ and 0.005-0.04 mole fraction each of $ZrO_2$ and $Na_2O$. In some embodiments, the compositions further comprise 0.02-0.48 mole fraction $SiO_2$. In some embodiments, the compositions comprise 0.1-0.75, 0.1-0.6, 0.2-0.5 or 0.35-0.50 mole fraction $GeO_2$. In some embodiments, the compositions comprise about 0.36 mole fraction ZnO. In some embodiments, the compositions comprise 0.2-0.48, 0.02-0.25 or 0.02-0.2 mole fraction $SiO_2$. In some embodiments, the compositions comprise about 0.04 mole fraction SrO. In some embodiments, the compositions comprise 0.01-0.35, 0.02-0.16, 0.02-0.12, 0.05-0.15, or 0.07-0.13 mole fraction CaO.

In some embodiments, the compositions comprise 0.005-0.06, 0.01-0.055 or 0.02-0.04 mole fraction each of $ZrO_2$ and $Na_2O$. In some embodiments, the compositions comprise no more than 0.01 mole fraction aluminosilicates. In some embodiments, the compositions are substantially free of aluminosilicates. In some embodiments, the compositions comprise an acid degradable powder. In some embodiments, the compositions are radio opaque. In some embodiments, the compositions comprise a polyalkenoate cement having a glass phase made from the glass powder.

In a second aspect, disclosed herein is a method of preparing a bone cement comprising mixing the glass powder described above with an aqueous solution of a about 40%-60% by weight polyalkenoic acid in a ratio of about 2:1 to 1:1, and wherein the polyalkenoic acid has a weight average molecular weight ($M_W$) of about 1,150 to 1,500,000; 1,150 to 383,000; 1,150 to 114,000; or 1,150 to 22,700.

In some embodiments of the method, the aqueous solution of polyalkenoic acid is 50% by weight. In some embodiments of the method, the polyalkenoic acid has a weight average molecular weight ($M_W$) of about 12,700. In some embodiments of the method, the polyalkenoic acid comprises polyacrylic acid.

In a third aspect, disclosed herein is a composition comprising a glass powder, which comprises: 0 mole fraction $SiO_2$, 0.480 mole fraction $GeO_2$, 0.001 combined mole fraction $ZrO_2/Na_2O$, and 0.119 mole fraction CaO; or 0.012 mole fraction $SiO_2$, 0.468 mole fraction $GeO_2$, 0.017 combined mole fraction $ZrO_2/Na_2O$, and 0.103 mole fraction CaO; or 0.057 mole fraction $SiO_2$, 0.381 mole fraction $GeO_2$, 0.047 combined mole fraction $ZrO_2/Na_2O$, and 0.115 mole fraction CaO; or 0.130 mole fraction $SiO_2$, 0.350 mole fraction $GeO_2$, 0.029 combined mole fraction $ZrO_2/Na_2O$, and 0.091 mole fraction CaO; or 0.021 mole fraction $SiO_2$, 0.459 mole fraction $GeO_2$, 0.019 combined mole fraction $ZrO_2/Na_2O$, and 0.101 mole fraction CaO; or 0.215 mole fraction $SiO_2$, 0.215 mole fraction $GeO_2$, 0.050 combined mole fraction $ZrO_2/Na_2O$, and 0.120 mole fraction CaO; or 0 mole fraction $SiO_2$, 0.480 mole fraction $GeO_2$, 0.100 combined mole fraction $ZrO_2/Na_2O$, and 0.020 mole fraction CaO; and further comprises zinc and strontium components.

In some embodiments of the composition, the zinc and strontium components comprise 0.36 mole fraction ZnO and 0.04 mole fraction SrO. In some embodiments of the composition, the combined mole fraction $ZrO_2/Na_2O$ is made from equal mole fractions of $ZrO_2$ and $Na_2O$.

In a fourth aspect, disclosed herein is a composition comprising a glass powder, which comprises 0.318 mole fraction $SiO_2$, 0.162 mole fraction $GeO_2$, 0.032 combined mole fraction $ZrO_2/Na_2O$, and 0.088 mole fraction CaO; and further comprising zinc and strontium components.

In some embodiments of the composition, the zinc and strontium components comprise 0.36 mole fraction ZnO and 0.04 mole fraction SrO. In some embodiments of the composition, the combined mole fraction $ZrO_2/Na_2O$ is made from equal mole fractions of $ZrO_2$ and $Na_2O$.

In a fifth aspect, disclosed herein is a kit for use in preparing a bone cement comprising the glass powders described and instructions for preparing the bone cement.

In some embodiments, the kit further comprises a polyalkenoic acid. In some embodiments of the kit, the polyalkenoic acid is in the form of a powder. In some embodiments of the kit, the polyalkenoic acid is in the form of an aqueous solution of a about 40%-60% by weight polyalkenoic acid in a ratio of about 2:1 to 1:1, and wherein the polyalkenoic acid has a weight average molecular weight ($M_W$) of about 1,150 to 1,500,000; 1,150 to 383,000; 1,150 to 114,000; or 1,150 to 22,700. In some embodiments of the kit, the aqueous solution of polyalkenoic acid is 50% by weight. In some embodiments of the kit, the polyalkenoic acid has a weight average molecular weight ($M_W$) of about 12,700. In some embodiments of the kit, the polyalkenoic acid comprises polyacrylic acid.

In a sixth aspect, disclosed herein is a method of augmenting bone, comprising the steps of: (a) preparing a bone cement comprising mixing the any of the glass powders described above with an aqueous solution of a about 40%-60% by weight polyalkenoic acid in a ratio of about 2:1 to 1:1, and wherein the polyalkenoic acid has a weight average molecular weight ($M_W$) of about 1,150 to 1,500,000; 1,150 to 383,000; 1,150 to 114,000; or 1,150 to 22,700; (b) injecting said cement into a subject in need thereof, thereby augmenting the bone.

In some embodiments of this method, the aqueous solution of polyalkenoic acid is 50% by weight. In some embodiments of this method, the polyalkenoic acid has a weight average molecular weight ($M_W$) of about 12,700. In some embodiments of this method, the polyalkenoic acid comprises polyacrylic acid. In some embodiments of this method, the bone augmenting is performed on a bone fracture. In some embodiments of this method, the injecting is through percutaneous cannulae into a fractured vertebrae. In some embodiments, the method further comprises the step of inflating a balloon tamp inserted into the bone fracture prior to injection of said bone cement.

DETAILED DESCRIPTION

Figure 1:
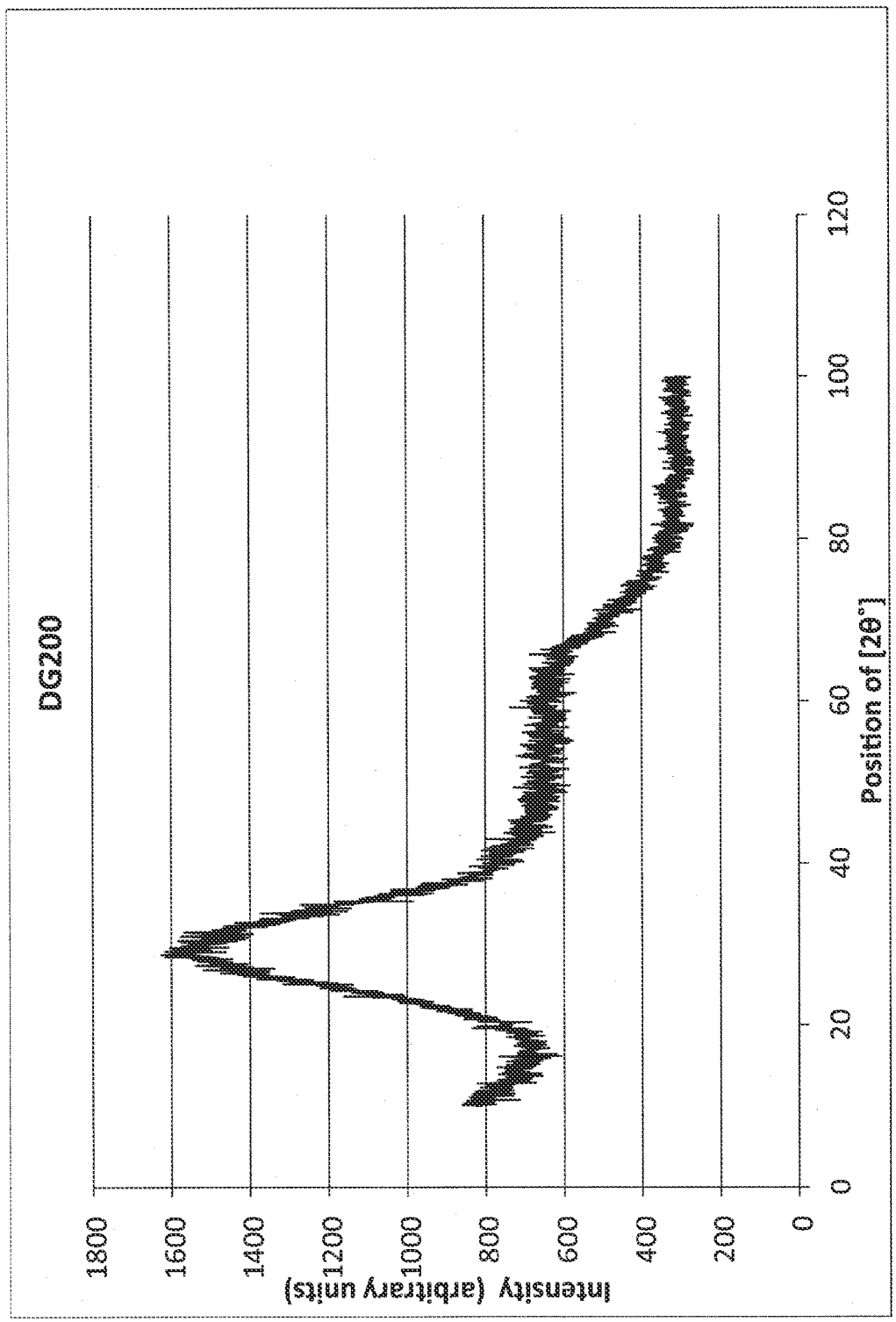
FIG. 1 is an XRD plot of sample DG200.
Figure 2:
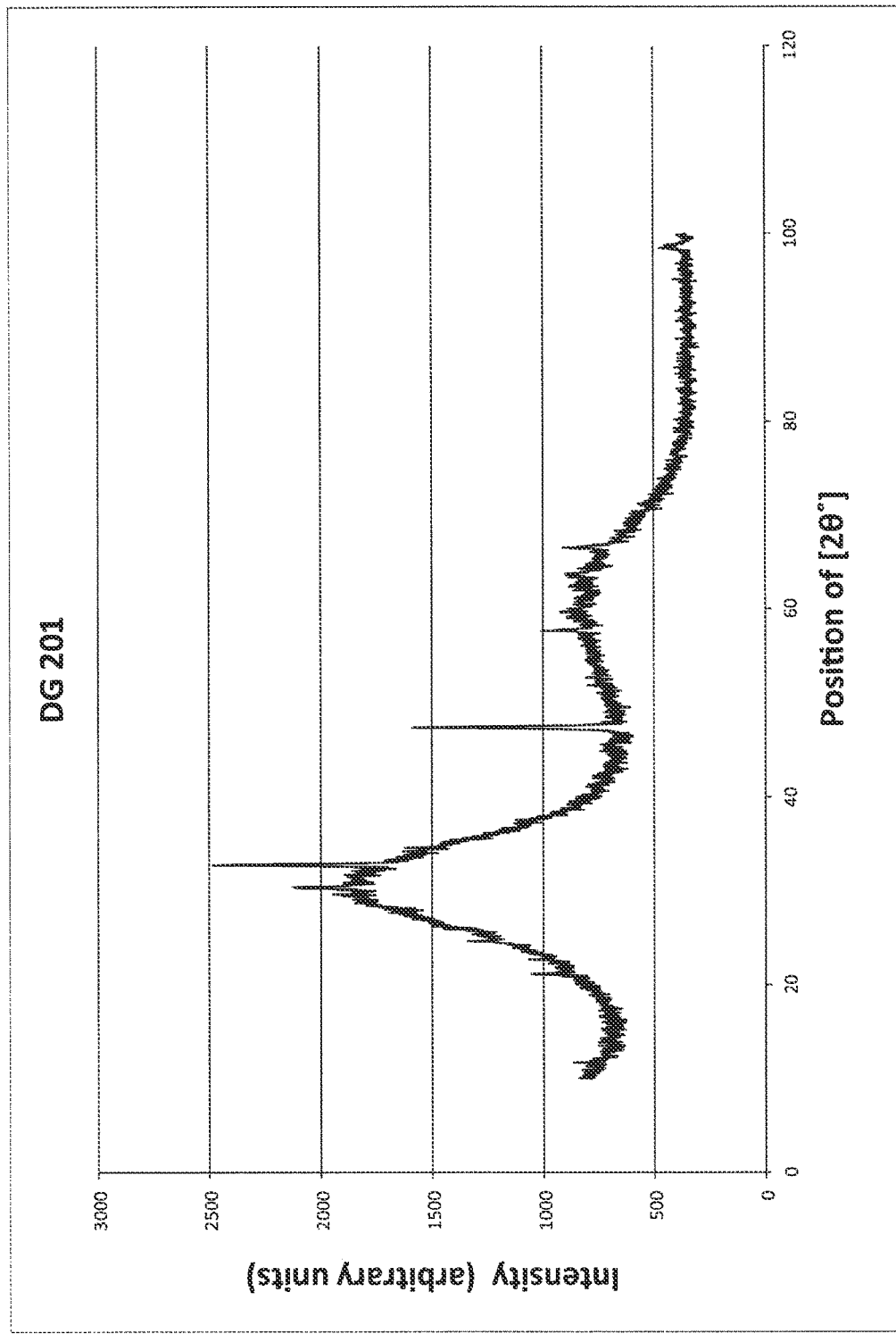
FIG. 2 is an XRD plot of sample DG201.
Figure 3:
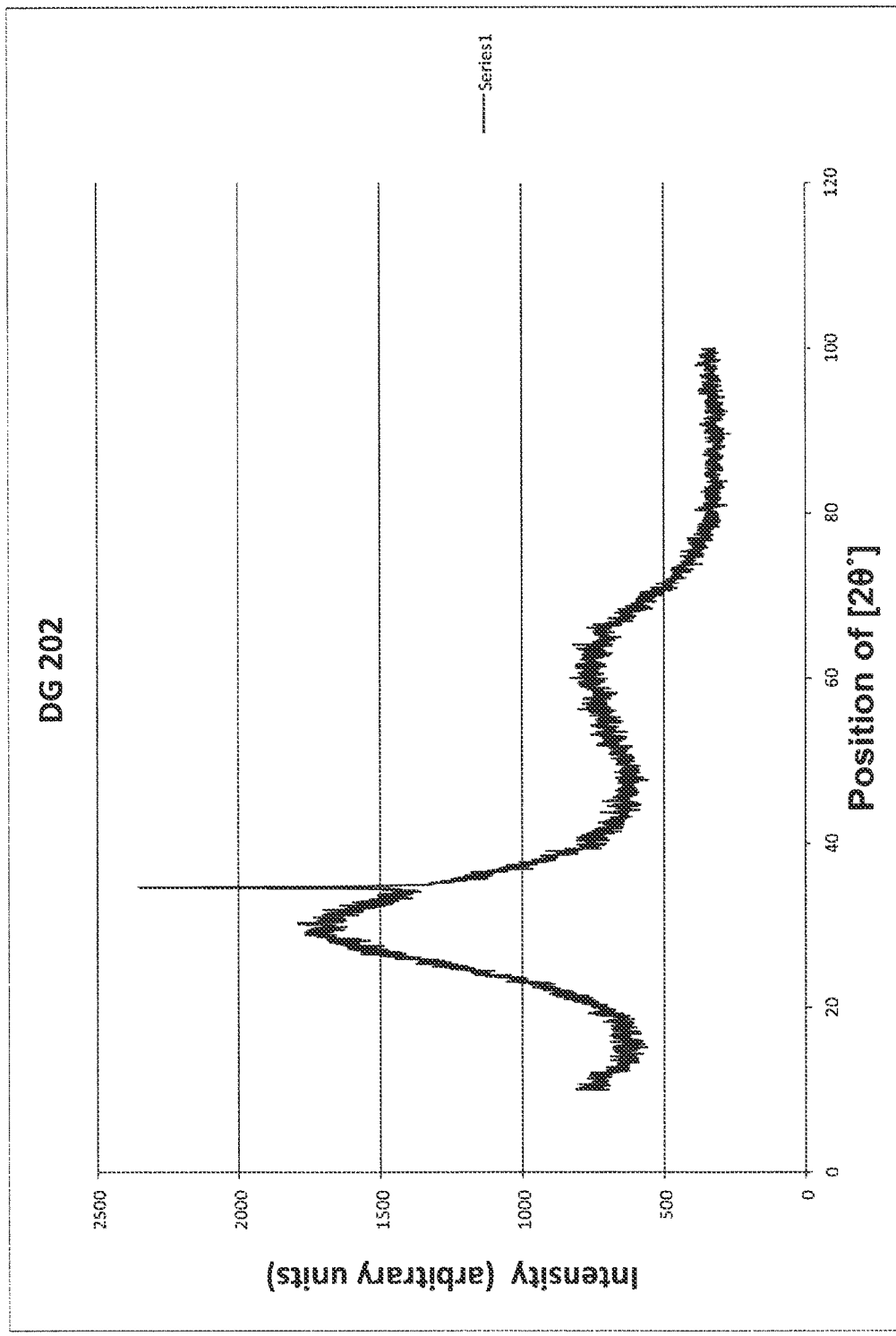
FIG. 3 is an XRD plot of sample DG202.
Figure 4:
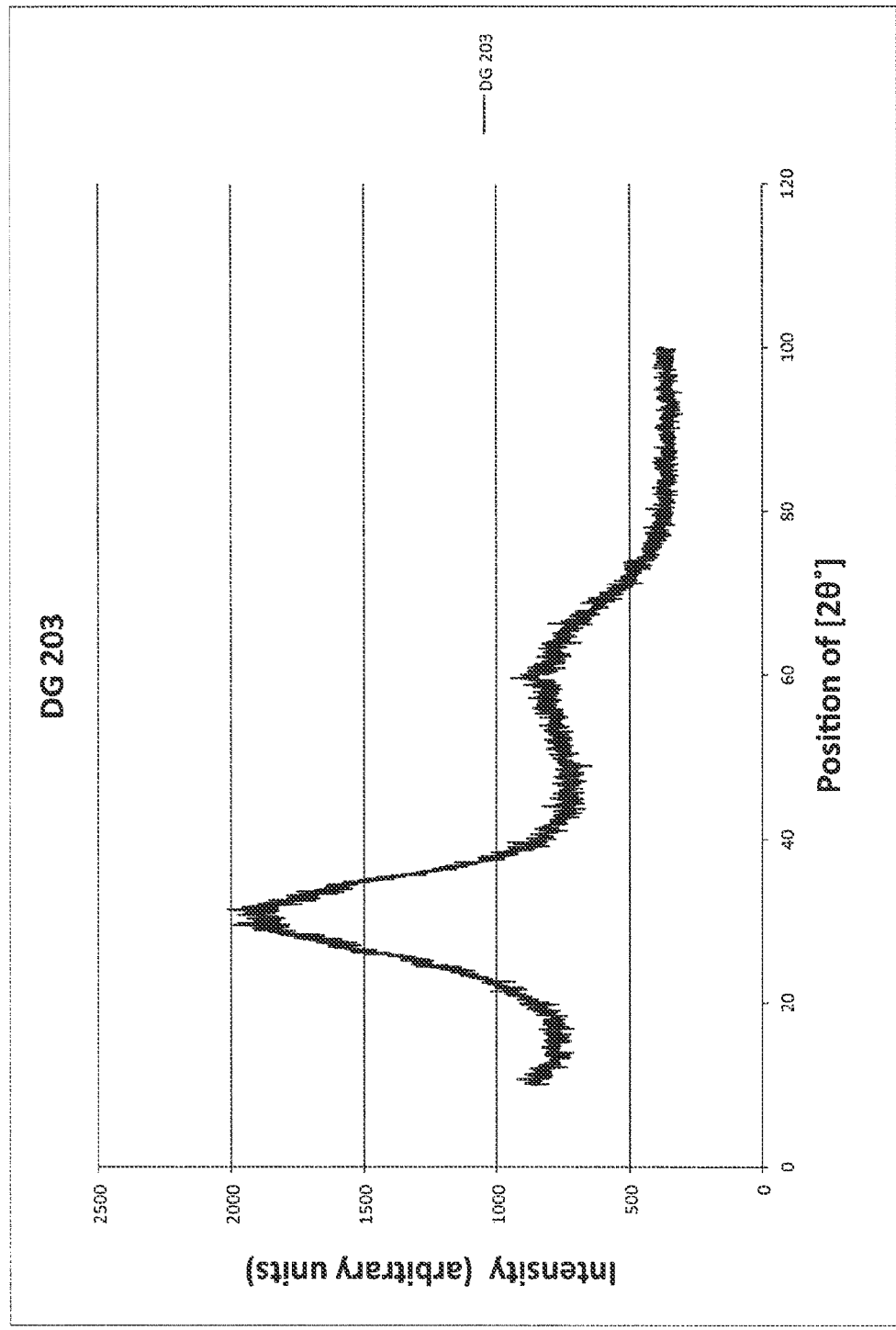
FIG. 4 is an XRD plot of sample DG203.
Figure 5:
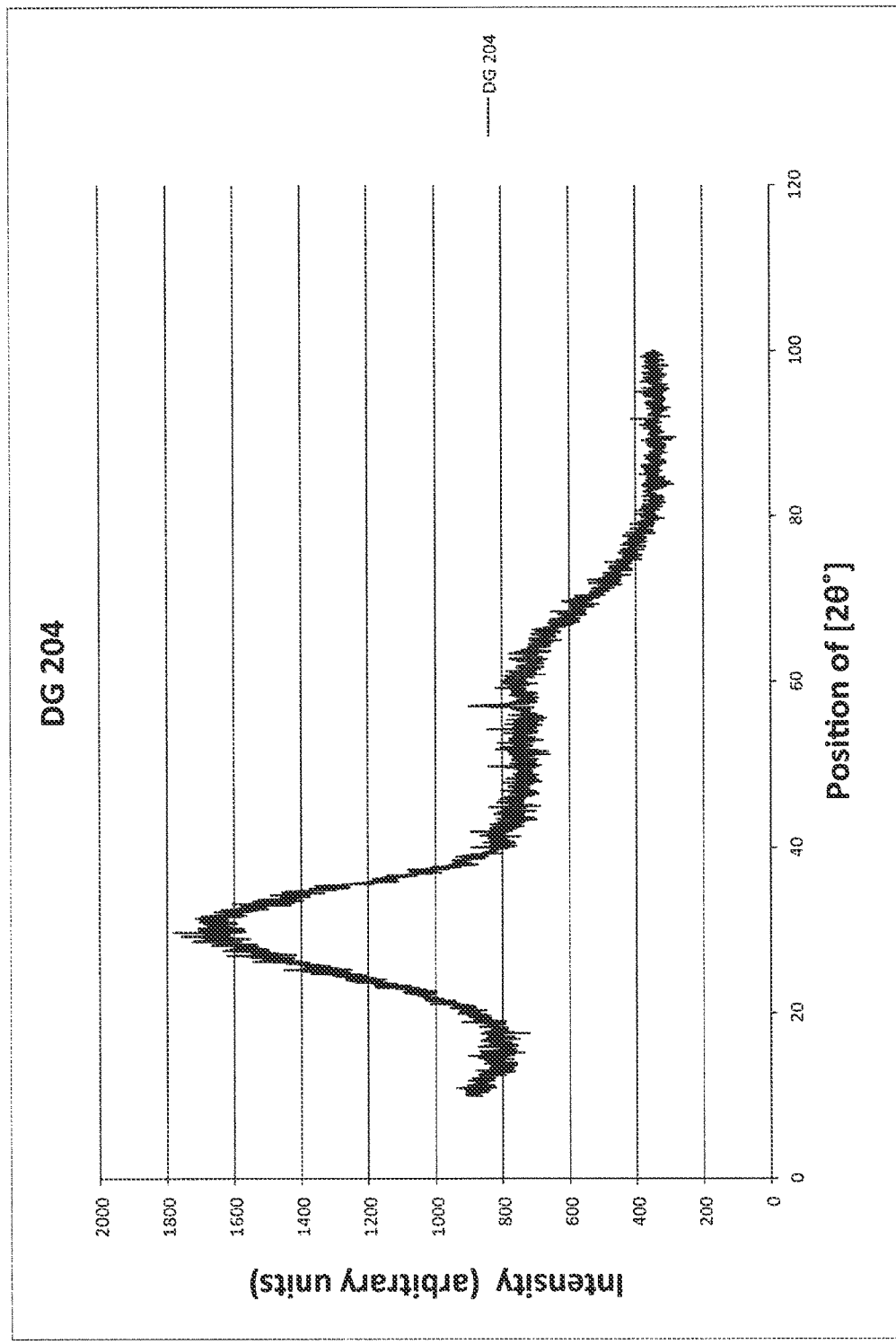
FIG. 5 is an XRD plot of sample DG204.
Figure 6:
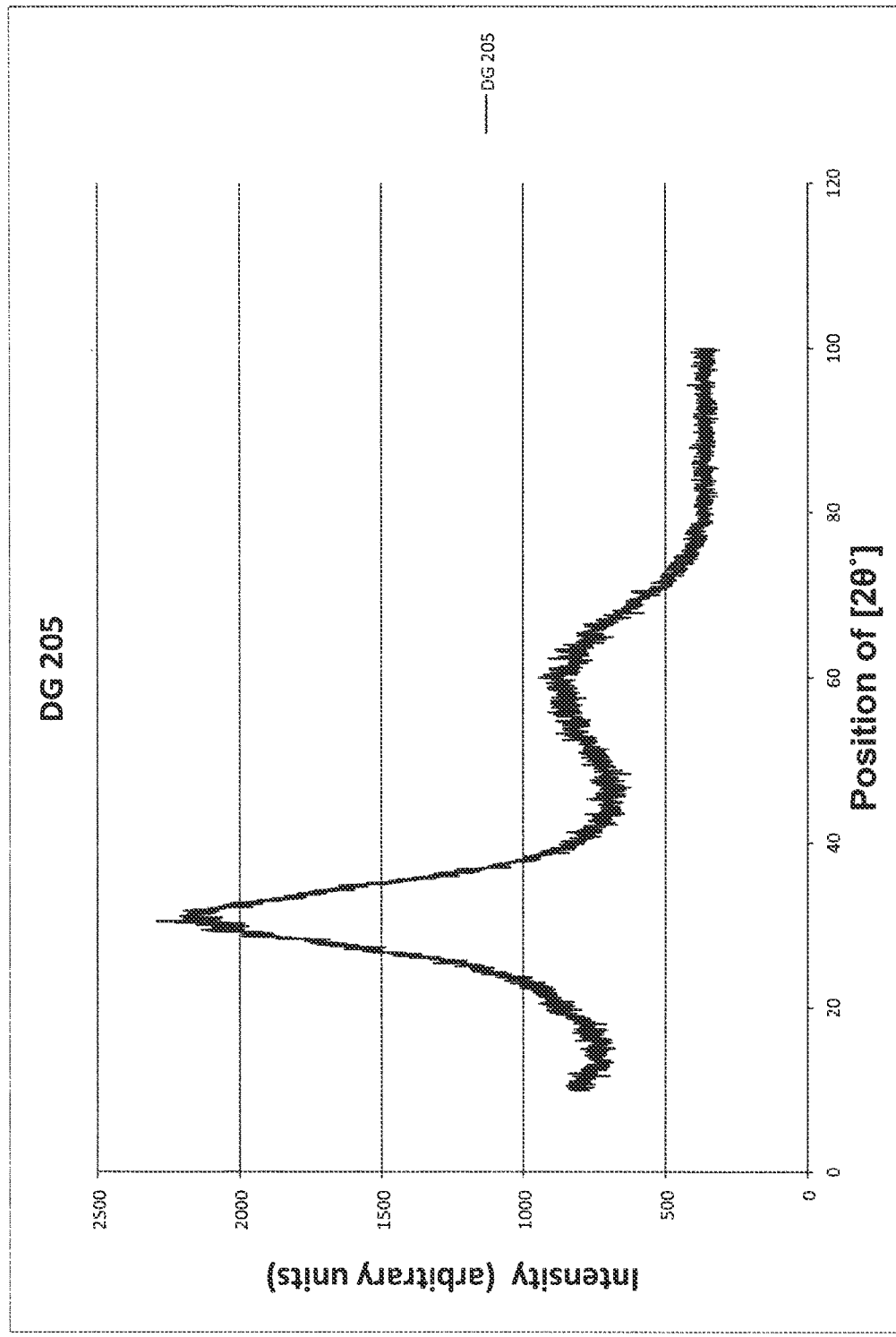
FIG. 6 is an XRD plot of sample DG205.
Figure 7:
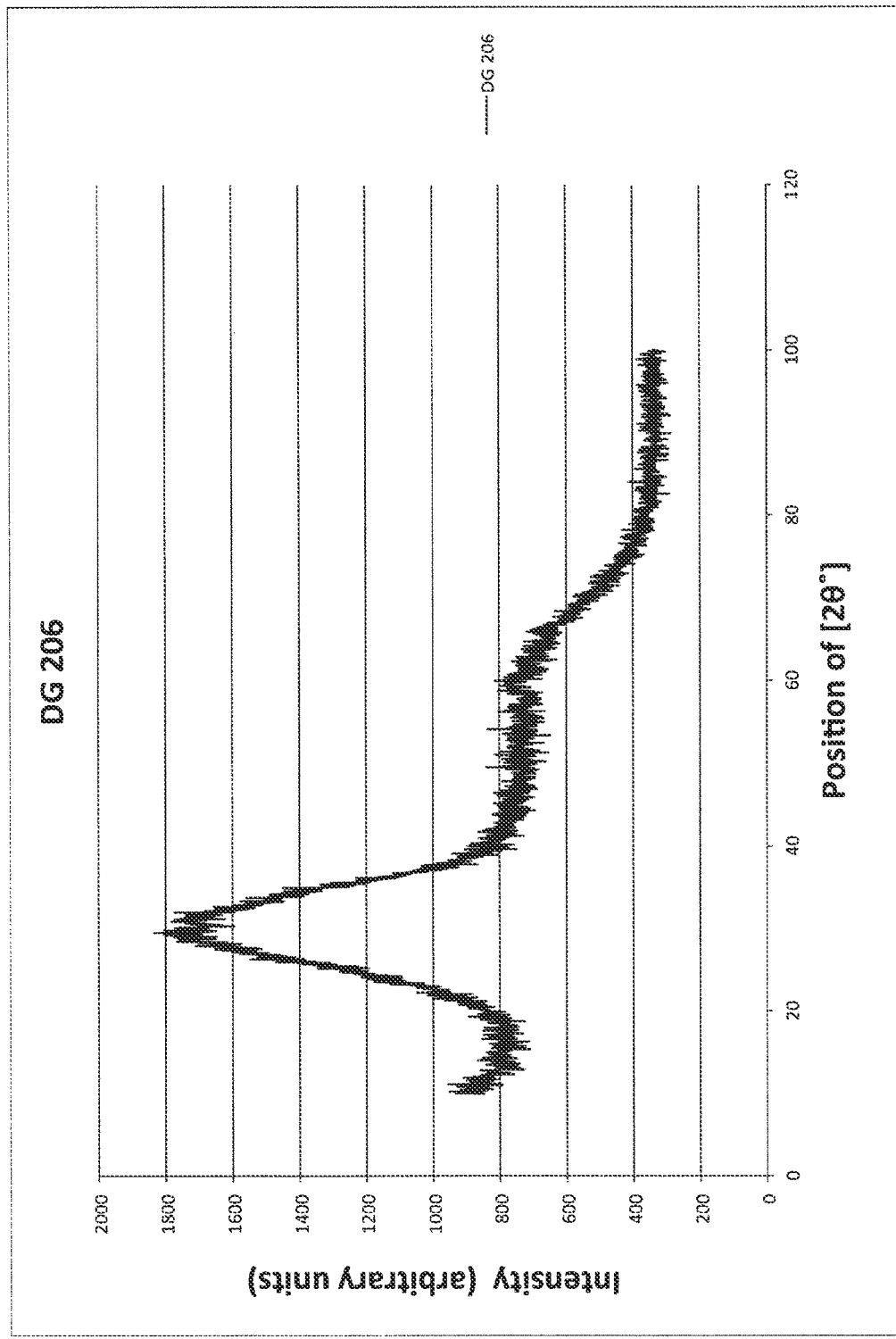
FIG. 7 is an XRD plot of sample DG206.
Figure 8:
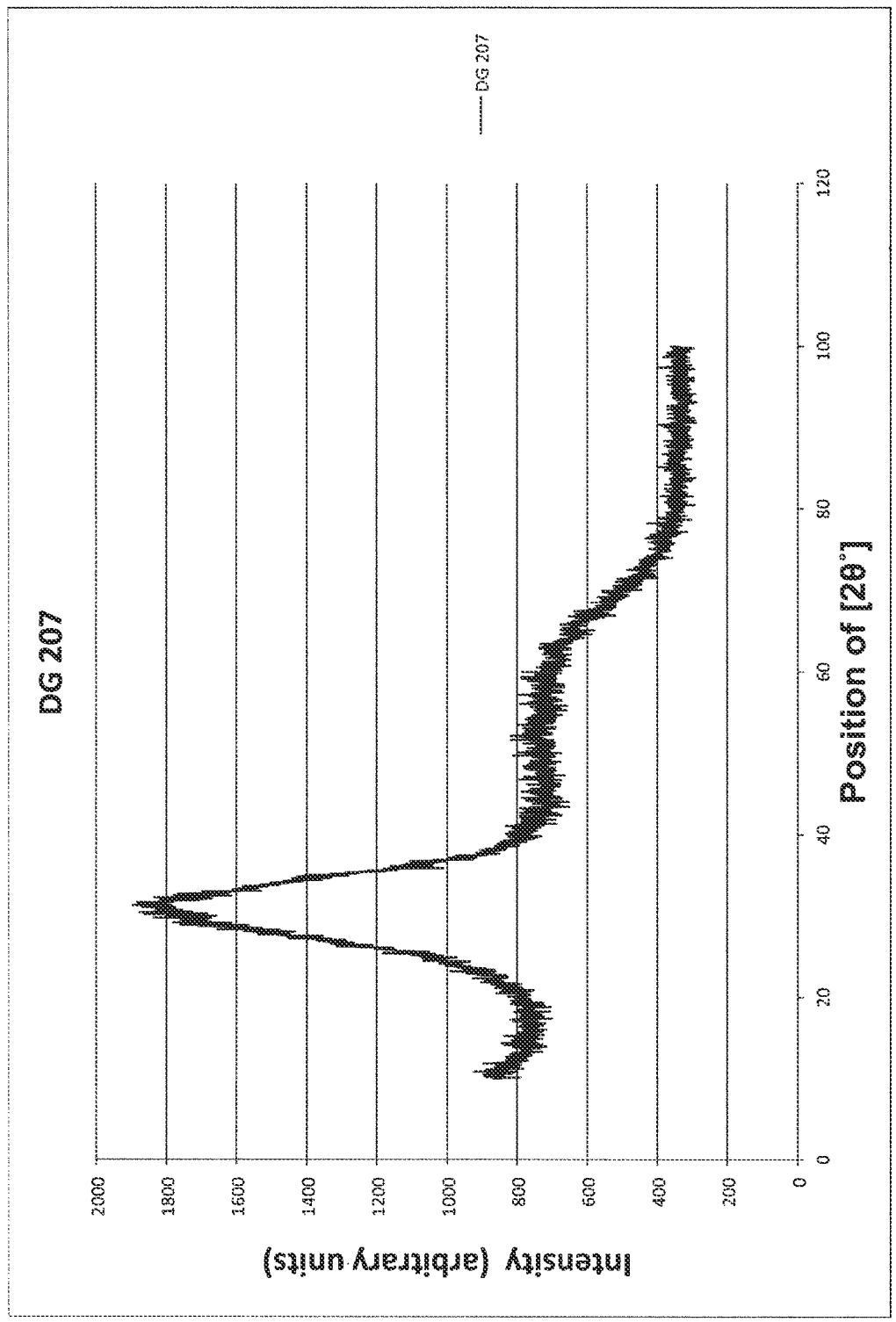
FIG. 8 is an XRD plot of sample DG207.
Figure 9:
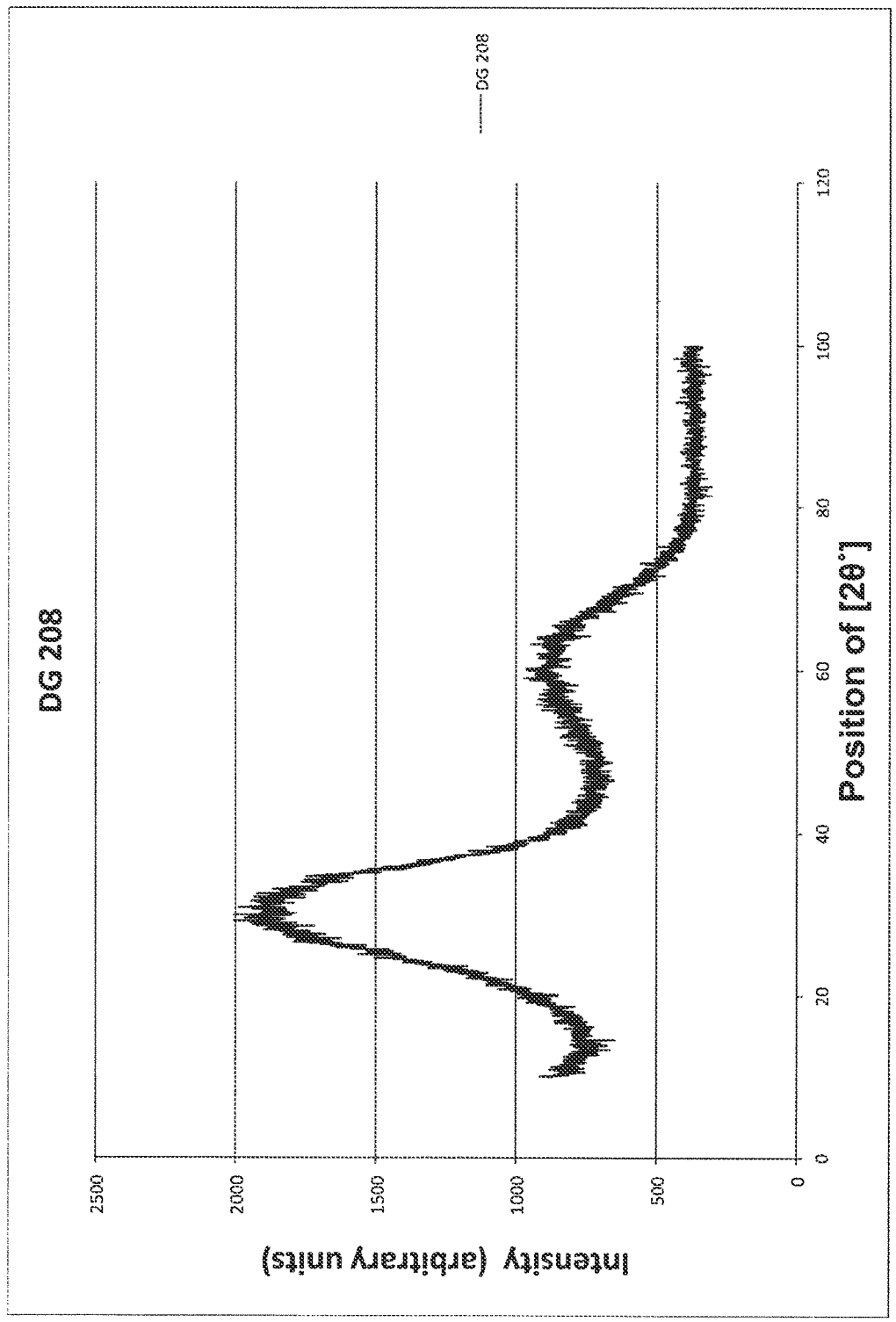
FIG. 9 is an XRD plot of sample DG208.
Figure 10:
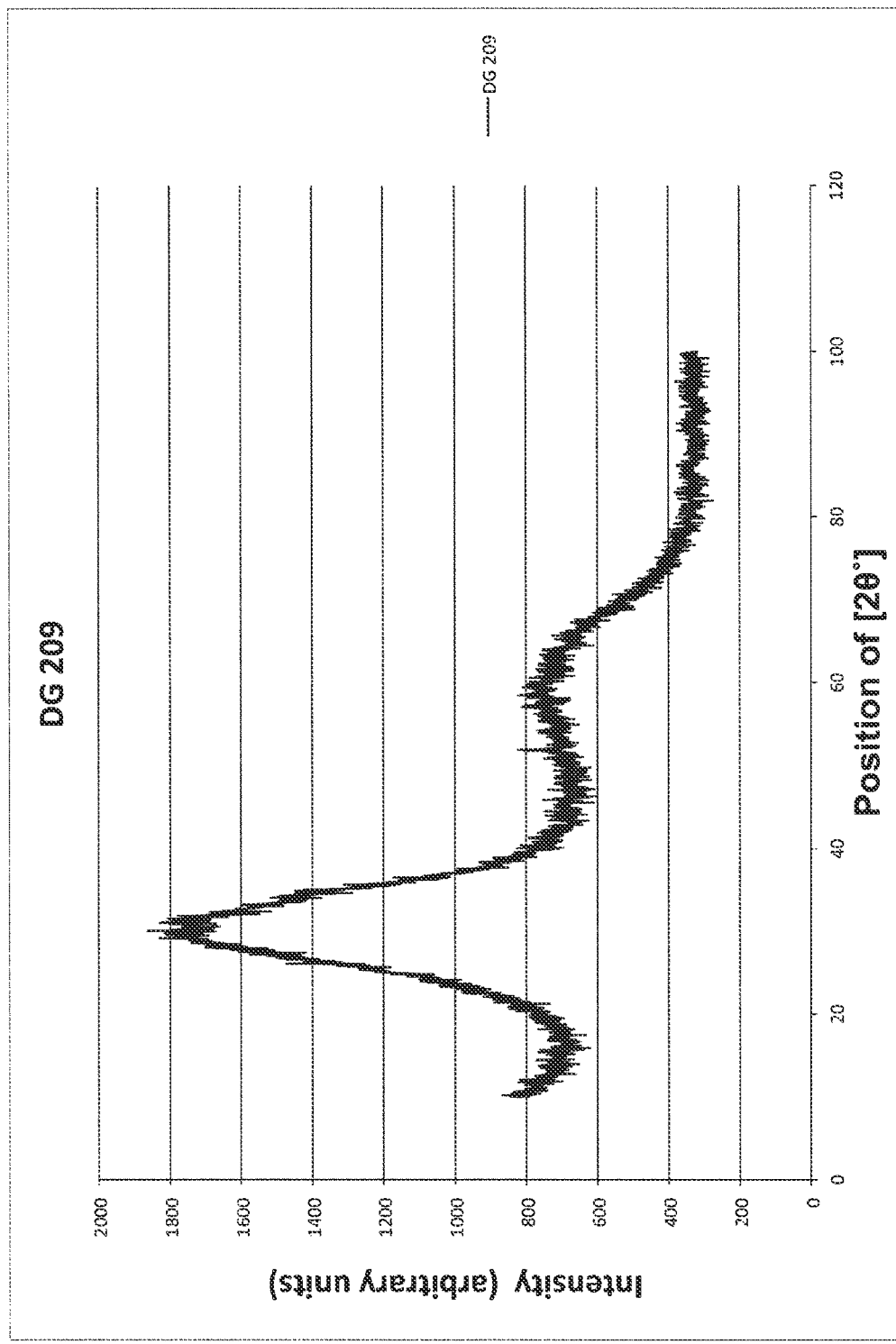
FIG. 10 is an XRD plot of sample DG209.
Figure 11:
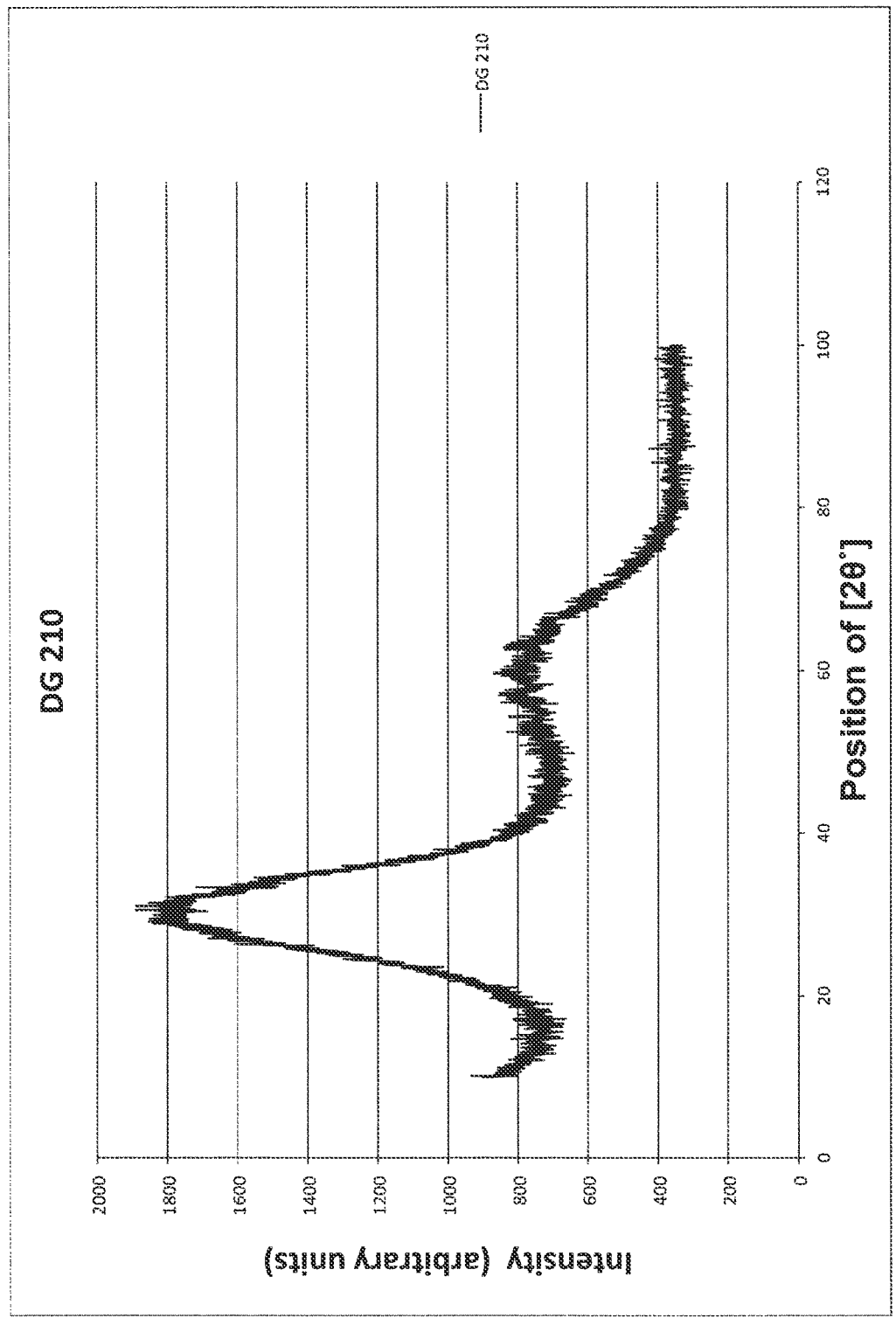
FIG. 11 is an XRD plot of sample DG210.
Figure 12:
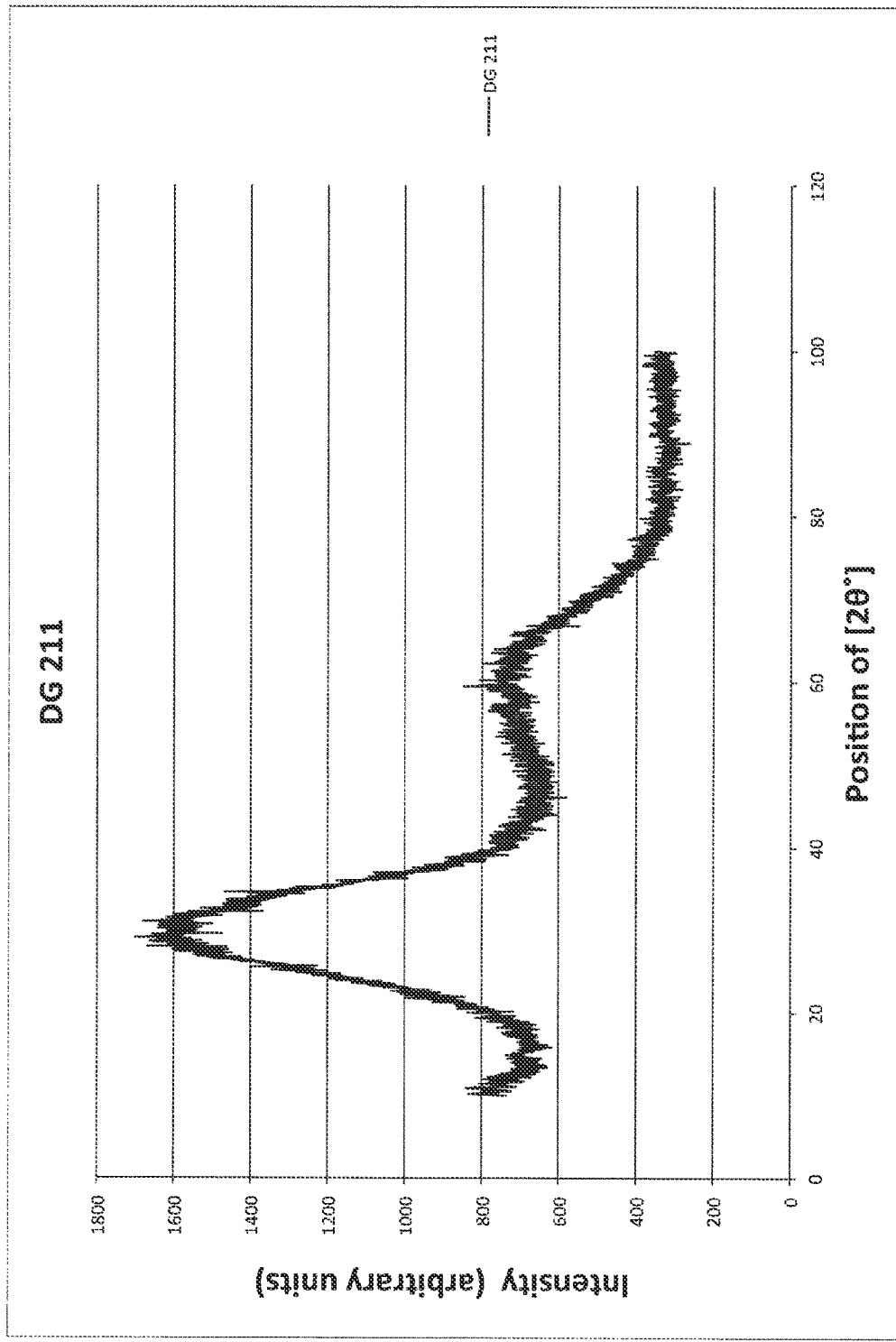
FIG. 12 is an XRD plot of sample DG211.

A GPC is a multi-component system typically comprising a glass powder component, a powder of a polyalkenoic acid, such as polyacrylic acid, and water. When all three components are mixed together, the acid attacks the glass network to release metal cations, which in turn cross-link the polymeric chains of the acid to form cement comprising reacted and unreacted glass particles embedded in a polysalt matrix.

The glass powder component is a glass ceramic and the components of that glass powder make up a network, which can be amorphous or crystalline. In some embodiments, the glass network is substantially amorphous and may comprise some crystallinity.

Surprisingly, it was determined that when germanium is added to the GPC, it may not merely isomorphically replace silicon in the glass network. In fact, GPC's including germanium provide a more consistent setting reaction—working times between 5 and 10 minutes, and setting time in between 14 and 36 min. Glasses including only silicon and no germanium, have working times between 22 seconds to 7 minutes and setting times from 1 minute to no setting. Thus, the disclosed germanium-based GPC's provide working and setting times within the range of clinical practicality and balanced with reasonable strength.

Glass Component of GPC

The glass component for the GPC include one or more of: zinc, strontium, calcium, zirconium, sodium, silicon and germanium. In some embodiments, the glass component of disclosed GPCs comprise one or more of: ZnO, SrO, $SiO_2$, $GeO_2$, $ZrO_2$, $Na_2O$ and CaO. ZnO and SrO act as network modifying components in the glass component. In some embodiments, the glass component and the GPC is substantially free of aluminosilicates and aluminum. In some embodiments, the glass component comprises no more than 0.01 mole fraction of aluminosilicates. In some embodiments no aluminum-containing ingredients are used in the preparation of the GPC.

In some embodiments, the glass component comprises mole fractions of $GeO_2$ in the ranges of 0-0.75, 0.1-0.75, 0.1-0.6, 0.2-0.5 or 0.35-0.50.

In some embodiments, the glass component comprises a mole fraction of ZnO 0.11-0.53 or 0.35-0.37. In some embodiments, the glass component comprises about 0.36 mole fraction ZnO.

In some embodiments, the glass component comprises mole fractions of $SiO_2$ in the ranges of 0-0.48, 0.2-0.48, 0-0.25 or 0-0.20.

In some embodiments, the glass component comprises mole fractions of SrO in the range of 0.025 to 0.12. In other embodiments, the glass component comprises about 0.04 mole fraction SrO.

In some embodiments, the glass component comprises mole fractions of CaO in the ranges of 0.01-0.35, 0.02-0.16, 0.02-0.12, 0.05-0.15, or 0.07-0.13.

In some embodiments, the glass component comprises mole fractions of $ZrO_2$ in the ranges of 0-0.08, 0.005-0.06, 0.01-0.055 or 0.02-0.04.

In some embodiments, the glass component comprises mole fractions of $Na_2O$ in the ranges of 0-0.08, 0.005-0.06, 0.01-0.055 or 0.02-0.04.

In some embodiments the mole fraction of $ZrO_2$ and the mole fraction $Na_2O$ are the same. This provides charge compensation.

The glass component of the GPC is prepared as a powder by mixing the desired ratio of ingredients in a mechanical mixer and packed into a crucible and fired for an hour at between 1480° C. and 1520° C. The molten glass is then quenched in deionized (DI) water at room temperature and dried overnight. The glass frit is ground to provide the desired glass powder. The glass powder is sieved to provide particle sizes of less than 45 μm.

Glass synthesis commenced with the successful melt of the Zn-glass described in U.S. Pat. No. 7,981,972 (see reference 1). The mole fractions of this composition is:

0.48 $SiO_2$, 0.36 ZnO, 0.12 CaO, 0.04 SrO.

Germanium ($GeO_2$), and zirconium ($ZrO_2$) were substituted, individually, into the Zn-based glass for silica and calcium respectively, in a series of experimental melts to determine the substitution limits for both substances. Germanium successfully produced a glass over a range of 0-0.48 mole fractions, although no compositions with $GeO_2$ levels greater than 0.48 mole fraction were attempted. $ZrO_2$ successfully produced a glass when incorporated between 0-0.05 mole fractions, but failed to produce a glass at 0.08 mole fraction. $ZrO_2$ was matched on a mole fraction basis with $Na_2O$ for charge compensation (see references 2 and 3). The original glass having mole fractions 0.48$SiO_2$, 0.36ZnO, 0.12CaO and 0.04SrO was tested in comparison to the compositions of the present disclosure and is referred to as DG200.

Preparation of GPC

To prepare the GPC, the glass powder is mixed with an aqueous solution of a polyalkenoic acid in a ratio of about 2:1 to about 1:1. In some embodiments, the polyalkenoic acid solution can be 40-60% by weight polyalkenoic acid powder and distilled water. In other embodiments, the polyalkenoic acid solution is 50%, by weight, polyalkenoic acid powder and distilled water. In some embodiments, the polykenoic acid can have an average molecular of 1,150 to 1,500,000. In other embodiments, the polykenoic acid can have an average molecular of 1,150 to 383,000; 1,150 to 114,000; 1,150 to 22,700. In one embodiment, the polyalkenoic acid powder has a weight average molecular weight ($M_w$) of 12,700.

EXAMPLES

Example 1

Generation and Application of Mathematical Models Using a Design of Experiments (DoE) Approach To estimate the coefficients of a second order canonical Scheffé polynomial, a quadratic user-defined design with twelve experiments representing different compositional variants (design points) within a defined domain (design space) was constructed using Design-Expert 8.0.4 software (Stat-Ease, Inc.). These design points were determined based on the constrained ranges for each composition: with six experiments set at the extreme vertices (V); a further five investigating axial plane-centroids (A-CB) and one overall centroid (C) within the defined design space. These points are in clear agreement with Scheffé's proposal that the interesting points of a domain are at its tops, at the middle of the sides, at the middle of the faces and its centre of gravity (Table 1). With the mixture design method, an equation is obtained. This formula connects Y, (ie. Response), with the four compositional factors ($SiO_2$, $GeO_2$, ZrO/NaO and CaO, noted respectively as $X_1$, $X_2$, $X_3$ and $X_4$).

The Scheffé quadratic polynomial equation fitted for working time, setting time, exotherm, compression strength, biaxial flexural strength and modulus responses is:

$$Y = \beta_1 X_1 + \beta_2 X_2 + \beta_3 X_3 + \beta_4 X_4 + \beta_{12} X_1 X_2 + \beta_{13} X_1 X_3 + \beta_{14} X_1 X_4 + \beta_{23} X_2 X_3 + \beta_{24} X_2 X_4 + e$$

where $X_1$ to $X_4$ represent the compositional factors, $\beta_{1-4}$ coefficients represent the effect of the individual compositional factors $X_{1-4}$; $\beta_{12-24}$, are the coefficients of regression which represent the effects of two-way interactions between the compositional factors and e is the residual. From the estimated coefficients of a quadratic model presented in pseudo and actual values, the effect of each component can be derived. Mixture experiment models were developed relating the response variables to proportions of pseudo-components. Pseudo-component proportions ($z_i$) are calculated as:

$$z_i = (x_i - L_i)/(1 - \Sigma L)$$

where $x_i$ stands for the original component proportions, $L_i$ stands for the lower bound constraint (limit) for the $i^{th}$ component, L stands for the sum of all lower bound constraints (limits) for all components in the design, and 1 represents the mixture total. The pseudo-components are combinations of the original (actual) components, which rescale the constrained composition region so that the minimum allowable proportion of each pseudo-component is zero. This transformation may provide for more precisely estimating model coefficients compared to using the actual component system, and as such the coefficients derived based on the pseudo-component scaling is referred to in the context of the discussion to follow. Model validity, in terms of experimental versus calculated data points and graphical representation (contour plots) however, is presented in terms of actual component coding. When several response characteristics $y_1, y_2, \ldots, y_n$ have been modeled in the proportions of the same set of q components, the desirability function approach was implemented to identify where in the compositional design space the best overall set of properties (such as working time, compression strength and biaxial flexural strength and modulus) may be obtained.

TABLE 1

Design of Mixtures Compositions

| | ZnO | SrO | SiO$_2$ | GeO$_2$ | ZrO$_2$ | Na$_2$O | CaO |
|---|---|---|---|---|---|---|---|
| DG200 | 0.36 | 0.04 | 0.48 | 0 | 0 | 0 | 0.12 |
| DG201 | 0.36 | 0.04 | 0 | 0.447 | 0.0335 | 0.0335 | 0.087 |
| DG202 | 0.36 | 0.04 | 0 | 0.48 | 0 | 0 | 0.12 |
| DG203 | 0.36 | 0.04 | 0.215 | 0.215 | 0.05 | 0.05 | 0.07 |
| DG204 | 0.36 | 0.04 | 0.48 | 0 | 0.05 | 0.05 | 0.02 |
| DG205 | 0.36 | 0.04 | 0 | 0.38 | 0.05 | 0.05 | 0.12 |
| DG206 | 0.36 | 0.04 | 0.447 | 0 | 0.0335 | 0.0335 | 0.087 |
| DG207 | 0.36 | 0.04 | 0.38 | 0 | 0.05 | 0.05 | 0.12 |
| DG208 | 0.36 | 0.04 | 0 | 0.48 | 0.05 | 0.05 | 0.02 |
| DG209 | 0.36 | 0.04 | 0.215 | 0.215 | 0.025 | 0.025 | 0.12 |
| DG210 | 0.36 | 0.04 | 0.223 | 0.223 | 0.0335 | 0.0335 | 0.087 |
| DG211 | 0.36 | 0.04 | 0.24 | 0.24 | 0.025 | 0.025 | 0.07 |

Example 2

Glass Production

One half mole of each component was weighed out using an analytical balance (ABJ 120-4m, Kern & Sohn GmbH, Germany) using analytical grades of zinc oxide, strontium carbonate, silica, germanium oxide, zirconia, sodium carbonate, and calcium carbonate (Sigma-Aldrich, Oakville, CAN). For each composition in Table 1, amounts for each component was weighed to arrive at the desired ratio. Powder compositions were mixed in a mechanical mixer (Twin shell dry blender, Patterson-Kelly, USA) for 1 hour and then dried in an oven at 100° C. for 1hour. Compositions were than packed into 50 mL platinum crucibles (Alpha Aesar, USA) and fired between 1480° C. and 1520° C. for 1 hour in a high temperature furnace (Carbolite RHF 1600, UK). Molten glass was removed was removed and quenched in deionized water at room temperature and dried overnight in an oven at 100° C. The resulting glass frit was ground using a planetary ball mill (Pulverisette 7, Fritsch GmbH, Germany) and sieved (Cole-Palmer, Montreal, Canada) to retrieve glass powder with particle size less than 45 μm.

The glasses made include those without germanium for comparison and modeling purposes. This method produced both germanium and non-germanium glasses (table 1), that are representative examples of the full compositional space bounded by the aforementioned constraints. These examples compositions can be evaluated to ascertain specific contributions of SiO$_2$, GeO$_2$, ZrO$_2$/Na$_2$O, and CaO with regards to the properties of interest.

Example 3

Characterization of Glasses

Differential Scanning Calorimetry (DSC)—

All powders were analyzed with DSC (Q200 DSC, TA Instruments, Grimsby, ON) to determine the glass transition temperature ($T_g$). This process involved 45 to 50 mg of powder placed into stainless steel closed pans, while the reference pan was left empty. Samples were heated at a rate of 10° C./min to a maximum temperature of 725° C. Q Series software (TA Instruments, Grimsby, CAN) was used to determine $T_g$, the temperature corresponding the point of inflection between two user-identified plateaus before and after the endothermic glass transition event. The measured $T_g$ are shown below in Table 2:

TABLE 2

Glass Transition Temperatures

| Composition | $T_g$ [° C.] |
|---|---|
| DG200 | 676.4 |
| DG201 | 593 |
| DG202 | 605.2 |
| DG203 | 612.7 |
| DG204 | 656.93 |
| DG205 | 601.28 |
| DG206 | 644.53 |
| DG207 | 640.24 |
| DG208 | 581.76 |
| DG209 | 624.17 |
| DG210 | 612.23 |
| DG211 | 621.87 |

X-Ray Diffraction (XRD)—

The 12 glasses were analyzed with X-ray diffraction (XRD) to determine whether the glasses were amorphous materials. XRD measurements for the particles were performed using an INEL CPS-120 diffractometer with a curved position sensitive detector coupled to an X-ray generator (40 kV; 35 mA) and equipped with a copper (Cu) target X-ray tube. Samples were prepared by pressing the glass powders into hollow square steel wafers. A monochromator in the incident beam path limits the wavelengths striking the sample to Cu K$\alpha$1,$\alpha$2. The X-ray beam is incident upon the sample at approximately 6° and the curved position sensitive detector collects all scattered X-rays in the scan angle range 10°<2$\theta$<100°. The results confirmed that the glasses were indeed amorphous. The XRD plots are provided in FIGS. 1-12.

Example 4

Glass Annealing

Glasses were annealed to relieve internal stresses within the glass network and improve handling characteristics as described by Neve, et al. The 12 glasses were annealed in the furnace at temperatures 30° C. below their respective glass transition temperatures. Clean platinum crucibles were loosely filled with glass powders and placed in the furnace once the furnace temperature achieved steady state. Temperatures were monitored using a high temperature type-K thermocouple (Omega, Laval, CAN), connected to a digital thermometer (Omega, Laval, CAN). Samples were left at temperature for 3 hours, after which the furnace was turned off and the samples were left to cool in the furnace overnight. Annealed glass samples were removed and transferred to 20 mL disposable glass vials and placed in a desiccator at room temperatures for storage.

Example 5

Cement Preparation

Cements were prepared by mixing glass power with aqueous solution of polyacylic acid (PAA); M$_w$=12,700 (E6, Advanced Healthcare Limited, Kent, UK) on dental mixing pads using a dental spatula. Throughout all experiments the powder to liquid ratio was set at 2:1.5, a ratio consistent with the literature of GPCs for vertebroplasty (as shown in references 5-7). The PAA solution was a 50%, by weight, PAA powder and distilled water. All weights and volumes were measured to ±0.001 g and ±0.001 mL respectively.

Example 6

Determination of Working Time (WT) for Cements

Figure 13:
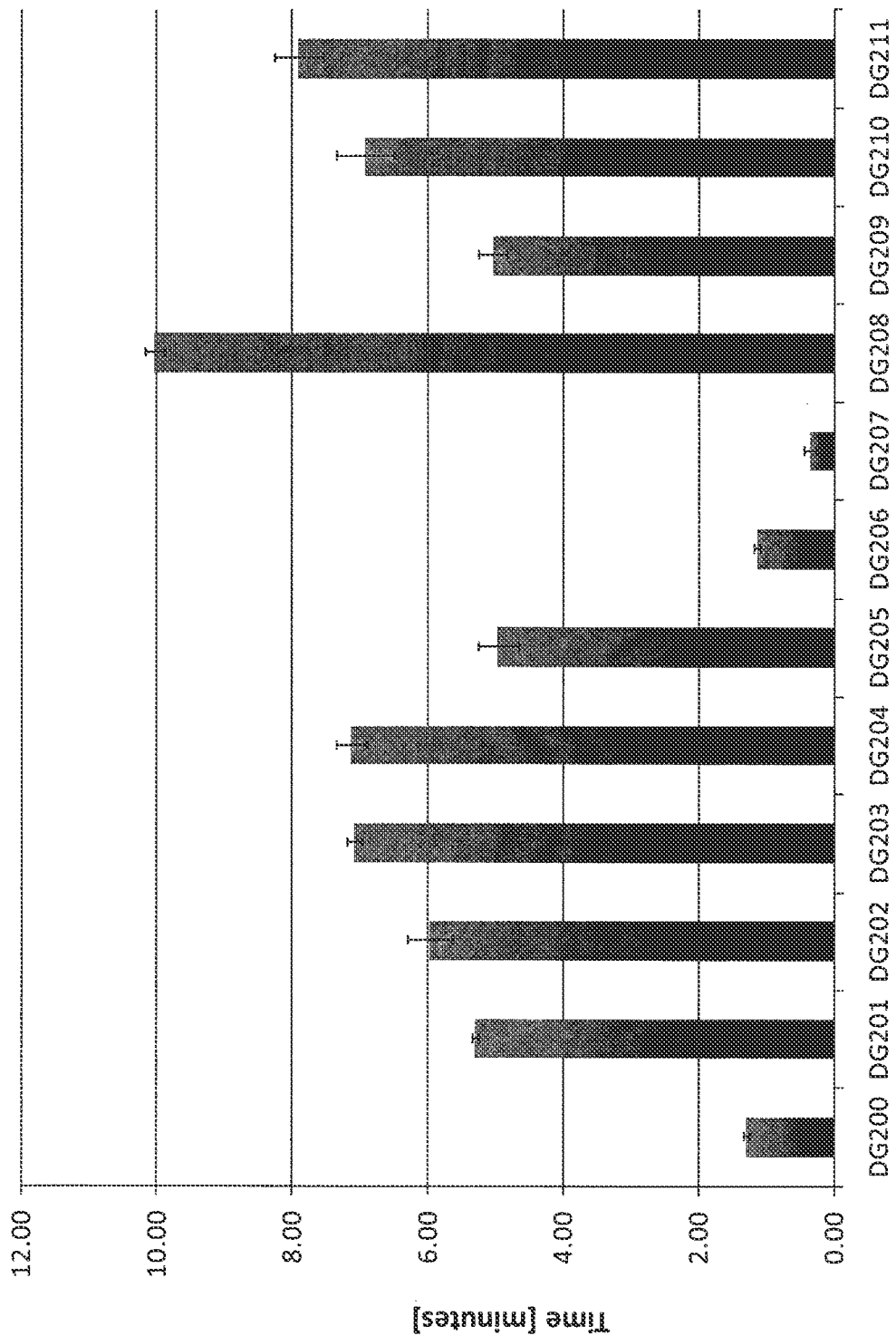
FIG. 13 illustrates the results of working time experiments on GIC samples.

The working time of the cement was determined in accordance with the procedure set out in ISO9917—Dentistry—Water-based cements (see reference 8). Working time is defined as the "period of time, measured from the start of mixing, during which it is possible to manipulate a dental material without an adverse effect on its properties." Appropriate amounts of glass powder and PAA liquid were measured out on a dental mixing pad to make up 0.4 g of cement. The timer was started and components were thoroughly mixed by hand using a dental spatula until a homogenous solution was achieved, with no visual signs of PAA powder. The liquid cement was worked with the dental spatula until it thickened to a viscosity similar to that of chewing gum, at which point the timer was stopped. Each of the 12 cements were tested 3 times, the average of which was recorded as the working time. The results are set out in Table 3 and FIG. 13. Clinically useful working times are between 5 and 10 minutes. As can be seen DG200, the predicate aluminum-free GPC, is well short of this range and thus impractical for clinical use.

Example 7

Determination of Setting Time (ST) for Cements

Figure 14:
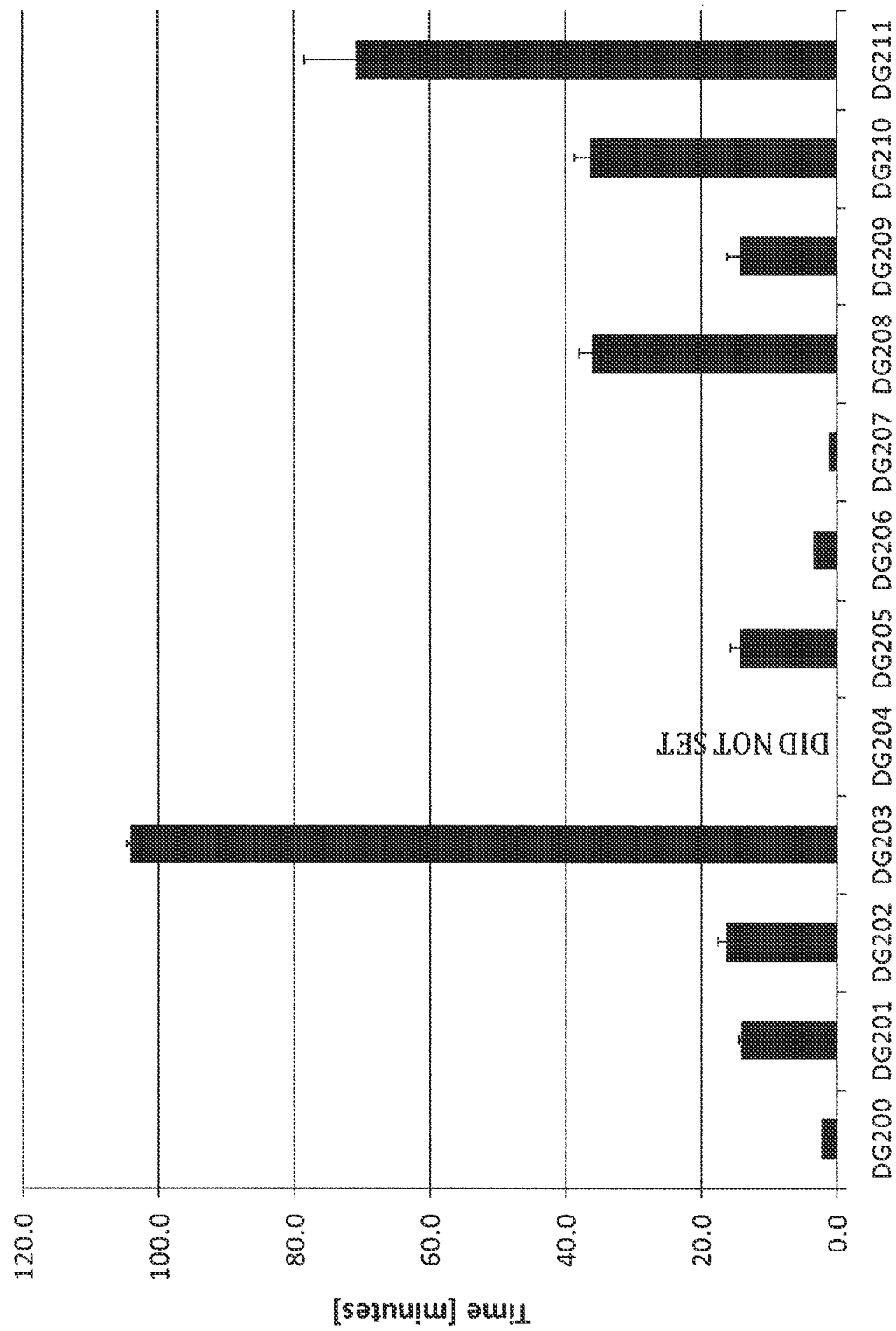
FIG. 14 illustrates the results of setting time experiments on GPC samples.

Setting times were also evaluated following ISO9917. The apparatus used for this procedure are listed as follows:
  8 mm×10 mm×5 mm aluminum mold, with sides covered in a thin layer of petroleum jelly
  75 mm×100 mm×8 mm aluminum plate wrapped in aluminum foil
  Cabinet maintained at a temperature of (37±1°) C.
  Gilmore needle with a mass of 453 g and a flat indenter tip with Ø 1.1 mm
  ×2 magnifying lens
  One gram of cement was prepared and loaded into the mold, placed on the aluminum plate. At the end of mixing the timer was started. Sixty seconds after the end of the mixing the assembly was placed in the cabinet. Sixty seconds prior to the material's working time, the assembly was gently raised upwards such that the cement's surface was pressed into the tip of the indenter. This process was repeated intermittently until the cement could take the full weight of the indenter for 5 s, whilst making a full circular indentation in the cement. The indentation process then continued every 30 s until the indenter tip failed to make a complete circular impression in the cement's surface when viewed at 2× magnification. The timer was stopped, and the elapsed time recorded. This process was repeated twice more with the indentation process starting 3 min before the previous recorded time. Each cement composition was tested three times and the setting time was taken as the average. The results are shown in Table 3 and FIG. 14. DG 204 did not set. Useful setting times in a clinical setting depend on the application. For some applications, around 18 minutes is a useful setting time.

TABLE 3

| Sample | Design Points | WT (sec) | ST (sec) | EX (° C.) |
|---|---|---|---|---|
| DG 200 | V | 77 | 125 | 41 |
| DG 201 | V | 318 | 838 | 30 |
| DG 202 | V | 358 | 967 | 31 |
| DG 203 | V | 425 | 6259 | 27 |
| DG 204 | V | 428 | n/a | 27 |
| DG 205 | V | 298 | 848 | 31 |
| DG 206 | A-CB | 69 | 196 | 36 |
| DG 207 | A-CB | 22 | 63 | 43 |
| DG 208 | A-CB | 602 | 2155 | 27 |
| DG 209 | A-CB | 302 | 854 | 30 |
| DG 210 | A-CB | 416 | 2165 | 29 |
| DG 211 | C | 474 | 4248 | 28 |

Example 8

Determination of Setting Exotherm (EX) for Cements

Three T-type thermocouples (Omega, Laval, CAN) were used with reference junctions in ice water at 0° C. Two thermocouples were used to measure cement temperatures, while the third was used to measure the ambient temperature. Alligator clips joined the thermocouple leads to BNC connectors that fed into a BNC connector board (BNC-2120, National Instruments, Vaudreuil-Dorion, CAN), connected to a NI-PCI-6035 data acquisition card (National Instruments, Vaudreuil-Dorion, CAN). LabView 9.0 (National Instruments, Vaudreuil-Dorion, CAN) was used to construct a program to obtain the voltages of the three thermocouples, calculate temperatures, graphically and numerically display the temperatures in real time, and record the data of the two cement thermocouples to separate text files. The program sampled data at a rate of 5000 Hz, recording 500 samples at a time. The mean voltage (V) of these samples was found, and temperature (T) calculated in degrees Celsius according to the T-type thermocouple equation:

$$T = a_0 + a_1 V + a_2 V^2 + a_3 V^3 + a_4 V^4 + a_5 V^5 + a_6 V^6 + a_7 V^7$$

wherein,
  $a_0 = 0.100860910$
  $a_1 = 25727.94369$
  $a_2 = -767345.8295$
  $a_3 = 78025595.81$
  $a_4 = -9247486589$
  $a_5 = 6.97688 \text{ E}+11$
  $a_6 = -2.66192 \text{ E}+13$
  $a_7 = 3.94078 \text{ E}+14$
This process was repeated every 0.1 s until the user stopped the data collection.

To validate the system, two test procedures were performed. First, to investigate the accuracy of the system, the three thermocouples were placed a beaker of boiling water and temperatures were recorded until temperature stabilized at the boiling point. These temperatures were compared against the temperature measurements of a calibrated digital thermometer of known accuracy (HH508 with K-type thermocouple, Omega, Laval, CAN).

Figure 15:
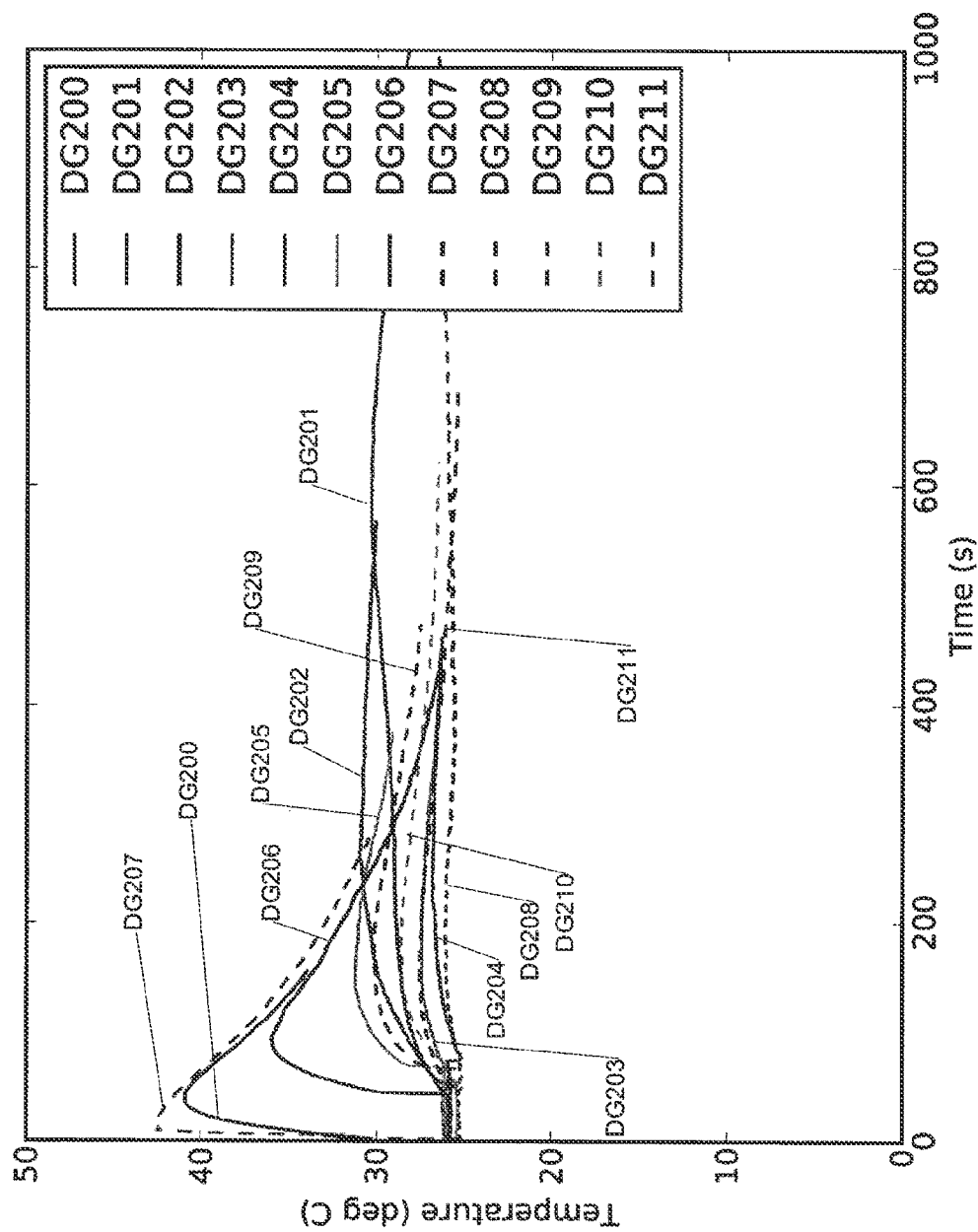
FIG. 15 illustrates maximum temperatures and exotherm profiles of GPC samples.

One gram of cement was prepared and loaded into a plastic mold (Ø 15 mm×10 mm) The thermocouples were inserted into the center of the bolus of cement and left there until the temperature peaked and decreased by more than 1° C. from the maximum temperature. Data was plotted and analyzed using Python 2.6.6.2 (Python Software Foundation, www.python.org). This process was conducted three times for each of the 12 cements. The maximum temperature was taken as the highest temperature achieved by the cement during any of the three trials. The maximum temperature is shown in Table 3. FIG. 15 illustrates the exotherm profiles for the samples. As can be seen, the tested samples reach relatively low maximum temperatures compared to alternative cements on the market which reach 60-120° C. As mentioned previously, high temperatures can lead to damage to surrounding healthy tissues and is thus undesirable.

Example 8

Statistical Analysis and Modeling Assessing Effect of Components on Working Time, Setting Time and Setting Exotherm Statistical Analysis—

Figure 16A:
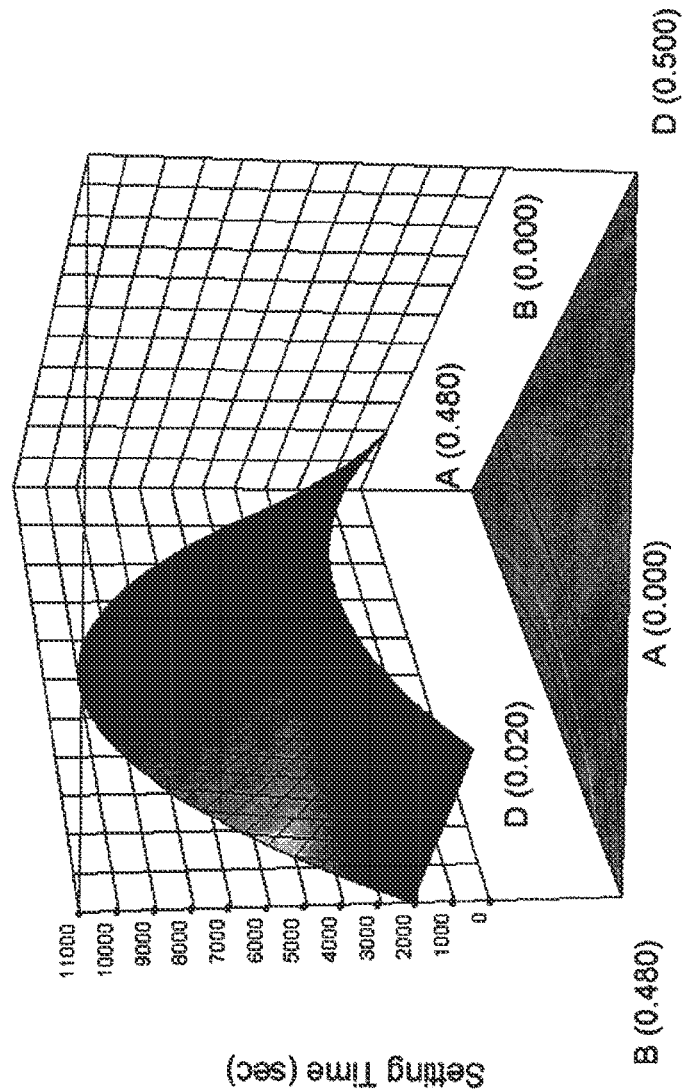
FIGS. 16A and B are 3D and 2D, respectively, contour plots illustrating the effect of varying glass composition on setting time when varying $SiO_2$, CaO and $GeO_2$ compositions.
Figure 16B:
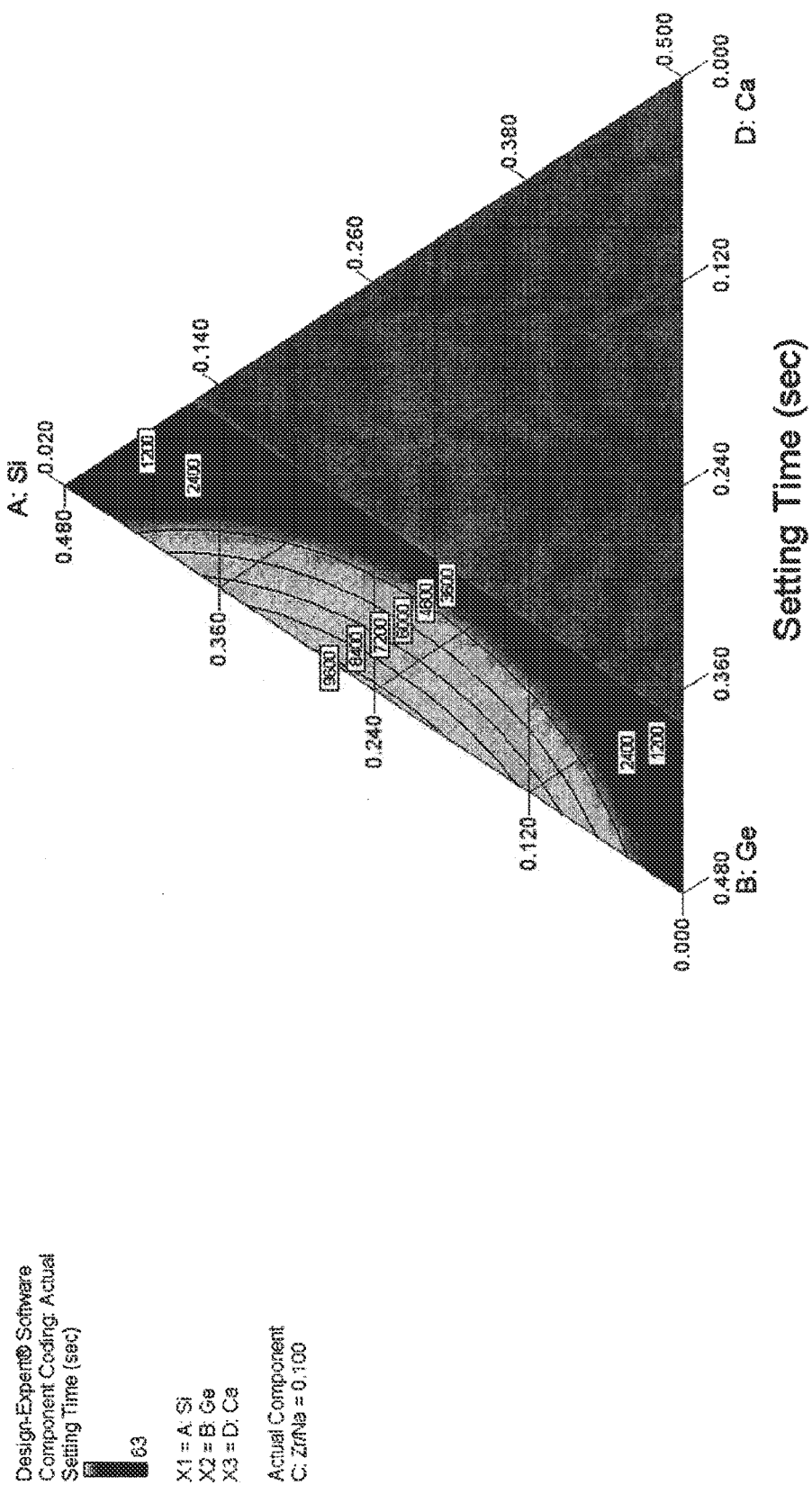
Figure 17A:
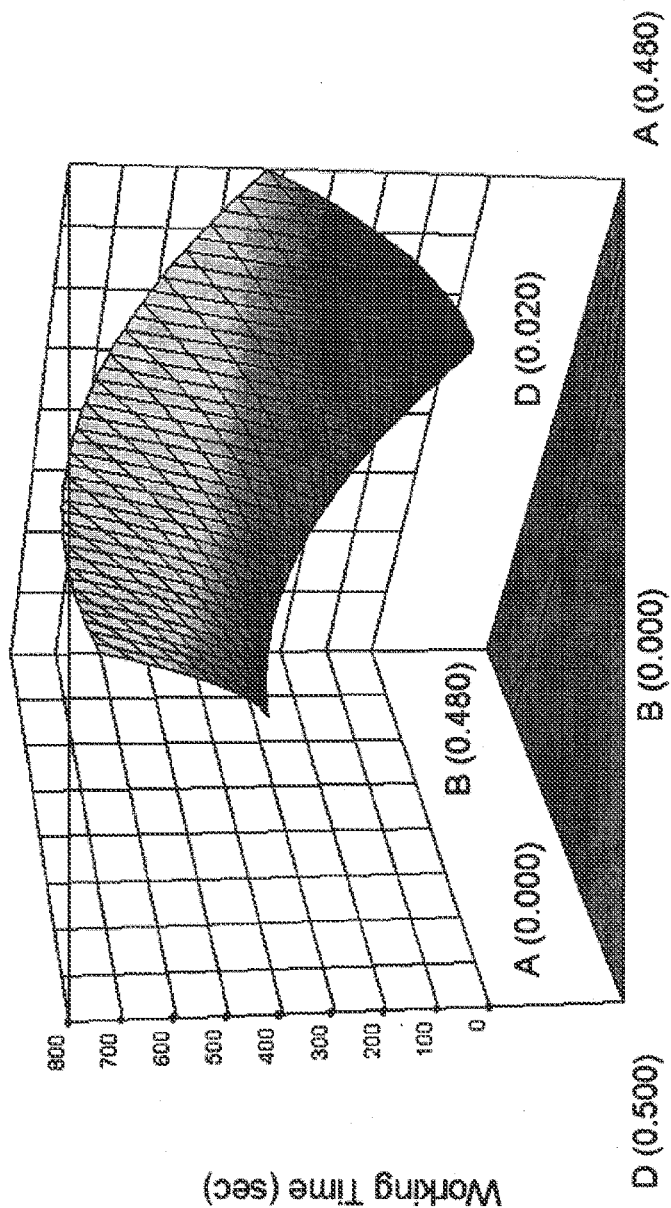
FIGS. 17A and B are 3D and 2D, respectively, contour plots illustrating the effect of varying glass composition on working time when varying $SiO_2$, CaO and $GeO_2$ compositions.
Figure 17B:
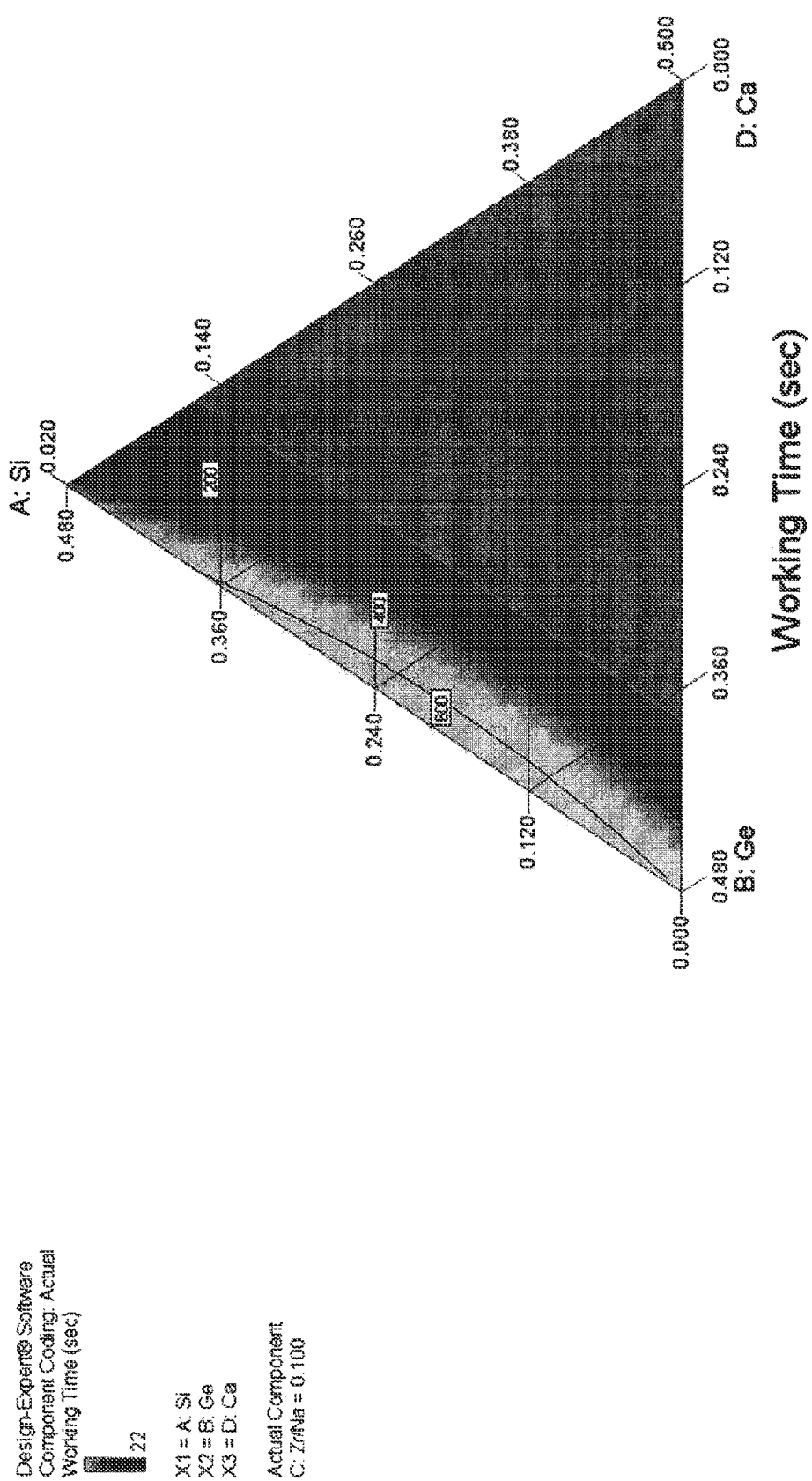
Figure 18A:
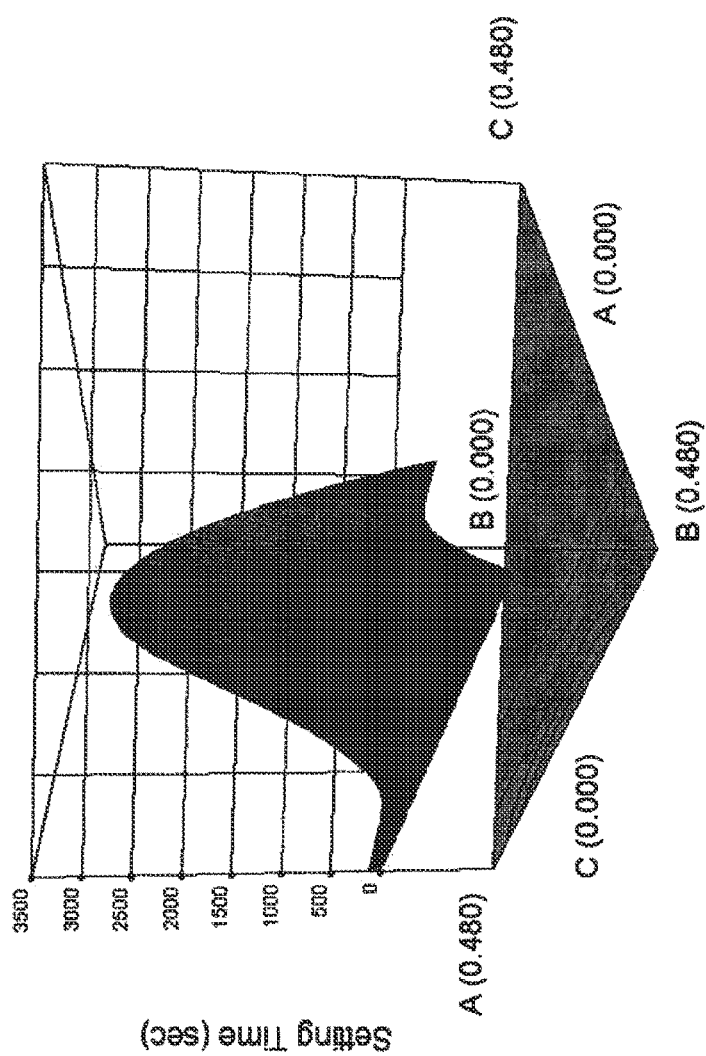
FIGS. 18A and B are 3D and 2D, respectively, contour plots illustrating the effect of varying glass composition on setting time when varying $SiO_2$, CaO and $ZrO_2/Na_2O$ compositions.
Figure 18B:
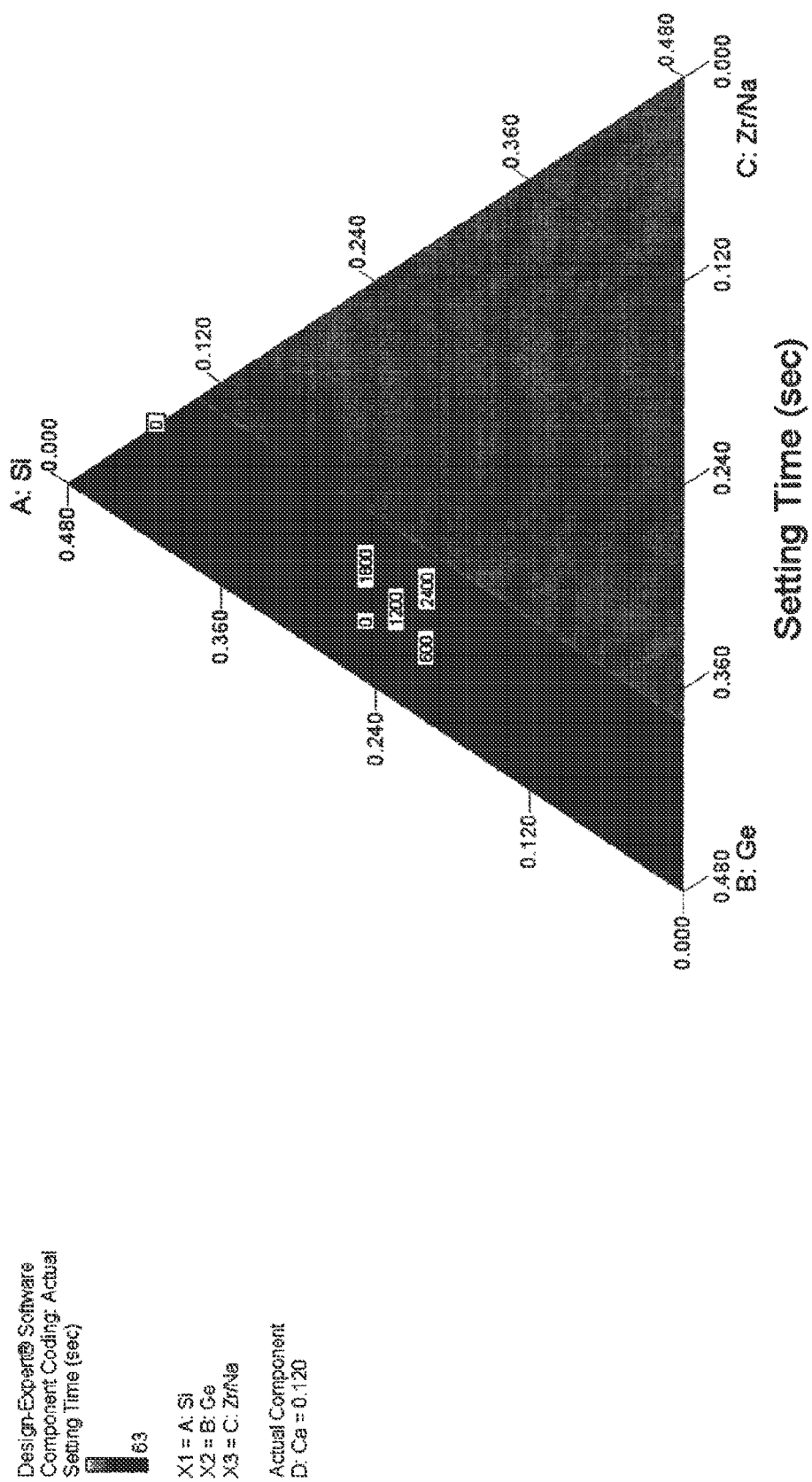
Figure 19A:
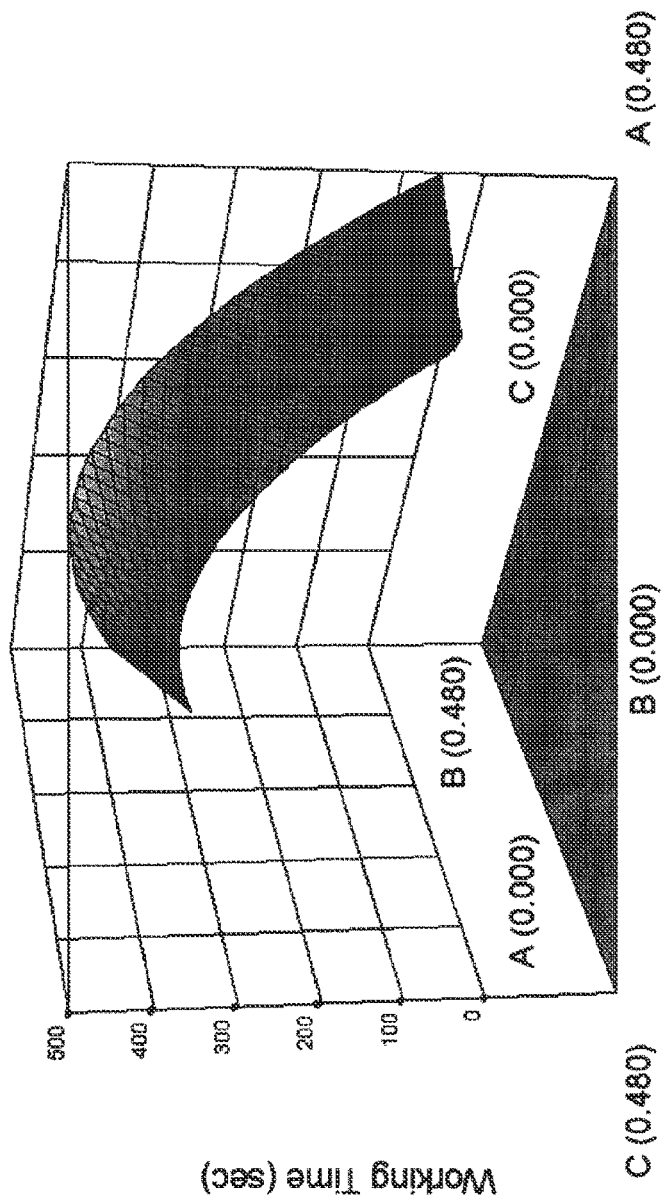
FIGS. 19A and B are 3D and 2D, respectively, contour plots illustrating the effect of varying glass composition on working time when varying $SiO_2$, CaO and $ZrO_2/Na_2O$ compositions.
Figure 19B:
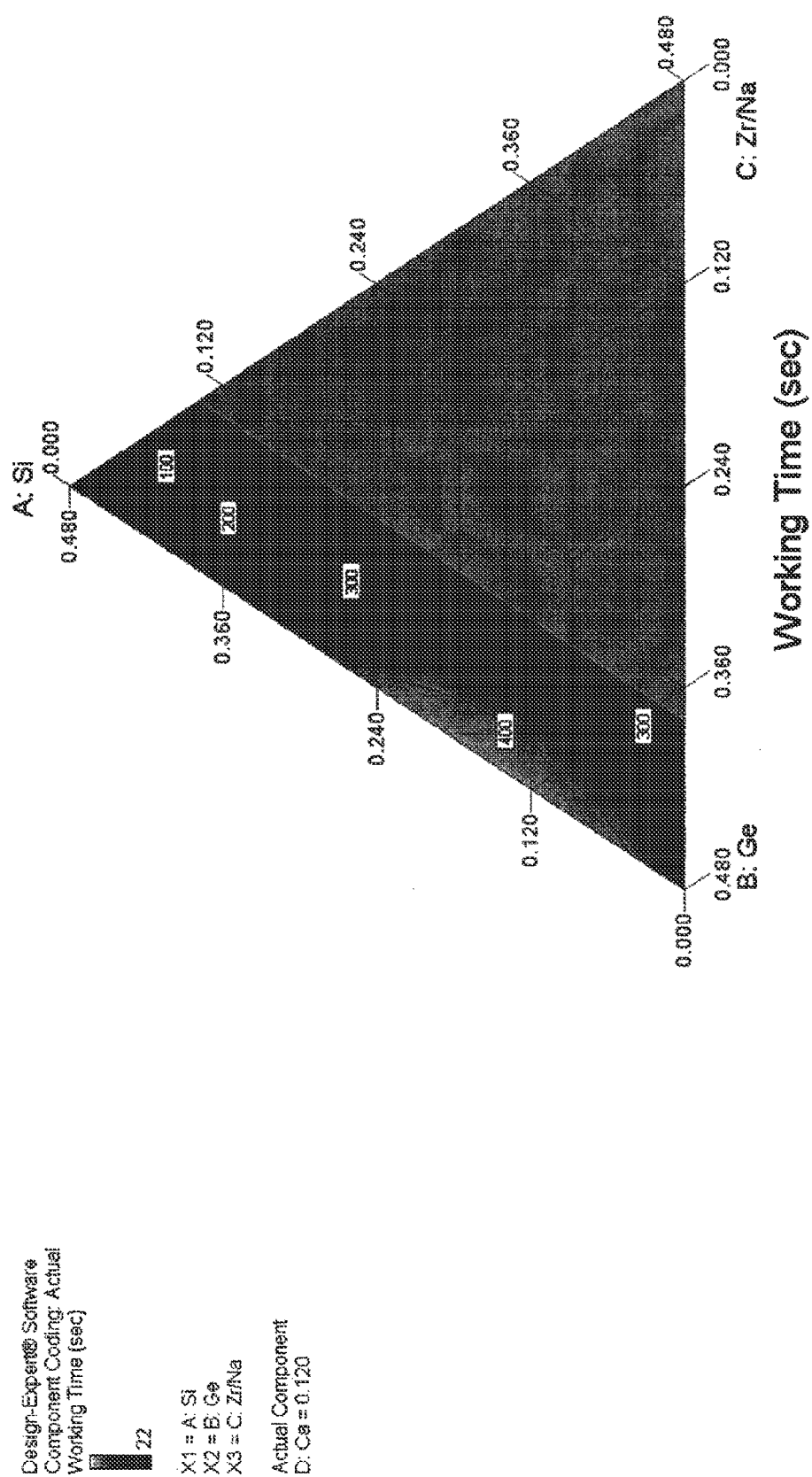

Each experiment is performed in triplicate and analysed using Prism 5.0 software (GraphPad software, Inc.) Results are expressed as mean±standard deviation of the triplicate determinations. One way analysis of variance (ANOVA) was carried out followed by a Tukey's post hoc test for comparisons between groups. The level of significance was set at $p<0.05$. Results are shown in Tables 4-6 and FIGS. 16-19. FIGS. 16A-B illustrate 3D (A) and 2D (B) contour plots show the effect of varying glass composition within the confines of the design space and the resultant setting time based on the regression model. These plots are confined to within the design space where component A $SiO_2$ varies from 0-0.48 mol fraction, component B $GeO_2$ varies from 0-0.48 mol. fraction, component D CaO varies from 0.02-0.12 mol. fraction, and $ZrO_2/Na_2O$ is fixed at 0.1 mol. fraction. FIGS. 17A-B illustrate the changes in working time based on the regression model for the same composition variations as FIGS. 16A-B. FIGS. 18A-B illustrate 3D (A) and 2D (B) contour plots show the effect of varying glass composition within the confines of the design space and the resultant setting time based on the regression model. These plots are confined to within the design space where component A $SiO_2$ varies from 0-0.48 mol fraction, component B $GeO_2$ varies from 0-0.48 mol. fraction, component C $ZrO_2/Na_2O$ varies from 0-0.10 mol. fraction, and CaO is fixed at 0.12 mol. fraction. FIGS. 19A-B illustrate the changes in working time based on the regression model for the same composition variations as FIGS. 18A-B.

TABLE 4A

Regression Equations in Terms of L Pseudo Components and R2 values and Summarized ANOVA for each Response.

| Response | Regression Model | $R^2$ | $R^2$ adj. | $R^2$ pred. | P Value | F |
|---|---|---|---|---|---|---|
| Working Time (sec) | +386.56 * $SiO_2$ +589.09 * $GeO_2$ +627.88 * $ZrO_2/Na_2O$ +7462.16 * CaO +1196.78 * $SiO_2$ * $GeO_2$ −10890.71 * $SiO_2$ * CaO −9956.51 * $GeO_2$ * CaO −13144.13 * $ZrO_2/Na_2O$ * CaO | 0.9872 | 0.9648 | 0.9240 | 0.0013 | 44.06 |
| Setting Time (sec) | +1568.67 * $SiO_2$ +2569.36 * $GeO_2$ +146.00 * $ZrO_2/Na_2O$ −6774.50 * CaO +2.797E+5 * $SiO_2$ * $GeO_2$ * $ZrO_2/Na_2O$ −1.262E+5 * $SiO_2$ * $GeO_2$ * CaO | 0.9168 | 0.8337 | 0.8056 | 0.0099 | 11.02 |

TABLE 4B

Working Time Regression Working Time Model for Actual Components as well as Additional Setting Time Model and an Exotherm Model

| | | Regression Model | $R^2$ | $R^2$adj. | $R^2$Pred. |
|---|---|---|---|---|---|
| Working Time | Actual | +885.11020 * $SiO_2$ +1194.26973 * $GeO_2$ +1435.14798 * $ZrO_2/Na_2O$ +12436.93684 * CaO +3557.61541 * $SiO_2$ * $GeO_2$ −32374.29770 * $SiO_2$ * CaO −29597.23618 * $GeO_2$ * CaO −39072.91707 * $ZrO_2/Na_2O$ * CaO | | | |
| Setting Time (sec) | L-pseudo | +9.03 * $SiO_2$ +6.14 * $GeO_2$ +79.33 * $ZrO_2/Na_2O$ −15.43 * CaO +12.25 * $SiO_2$ * $GeO_2$ −86.32 * $SiO_2$ * $ZrO_2/Na_2O$ −77.46 * $GeO_2$ * ZrO/NaO +31.34 * $GeO_2$ * CaO −102.50 * $ZrO_2/Na_2O$ * CaO | 0.9985 | 0.9927 | 0.7756 |
| Setting Time (sec) | Actual | +16.45604 * $SiO_2$ +9.61580 * $GeO_2$ +143.75249 * $ZrO_2/Na_2O$ −25.72152 * CaO | | | |

TABLE 4B-continued

Working Time Regression Working Time Model for Actual Components as well as Additional Setting Time Model and an Exotherm Model

| | Regression Model | $R^2$ | $R^2$adj. | $R^2$Pred. |
|---|---|---|---|---|
| | $+36.42894 * SiO_2 * GeO_2$<br>$-256.60109 * SiO_2 * ZrO_2/Na_2O$<br>$-230.25632 * GeO_2 * ZrO/NaO$<br>$+93.15426 * GeO_2 * CaO$<br>$-304.68341 * ZrO_2/Na_2O * CaO$ | | | |
| Exotherm (° C.) | L-pseudo | $+40.54 * SiO_2$<br>$+46.99 * GeO_2$<br>$+173.32 * ZrO_2/Na_2O$<br>$+41.92 * CaO$<br>$-31.26 * SiO_2 * GeO_2$<br>$-257.15 * SiO_2 * ZrO_2/Na_2O$<br>$-291.64 * GeO_2 * ZrO/NaO$<br>$-104.62 * GeO_2 * CaO$<br>$+271.51 * ZrO_2/Na_2O * CaO$ | 0.9950 | 0.9818 | 0.7104 |
| Exotherm (° C.) | Actual | $+67.48303 * SiO_2$<br>$+84.83687 * GeO_2$<br>$+280.27081 * ZrO_2/Na_2O$<br>$-69.86346 * CaO$<br>$-92.91738 * SiO_2 * GeO_2$<br>$-764.41338 * SiO_2 * ZrO_2/Na_2O$<br>$-866.94002 * GeO_2 * ZrO/NaO$<br>$-311.00507 * GeO_2 * CaO$<br>$+807.09738 * ZrO_2/Na_2O * CaO$ | | | |

TABLE 5

Abstracted ANOVA for the significant models (for working time (i), setting time (ii) and exotherm (iii)) investigated in this study.

| Source | Sum of Squares | df | Mean Square | F Value | p-value Prob > F | |
|---|---|---|---|---|---|---|
| (i) Working Time (WT) (sec) | | | | | | |
| Model | 3.436E+005 | 7 | 49083.18 | 44.06 | 0.0013 | significant |
| Linear Mixture | 2.779E+005 | 3 | 92635.29 | 83.16 | 0.0005 | |
| AB | 59574.54 | 1 | 59574.54 | 53.48 | 0.0019 | |
| AD | 6091.37 | 1 | 6091.37 | 5.47 | 0.0795 | |
| BD | 5091.16 | 1 | 5091.16 | 4.57 | 0.0993 | |
| CD | 7888.91 | 1 | 7888.91 | 7.08 | 0.0563 | |
| Residual | 4455.99 | 4 | 1114.00 | | | |
| Cor Total | 3.480E+0005 | 11 | | | | |
| (ii) Setting Time (ST) (sec) | | | | | | |
| Model | 21.09 | 8 | 2.64 | 171.25 | 0.00058 | significant |
| Linear Mixture | 10.91 | 3 | 3.64 | 236.15 | 0.0042 | |
| AB | 5.43 | 1 | 5.43 | 352.54 | 0.0028 | |
| AC | 0.38 | 1 | 0.382 | 4.56 | 0.0384 | |
| BC | 0.30 | 1 | 0.30 | 19.77 | 0.0470 | |
| BD | 1.19 | 1 | 1.19 | 77.23 | 0.0127 | |
| CD | 0.35 | 1 | 0.35 | 22.71 | 0.0413 | |
| Residual | 0.031 | 2 | 0.015 | | | |
| Cor Total | 21.12 | 10 | | | | |
| (iii) Exotherm (EX) (° C.) | | | | | | |
| Model | 325.04 | 8 | 40.63 | 75.10 | 0.0023 | significant |
| Linear Mixture | 212.07 | 3 | 70.69 | 130.67 | 0.0011 | |
| AB | 40.63 | 1 | 40.63 | 75.10 | 0.0032 | |
| AC | 3.39 | 1 | 3.39 | 6.27 | 0.0874 | |
| BC | 4.36 | 1 | 4.36 | 8.07 | 0.0656 | |
| BD | 43.49 | 1 | 43.49 | 80.40 | 0.0029 | |
| CD | 3.37 | 1 | 3.37 | 6.22 | 0.0881 | |
| Residual | 1.62 | 3 | 0.54 | | | |
| Cor Total | 326.67 | 11 | | | | |

WT-No AC, BC interactions
ST-No AD interaction
EX-No AD interaction

TABLE 6

Summary of the significant (positive and negative) main and interaction effects associated with the compositional factors (order of significant effects: highest to lowest, ↑ represents positive effects, and ↓ represents negative effects).

| Working Time (sec) | | Setting Time (sec) | | Exotherm (° C.) | |
|---|---|---|---|---|---|
| Ranking Order - Effect of Coefficient Component | Estimate Coefficient | Ranking Order - Effect of Coefficient Component | Estimate Coefficient | Ranking Order - Effect of Coefficient Component | Estimate Coefficient |
| ↓ ZrO/NaO * CaO | −13144.13 | ↓ ZrO/NaO * CaO | −102.50 | ↓ GeO * ZrO/NaO | −291.64 |
| ↓ SiO$_2$ * CaO | −10890.71 | ↓ SiO$_2$ * ZrO/NaO | −86.32 | ↑ ZrO/NaO * CaO | 271.51 |
| ↓ GeO * CaO | −9956.51 | ↑ ZrO/NaO | 79.33 | ↓ SiO$_2$ * ZrO/NaO | −257.15 |
| ↑ CaO | 7462.16 | ↓ GeO * ZrO/NaO | −77.46 | ↑ ZrO/NaO | 173.32 |
| ↑ SiO$_2$ * GeO | 1196.78 | ↑ GeO * CaO | 31.34 | ↓ GeO * CaO | −104.62 |
| ↑ ZrO/NaO | 627.88 | ↓ CaO | −15.43 | ↑ GeO | 46.99 |
| ↑ GeO | 598.09 | ↑ SiO$_2$ * GeO | 12.25 | ↑ CaO | 41.92 |
| ↑ SiO$_2$ | 386.56 | ↑ SiO$_2$ | 9.03 | ↑ SiO$_2$ | 40.54 |
| | | ↑ GeO | 6.14 | ↓ SiO$_2$ * GeO | −31.26 |

Example 9

Determination of Radiopacity of Cements

Figure 20:
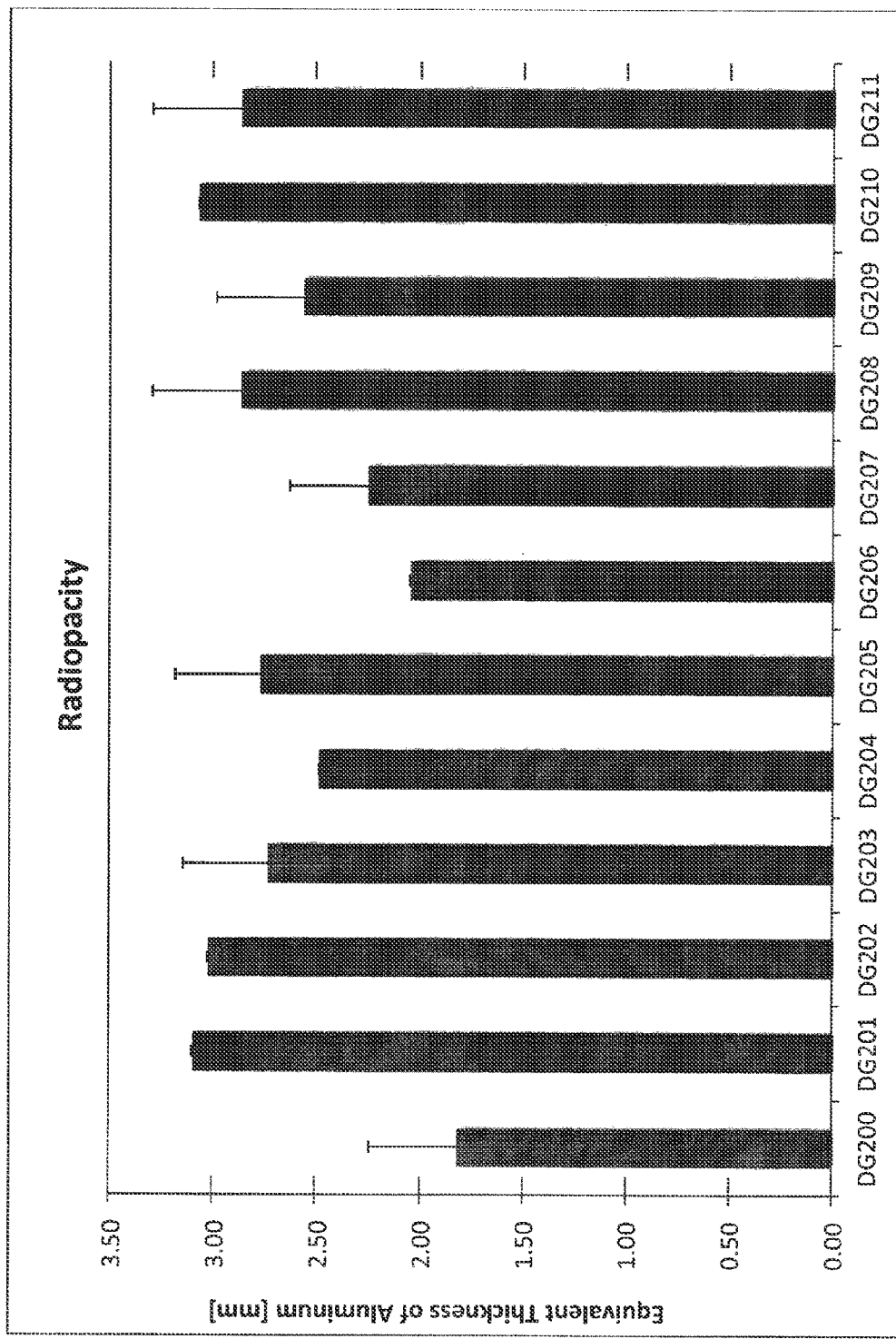
FIG. 20 illustrates results of radiopacity testing of GPC samples.

Radiopacity of the 12 cements was also calculated according ISO9917 (see reference 8). Cement batches were prepared and loaded into aluminum molds (Ø14 mm×1.7 mm) and each face was covered with acetate paper and the entire assembly was clamped and placed in an oven at 37° C. for 1 hour. The radiopacity of each material was determined by irradiating groups of 3 samples alongside an aluminum step wedge (12 steps, 1.3 mm to 12.6 mm thick) at a distance of 400 mm under 70 kV and 7 mA, using a Phot-X II x-ray source (Belmont Equipment, Somerset, N.J.). Specimens were exposed on Kodak Insight 10-41 dental film (Carestream Dental, Vaughan, ON). The optical density of each material and aluminum step was found using a QAS Densitometer (Picker International, Highland Heights, Ohio, USA). Each cements' equivalent aluminum thickness' was found by dividing the sample's thickness by the thickness of the aluminum step with an equivalent optical density. In instances where the density fell between two steps, the thicker step was taken, as per ISO 9917 procedure. FIG. 20 illustrates the average of four measurements for each sample. All samples exceed the ISO 9917 standard of 1 mm equivalent thickness of aluminum.

Example 10

In Vitro Compression Testing

Compression strength tests were conducted in accordance with ISO9917 (see reference 8). Cement (0.800 g glass, 0.300 g PAA, 0.300 mL H$_2$O) was mixed and loaded to excess into a stainless steel split mold with 5 cylinders (Ø 4 mm×6 mm) Prior to filling, the mold was coated with a silicon mold release spray to facilitate sample removal. The filled mold was clamped between two stainless steel plates with acetate paper to separate the cement from the plates. The clamped assembly was placed in an oven at 37° C. for 1 hour. Upon removal from the oven the assembly was broken down, cement flash was removed, and the ends of the samples were ground flat using wet 400 grit silicon carbide paper. The samples were removed from the molds and placed in plastic vials filled with 10 mL of distilled water. Vials containing the specimens were incubated in an oven at 37° C. for 1, 7, 30 and 180 days. In total 240 samples were produced, 5 specimens for each of the 12 cement types for 4 different incubation periods.

Figure 21:
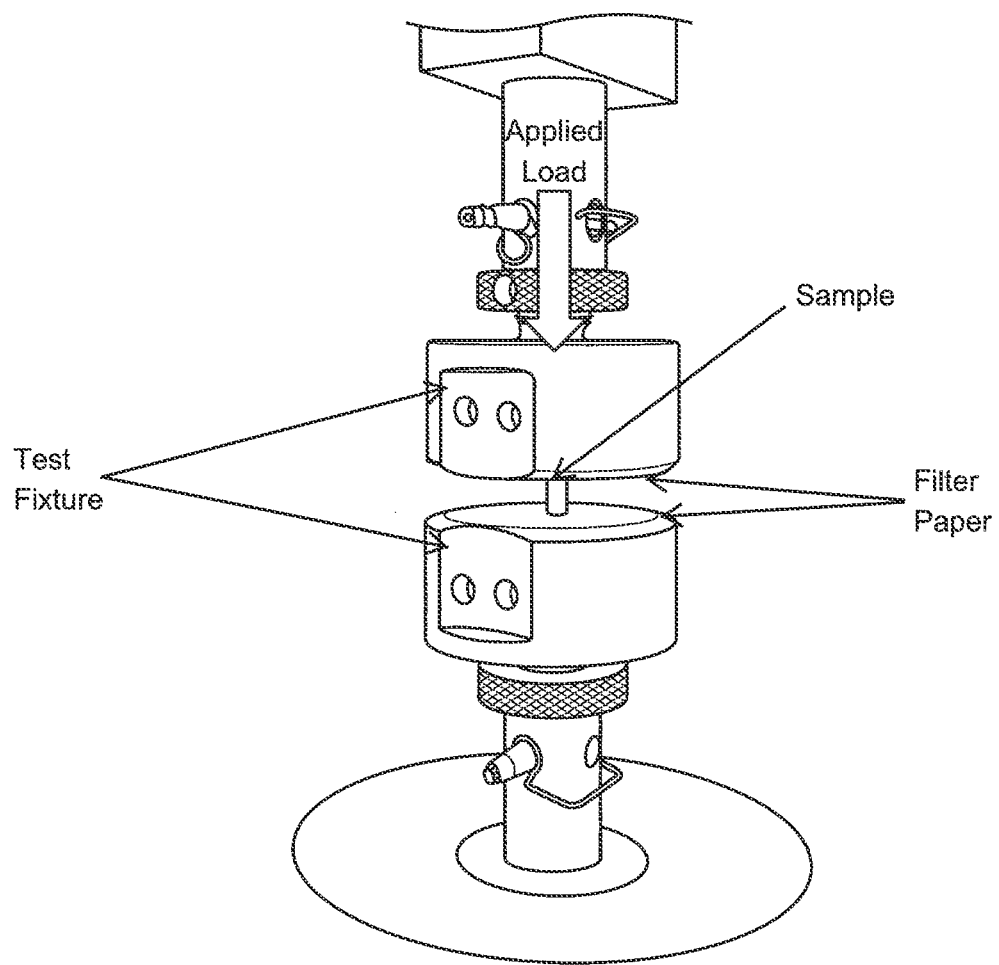
FIG. 21 illustrates an experimental set-up for compression testing of GPC samples.
Figure 22:
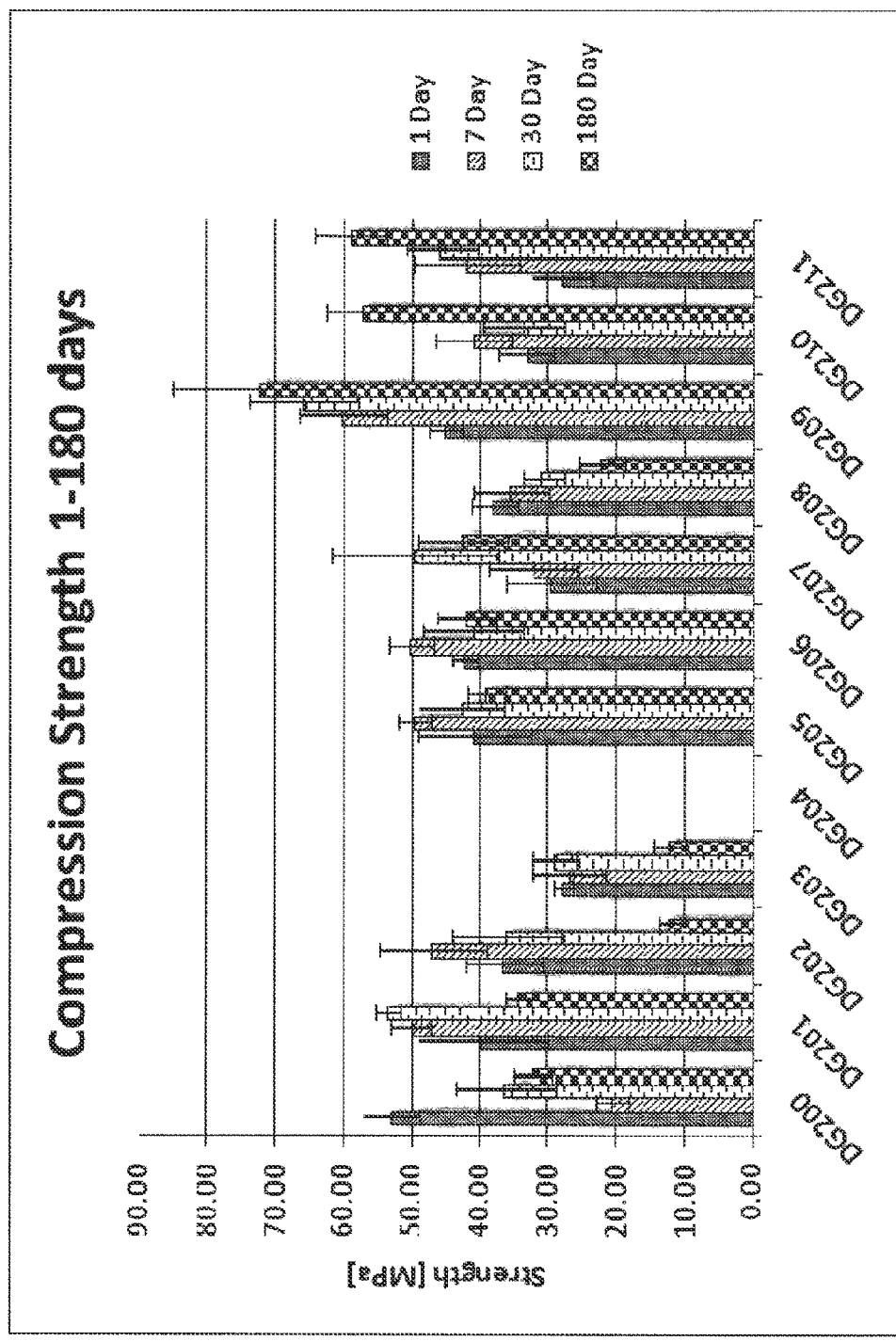
FIG. 22 illustrates compression strength experiments of GPC samples after 1, 7, 30, and 180 days.

Compression testing was conducted using an Instron 3344 mechanical testing system (Instron, Norwood, Mass., USA) with a 2 kN load cell. Samples were removed from water and their diameters (d$_c$) were measured using digital calibers, taken as the average of two measurements to the nearest 0.01 mm, 90° apart. Specimens were coaxially positioned in the test fixture between two pieces of damp filter paper (see FIG. 21). Specimens were crushed at a crosshead speed of 1 mm/min. Load-displacement data was recorded with Bluehill 2 (v2.25) software (Instron, Norwood, Mass., USA). Compression strength ($\sigma_c$) was calculated by $\sigma_c = 4P/\pi d_c$, where P was the maximum load at fracture (N). Compression strength results after 1, 7, 30 and 180 day incubation periods are shown in FIG. 22. The compressive strength of comparable aluminum-free GPCs is 30 to 50 MPa.

Example 11

In Vitro Biaxial Flexural and Biaxial Flexural Modulus Testing

Cement (0.500 g glass, 0.188 g PAA, 0.188 mL H$_2$O) was mixed and loaded to excess into a Teflon mold (Ø 15 mm×1 mm) The filled mold was clamped between two stainless steel plates with acetate paper to separate the cement from the plates. The clamped assembly was placed in an oven at 37° C. for 1 hour. Upon removal from the oven the assembly was broken down, cement flash was removed, and the ends of the samples were ground flat using wet 400 grit silicon carbide paper. The samples were removed from the molds and placed in plastic vials filled with 10 mL of distilled water. Vials containing the specimens were incubated in an oven at 37° C. for 1, 7, 30 and 180 days.

Figure 23:
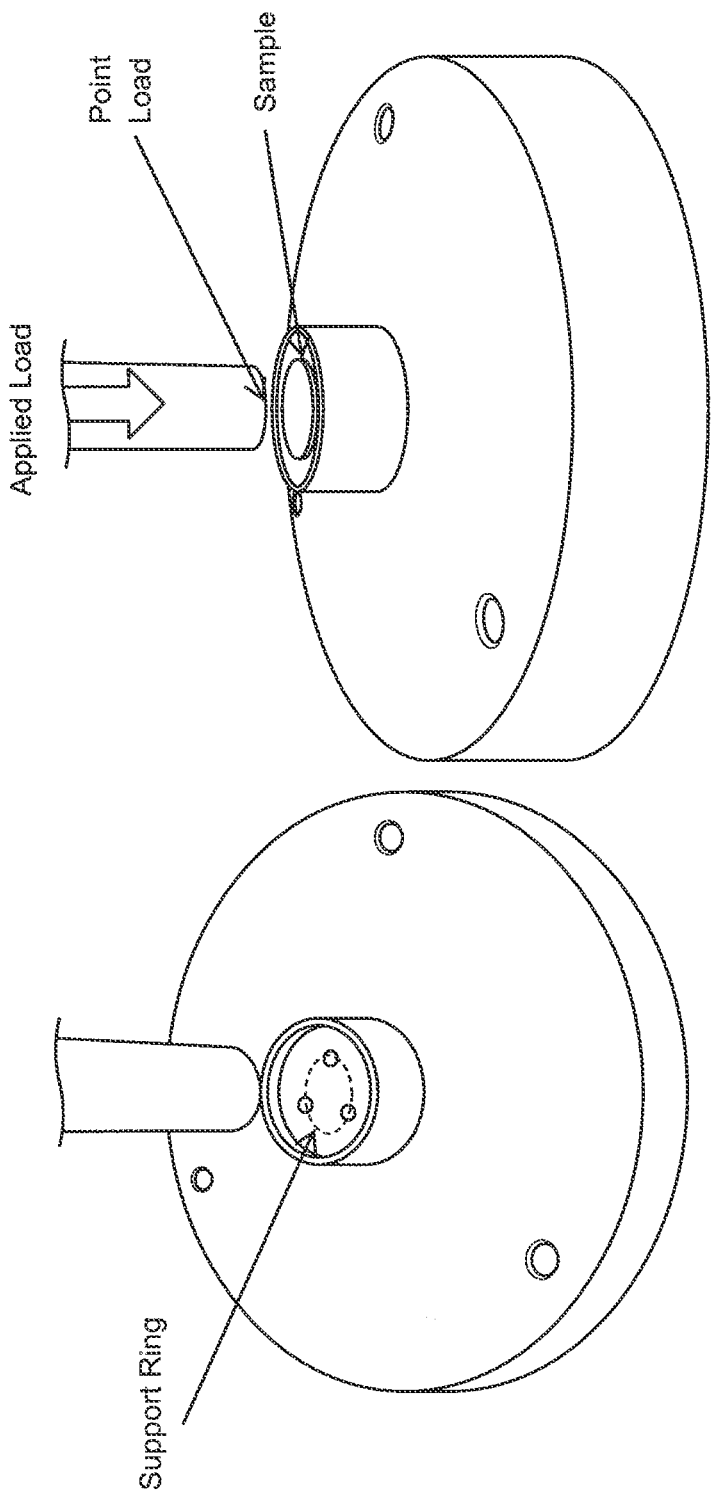
FIG. 23 illustrates an experimental set-up for biaxial flexural and biaxial flexural modulus testing.

Biaxial flexural testing was conducted similar to Williams et al. (see reference 9) and used an Instron 3344 mechanical testing system with a 2 kN load cell, fitted with a biaxial flexural test fixture (see FIG. 23). The biaxial flexural test fixture was designed according to ISO6872 (see reference 11), and modified for use with the equations described by Williams et al. (see reference 9), which employ point load from a ball bearing instead of a flat load from a pin. It consists of three 3 mm steel ball bearings arranged to form a support ring (Ø 11 mm), and a piston with a 3 mm ball bearing to provide a point load. Samples were removed from water and their diameters ($d_f$) were measured using digital calibers, taken as the average of two measurements to the nearest 0.01 mm, 90° apart. Specimens were coaxially positioned in the center of the test fixture and a loaded at a crosshead speed of 1 mm min$^{-1}$ Upon fracture, specimen fragments were removed and the thickness (t) at the fracture site was recorded. Load-displacement data was recorded with Bluehill 2 software. Biaxial flexural strength ($\sigma_f$) was calculated using:

$$\sigma_f = Pt^2\left[(1+v)\left(0.485\ln\left(\frac{r}{t}\right) + 0.52\right) + 0.48\right]$$

Where v is the poisson's ratio of the cement and r is the radius of the support diameter. When v=0.3, the equation becomes:

$$\sigma_f = Pt^2\left[0.63\ln\left(\frac{r}{t}\right) + 1.156\right]$$

Figure 24:
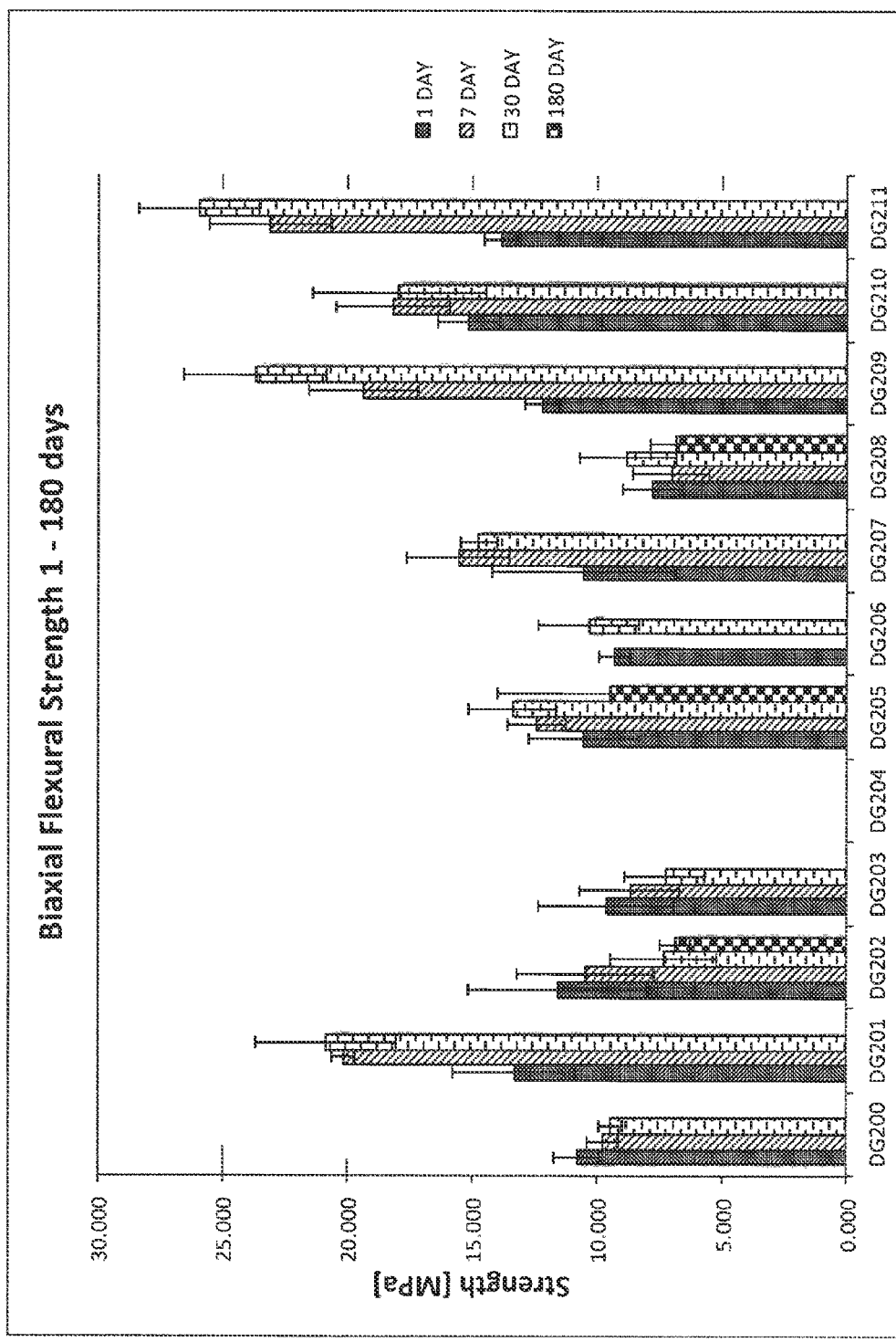
FIG. 24 illustrates the results of biaxial flexural strength experiments of GPC samples for 1-180 days.

The biaxial flexural strength measured at 1, 7, 30 and 180 days is shown in FIG. 24. As can be seen these are similar to those of comparable aluminum-free GPCs known—6-11 MPa.

Biaxial flexural modulus (E) is calculated using a method produced by Higgs et al. (see reference 10) after 1, 7, 30 and 180 days of incubation. The data of each test was recorded and analyzed using Python 2.6.6.2 to determine the slope (S) of the load-displacement curve. This was used in then to calculate the modulus as follows:

$$E = S\frac{B_c r^2}{t^3}$$

$$B_c = -0.0642 - 2.1900\text{ m}^{-3} + (0.5687 + 3.254\text{ m}^{-3})(1-v^2) + \left[-0.3793 + 11.0513\text{ m}^{-3} + (0.5223 - 7.8535\text{ m}^{-3})(1-v^2)\right]\left(\frac{r}{r_f}\right)^3$$

Figure 25:
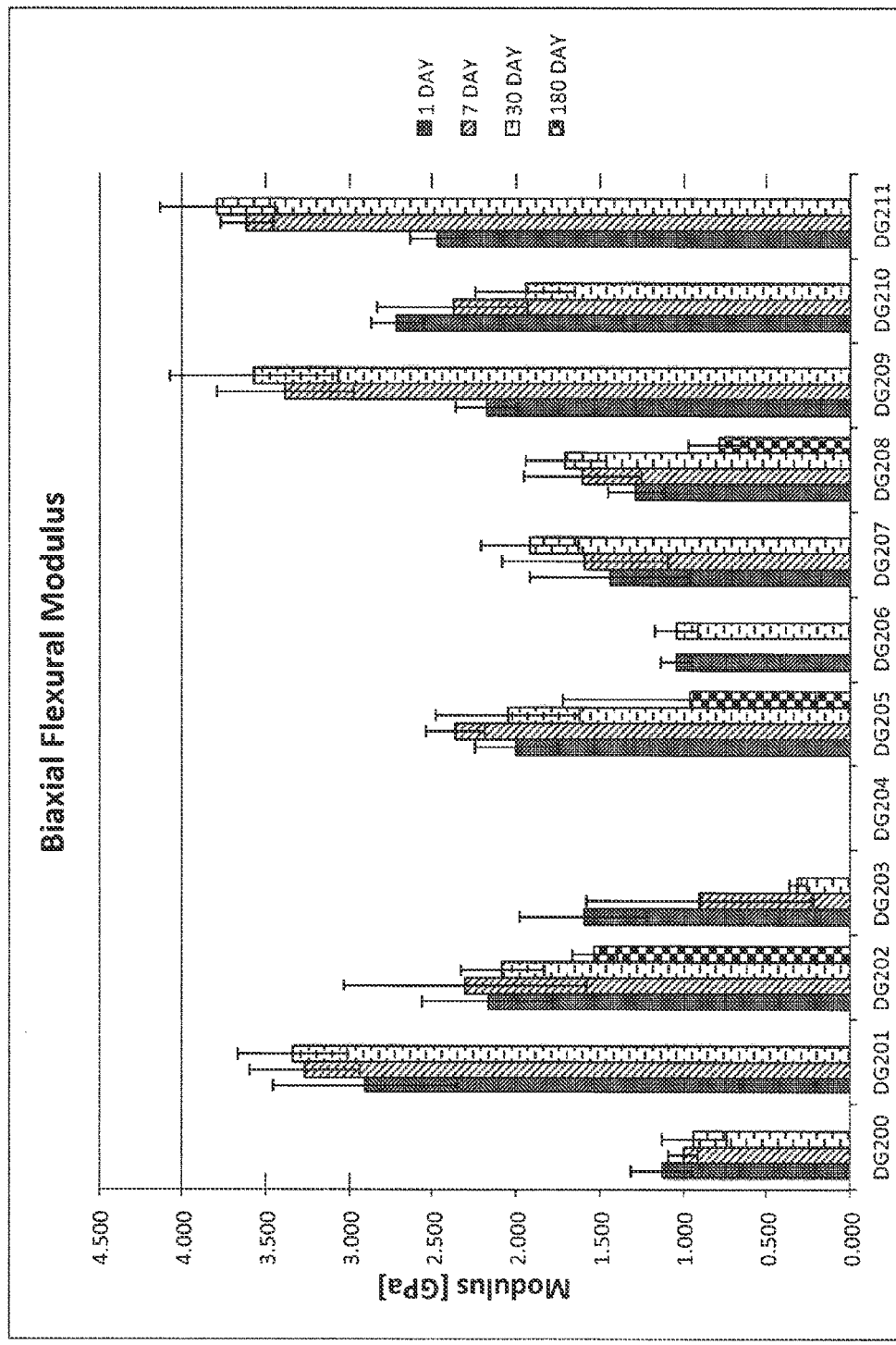
FIG. 25 illustrates biaxial flexural modulus data at 1-180 days.

$B_c$ is the center of deflection function and $r_f$ is the radius of the specimen. The modulus of each specimen was calculated and the average of which was biaxial flexural modulus of the material. The 180-day test was done for DG 202, DG 205 and DG 208. As can be seen from the results shown in FIG. 25, the sample GPCs are stiffer than known GPCs but comparable in stiffness to known alternative bone cements. The modulus range of alternative bone cements is 1200 to 1600 MPa and the modulus range for known GPCs is 100 to 500 MPa.

Example 12

Finite Element (FE) Analysis

Figure 26:
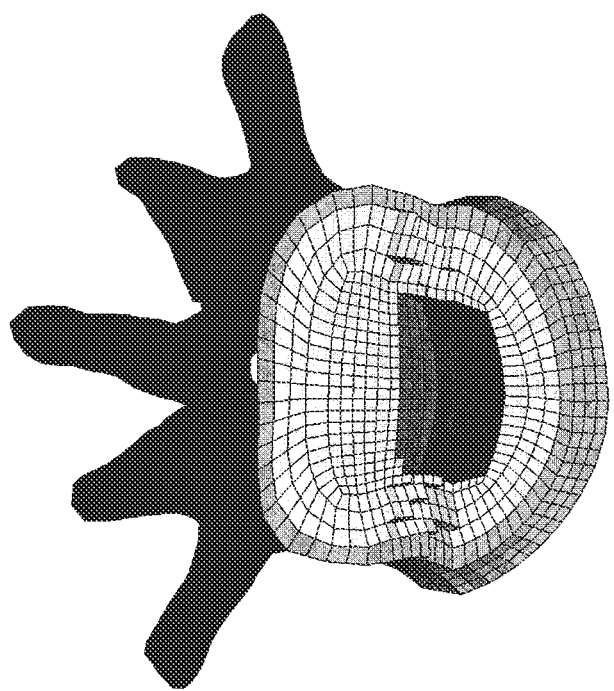
FIG. 26 illustrates a finite element model of a single augmented vertebra.

A FE model of a single vertebra under compressive load was used in this investigation. The vertebral FE model was previously published by Tyndyk et al. from computed tomography data, but modified for this investigation. Specifically, the model was simplified to isolate the L4 vertebra, consisting of the cortical bone shell, trabecular bone core, and vertebral arch complete with posterior elements (FIG. 26).

Figure 27:
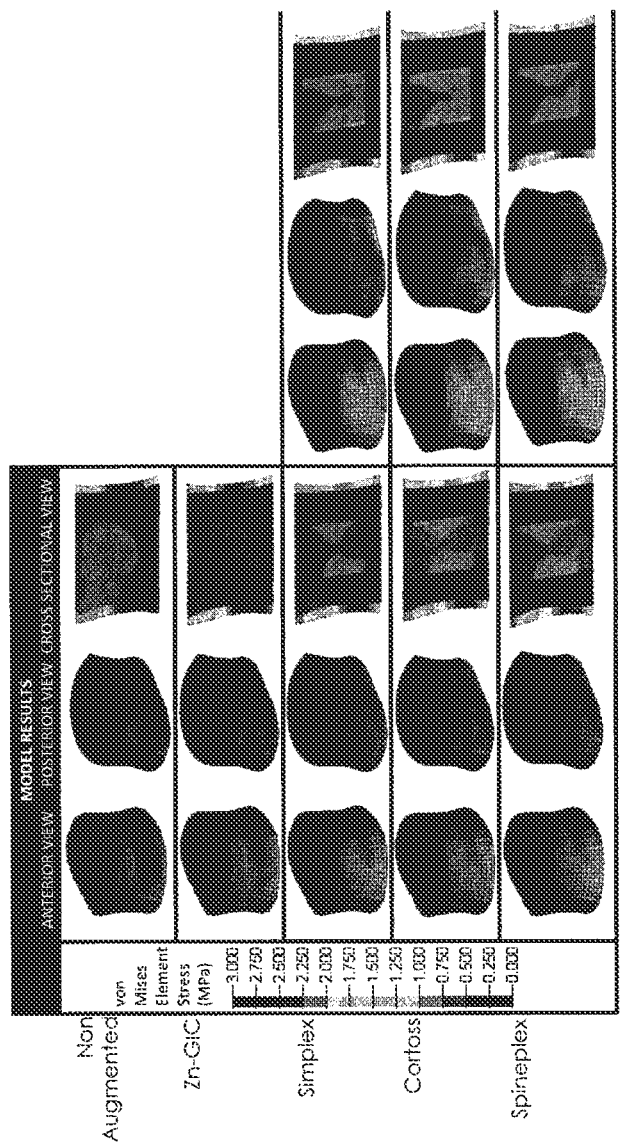
FIG. 27 illustrates solved finite element models for none augmented control, and augmented models with Zn-GPC, Simplex, Cortoss, Spineplex, DG202, DG205 and DG208.

Cement augmentation was represented as a vertically orientated barrel-like volume, located in the center of the trabecular bone, equivalent to approximately 16% of the volume of the vertebral. The model was built, and post-processing was completed using Altair Hyperworks 11.0 (Altair Engineering Canada Ltd., Toronto, Canada). The boundary conditions consisted of a uniformly distributed 1000 N axial compressive force across the top surface, and the bottom surface was fixed in all 6 degrees of freedom. These boundary conditions are used in literature pertaining to FE investigations of VP. Material properties of bone, and augmentation materials were taken from previously published data shown below in Table 7. FIG. 27 illustrates solved finite element models for none augmented control, and augmented models with Zn-GPC, Simplex, Cortoss, Spineplex, DG202, DG205 and DG208. The posterior elements have been hidden for clarity.

TABLE 7

| Component | Element Type | Material Properties E (MPa) | v |
|---|---|---|---|
| Cortical Bone | 8-node brick | 12000 | 0.3 |
| Trabecular Bone | 8-node brick | 344 | 0.2 |
| Posterior Elements | 4-node tetra | 3500 | 0.3 |
| Augmentation | 8-node brick | | |
| Zn-GPC | | 450 | 0.3 |
| Simplex P | | 1250 | 0.3 |
| Cortoss | | 1350 | 0.3 |
| Spineplex | | 1400 | 0.3 |
| DG202 | | 1900 | 0.3 |
| DG205 | | 2050 | 0.3 |
| DG208 | | 1700 | 0.3 |

Verification of the mesh was completed via a convergence study of von Mises stress in a specific location, yielding a model of 20,546 elements; with an average size of 1.4 mm. Tyndyk et al. experimentally validated the original model, and the current model was validated qualitatively by comparison with other models in the literature, showing good agreement with respect to magnitude and distribution of stress.

Figure 28:
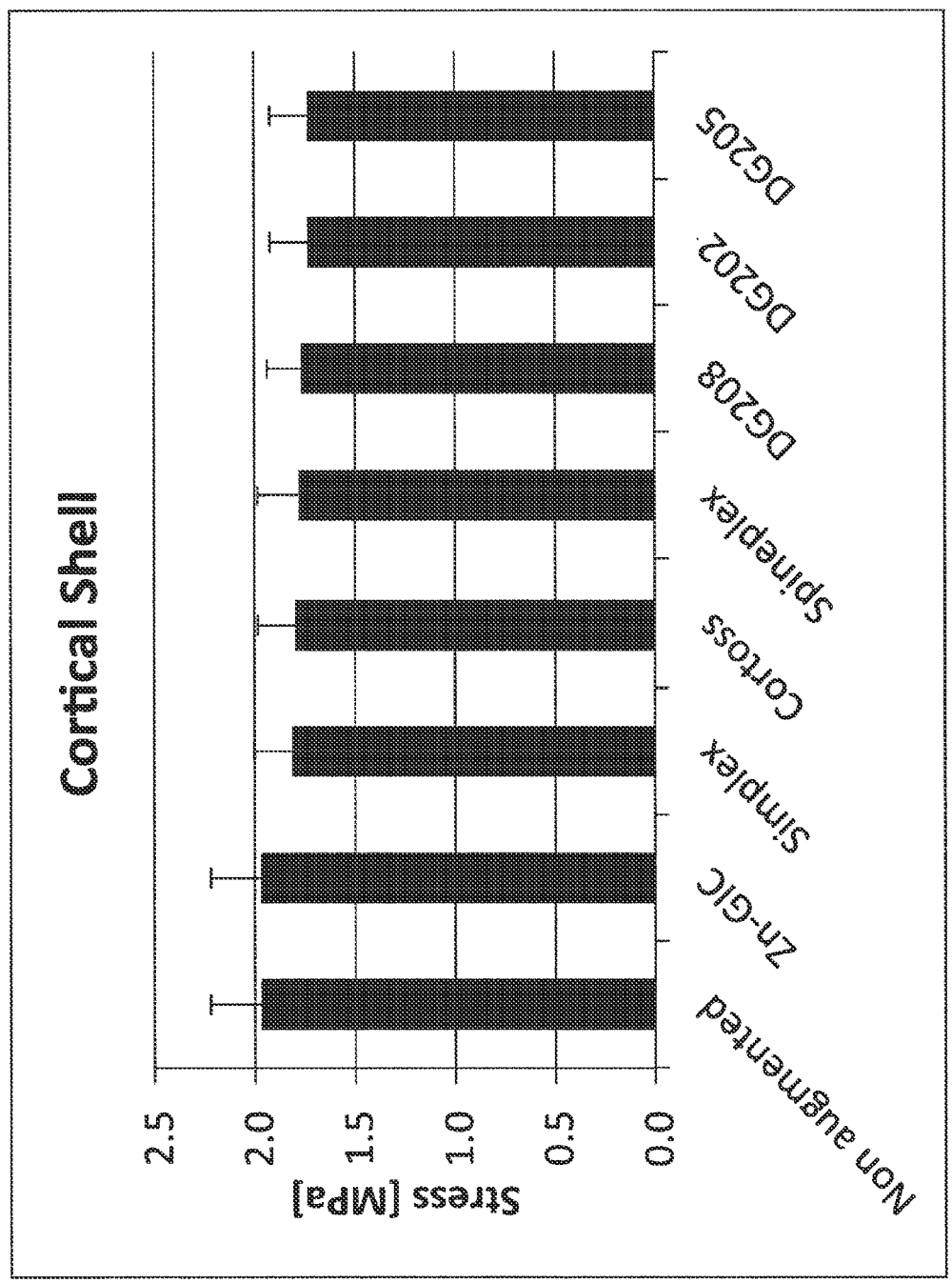
FIG. 28 illustrates average von Mises stress in cortical shell of the finite element model.
Figure 29:
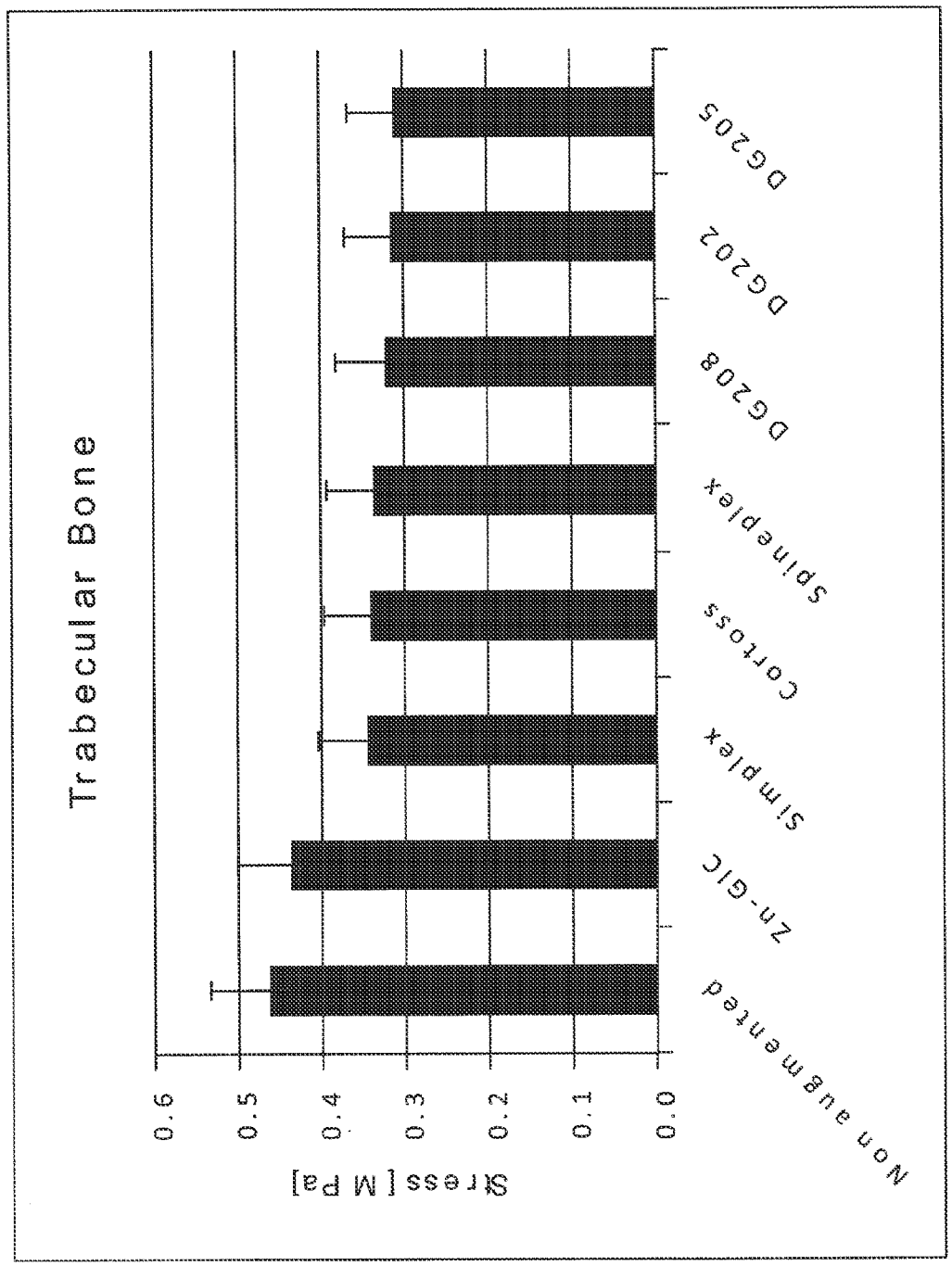
FIG. 29 illustrates average von Mises stress in trabecular bone in the finite element model.
Figure 30:
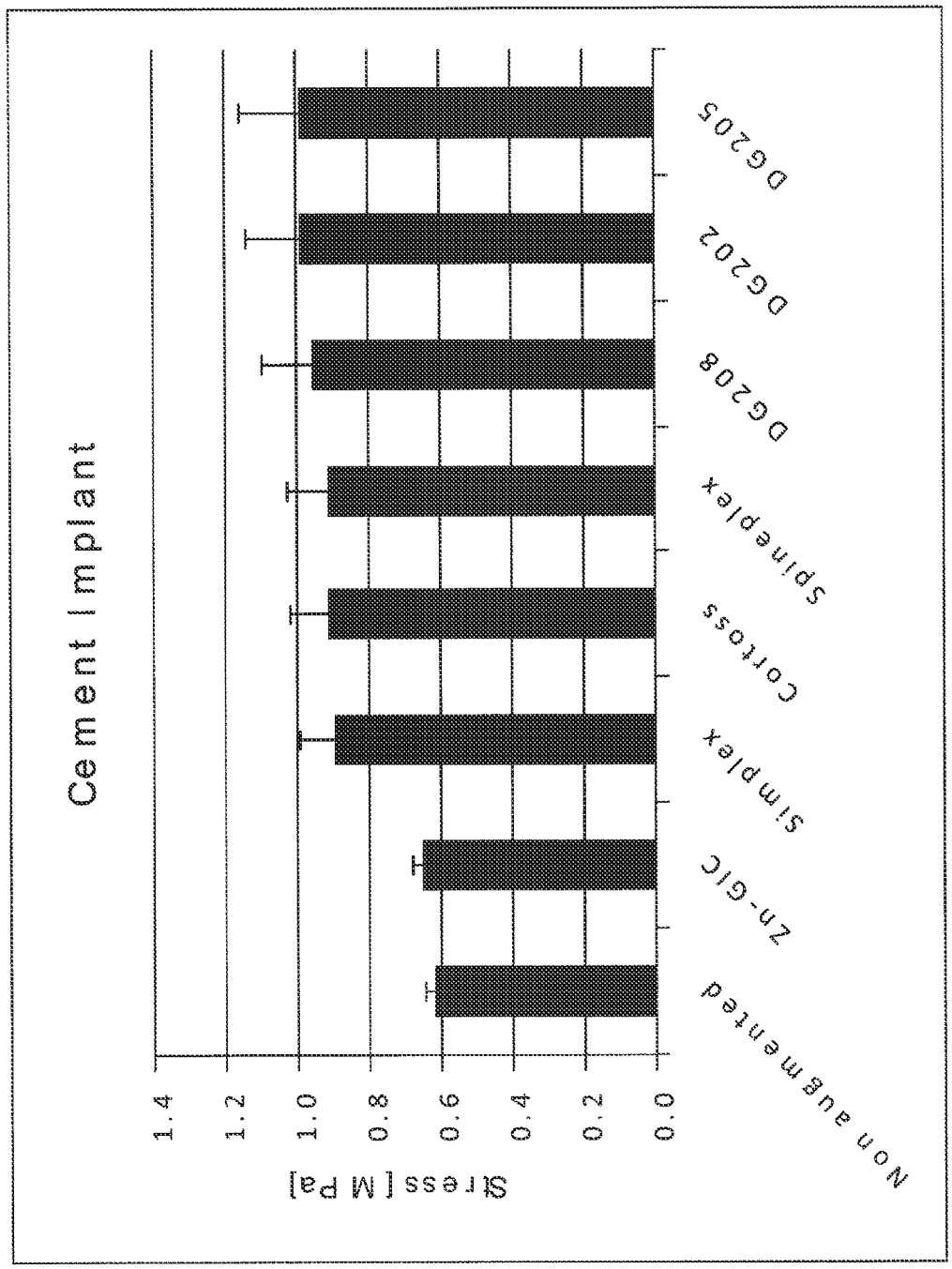
FIG. 30 illustrates average von Mises stress in the cement implant in the finite element model.

The model was used to produce data for healthy vertebra with each of the following seven implant materials; DG202, DG205, DG208, DG200, Simplex P®, Cortoss®, Spineplex® (clinically used, commercial materials, all of Stryker International), and non-augmented controls. The load scale of each run was adjusted to a lower limit of 0.00 MPa and an upper limit of 3.00 MPa (von Mises), the minimum stress range encompassing the results of all solved models, allowing for qualitative comparison of stress throughout the vertebral body between the different implant materials. Quantitative measurements were recorded for three regions: the cortical bone, the trabecular bone and the cement implant of both the healthy model. The model was sectioned along a transverse plane at half the height of the vertebral body and the stress of the exposed nodes across all three regions were recorded, averaged, and compared using ANOVA statistical analysis where p=0.01. The results are shown in FIGS. 28-30.

The results of the finite element analysis show the stiffer the cement material is, the more load is taken by the cement implant, and the cortical and trabecular bone take less. The stiffness of the DG series cements in increase order is: DG208<DG 202<DG205. The DG series materials have modulus greater than that of the zinc-silicate GPC (Zn-GPC), which results in significantly different load distribution within the vertebral body. The DG series cements' modulus is also greater than those of the commercial materials as well (Simplex, Cortoss, and Spineplex), however, DG208 produces statistically similar loading patters in the augmented vertebra as the commercial material Spineplex. DG202 and DG205 both produce statistically different loading patters compared to all three of the commercial materials. The important points of this data are the DG series cements are statistically different from the materials described in U.S. Pat. No. 7,981,972, yet comparable to current clinically used materials.

Example 12

In Vitro Biological Evaluation of Materials

Preparation of Material Extracts for In Vitro Analysis.

In vitro cytocompatibility as it pertains to each material (both DG series glass and DG series cement) is evaluated using the MTT assay with evaluations being on the basis of indirect exposure via the use of extracts.

Glass Extract Preparation.

0.1 grams of each glass powder measured to a precision of ±0.001 g with a Kern and Sohn GmbH analytical balance (model ABJ 120-4M) were transferred into 14 mL BD Falcon™ round bottom polypropylene tubes. The glasses were then vacuum autoclaved, in a Primus General Purpose Steam Sterilizer (Primus Sterilizer Company, Inc., Omaha, Nebr.) for 15 minutes at 121° C. Samples of each glass were prepared in triplicate for each of three incubation time periods: 24 hours, 7 days, and 30 days. 10 mL of tissue culture water (Sigma-Aldrich, lot # RNBB6914 and RNBC1419) were added aseptically to each sterilized glass sample, and the vials were capped tightly. Sample vials were positioned upright in 16 mm Nalgene® 5970 unwire test tube racks (Thermo Scientific) and incubated at 37.0 in a Julabo SW22 Shaking Water Bath (Julabo USA, Inc., Allentown, Pa.) with a uniaxial agitation rate of 2 Hz. At the completion of each incubation time period, samples were removed from the water bath and extracts were decanted aseptically into 0.2 micron filter syringes within a SterilGARD® III Advance class II biological safety cabinet. Filtrates were collected in sterile 14 mL polypropylene tubes, capped tightly and stored upright at 4.0 for later analysis.

Cement Extract Preparation.

Glass-ionomer cements were formed by mixing annealed glass powder with a 50% by weight aqueous solution of a 25,000 dalton poly(acrylic acid) in a powder:liquid ratio of 2:1.5. Cements were spatulated into Ø 7 mm×1 mm teflon disc molds, clamped between flat aluminum plates using screw vises, and allowed to set in a 37.0 ambient temperature environment for one hour. Following setting, cement discs were removed from the molds, and transferred into 14 mL BD Falcon™ round bottom polypropylene tubes. 10 mL of sterile tissue culture water were added to each cement sample. The remainder of the extract preparation procedure is identical to that used to prepare the glass extracts.

Fibroblast Cell Culture.

Immortalized mouse fibroblasts (NIH-3T3; American Type Tissue Collection, Manassas, Va.) at passages 15-20 were used for experiments. The cells were grown in 75-cm² tissue culture flasks in Dulbecco's Modified Eagle's Medium (DMEM) supplemented with 5% fetal calf serum (FCS; heat-inactivated at 56° C. for 60 min). Flasks were maintained in a humidified atmosphere at 37° C. and 10% $CO_2$. No antibiotics were used during routine subdivisions or for cell culture experiments to avoid altering cell metabolism. At confluency, the media was discarded and 1.5 mL of 0.25% trypsin EDTA solution (Sigma-Aldrich, USA, lot #1196474) were added to the cell culture flask then left for 5 to 10 minutes to detach the cells. 8.5 mL of DMEM-5% NCS was added to the trypsin-EDTA-cell solution. 1 mL of this solution was transferred into sterile culture flasks; 19 mL of fresh media was added to each and the diluted cells were incubated at 37° C. for growth and later use. (Cells were passaged weekly in this manner.) A sample of the remaining cell solution was analyzed for cell density using a Bright-line Hemocytometer (Hauser Scientific, Horsham, Pa.). A portion of the cell solution was diluted with DMEM-5% NCS solution for a resultant $1\times10^4$ cells per mL solution in preparation for immediate use.

Assessment of Cell Viability (MTT Assay).

NIH-3T3 cells (200 µL) are seeded at a density of $1\times10^4$ cells/mL in 96-well plates (CoStar, Corning, Canada). Cell laden culture media was used as a negative control, occupying one row of wells in each culture plate (n=12). Cell culture media in the absence of cells provided a blank control in one column of an additional 96 well plate (n=8). Seeded and blank plates were incubated at 37° C. for 24 hours. Following incubation, 20 µL of sterile tissue culture water were added to each control well, blank and negative alike, while 20 µL of sample extract were added to wells for cell viability testing. Each extract type was tested three times (n=3 extracts per condition) with a cell viability analysis of n=7 for each individual extract. The plates were incubated again for 24 hours at 37° C. 15 mL of 5 mg/mL 3-(4,5-dimethylthiazol-2-yl)-2,5-diphenyltetrazolium bromide (MTT) were prepared in pH 7.4, 0.01M phosphate buffer solution (Sigma-Aldrich USA, lot #028K8214) shielded with an aluminum foil covering, and stored at 4° C. Following the second 24 hour incubation of the plates, 22 µL of this MTT solution (an amount equivalent to 10% by volume of the well content) were added to each well. Samples were incubated for another 3 hours at 37° C. Liquid contents of the plates were then blotted onto towels, and 100 µL of dimethyl sulfoxide (DMSO, Sigma-Aldrich USA, lot #14196PMV) was added to each well of cells. Plates were shielded with aluminum foil and stirred on a rotating plate. Spectrophotometric optical density (absorption) values were read using a Bio-Tek™ Synergy HT plate reader equipped with KCF Kineticalc for Windows (Version 3.2, Rev. #2, BioTek Instruments, Inc.) A wavelength correction was performed at 977 and 900 nm; plates were read at 492 nm. Cell viability was calculated according to 2.1 (adapted from ISO 10993-5) in comparison with the negative control (seeded tissue culture water) which was set at 100% cell viability:

$$\text{Cell viability \%} = 100\%(OD492e/OD492c)$$

Wherein:
OD492e is the mean value of the measured optical density of experimental extract wells;
OD492c is the mean value of the measured optical density of negative control wells.

Figure 31:
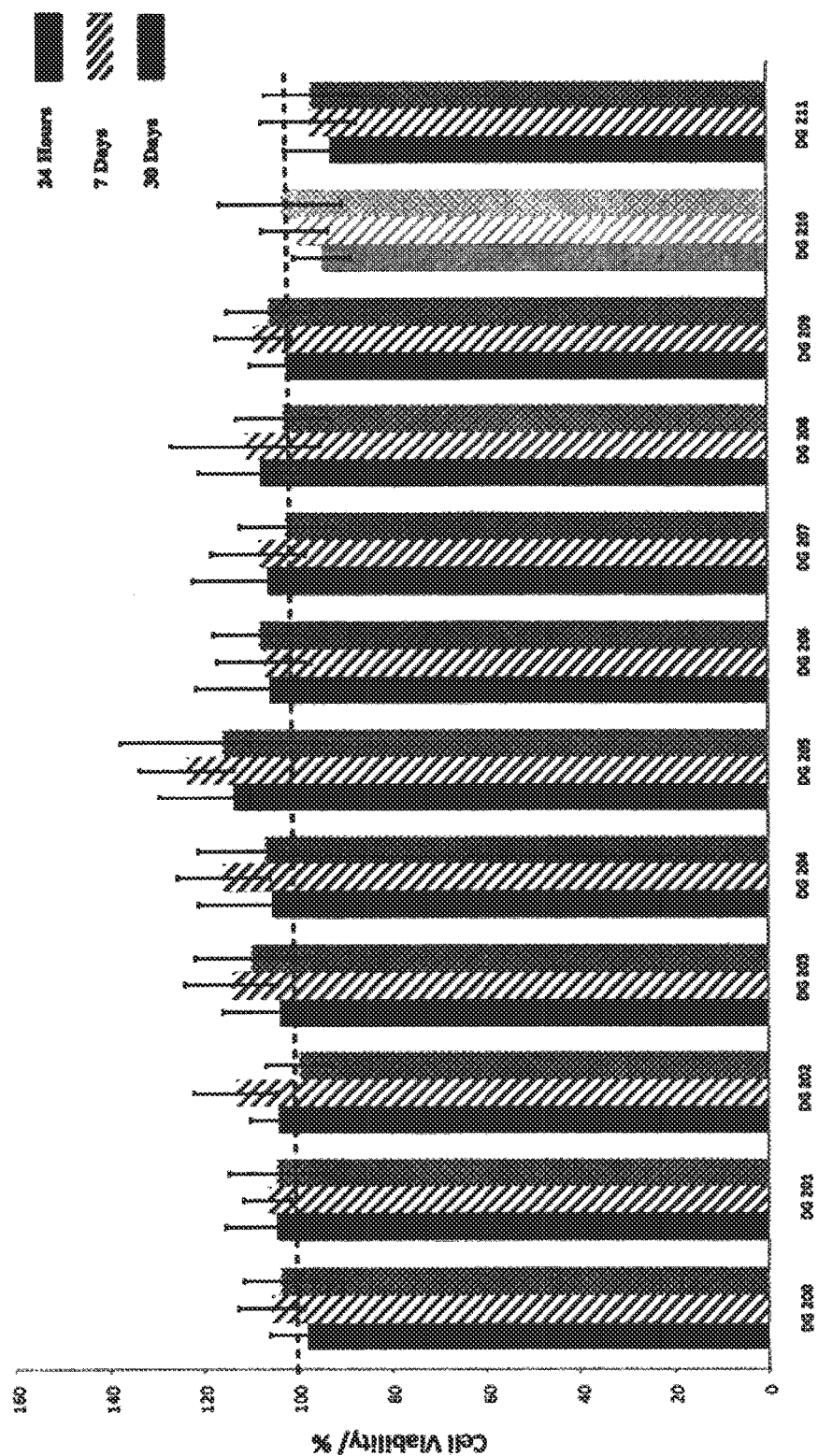
FIG. 31 illustrates MTT assay data.
Figure 32A:
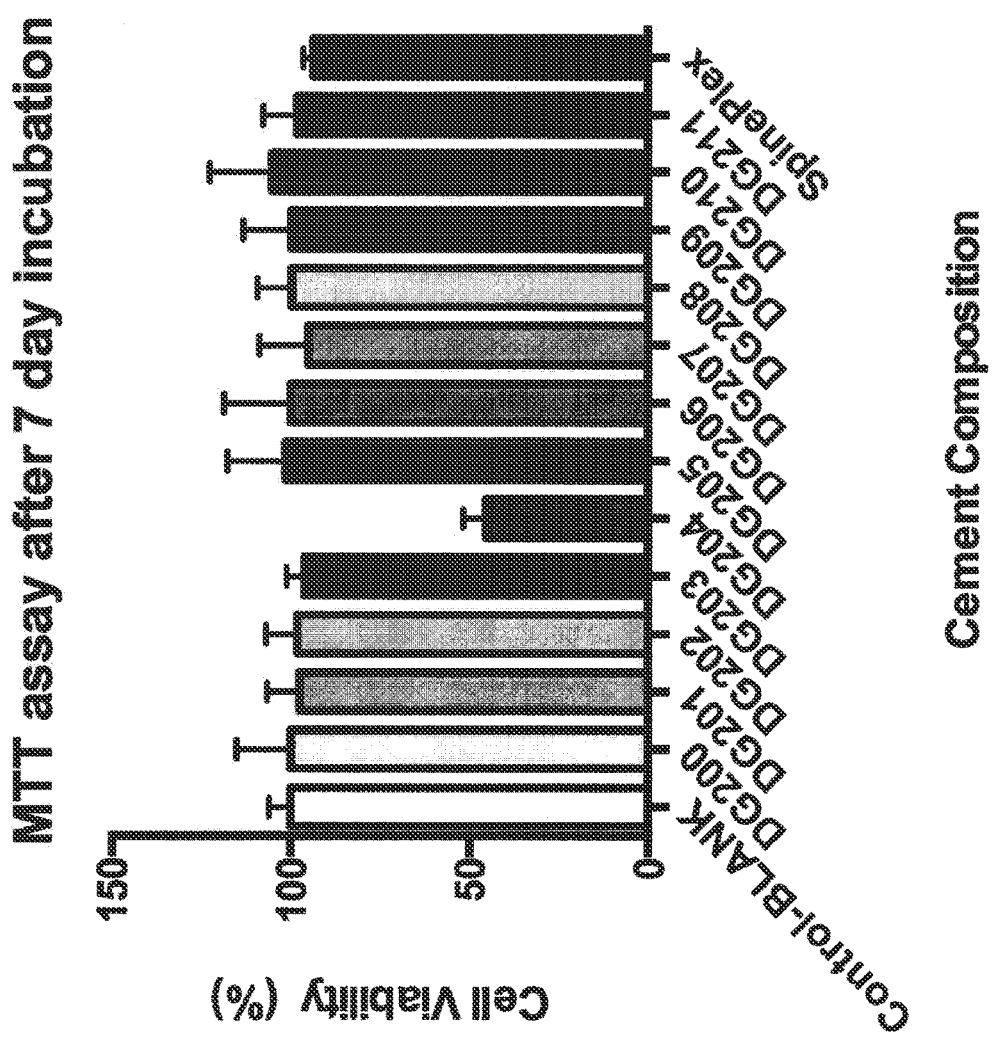
FIGS. 32A-C illustrates cell viability for 1, 7, and 30 day cement extracts.
Figure 32B:
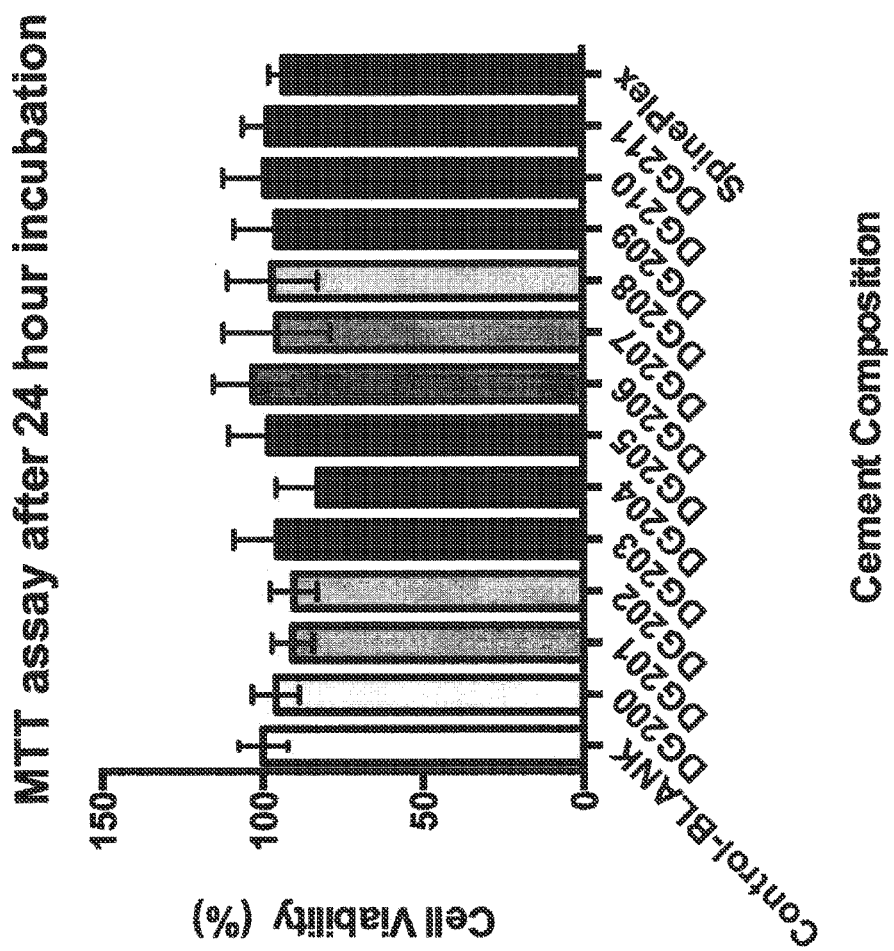
Figure 32C:
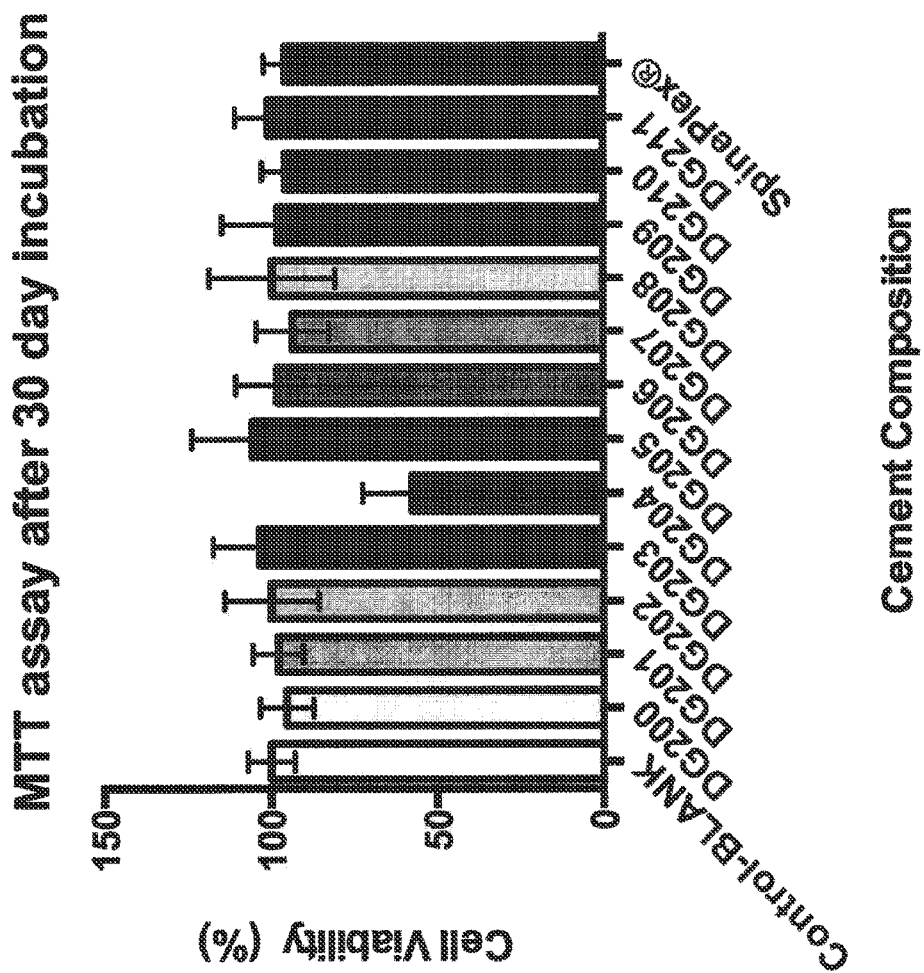
Figure 33A:
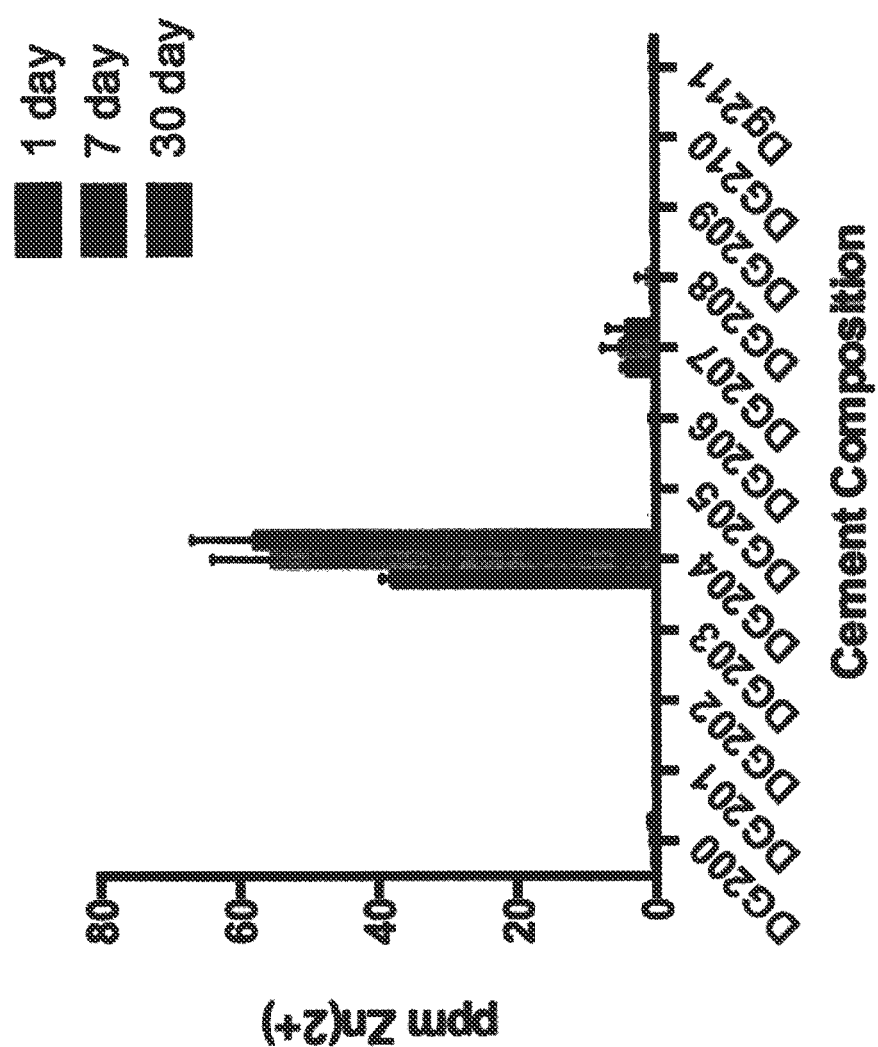
FIGS. 33A-D provide degradation data after 1, 7, and 30 days for cement extracts for Zn, Ge, Zr and Sr.
Figure 33B:
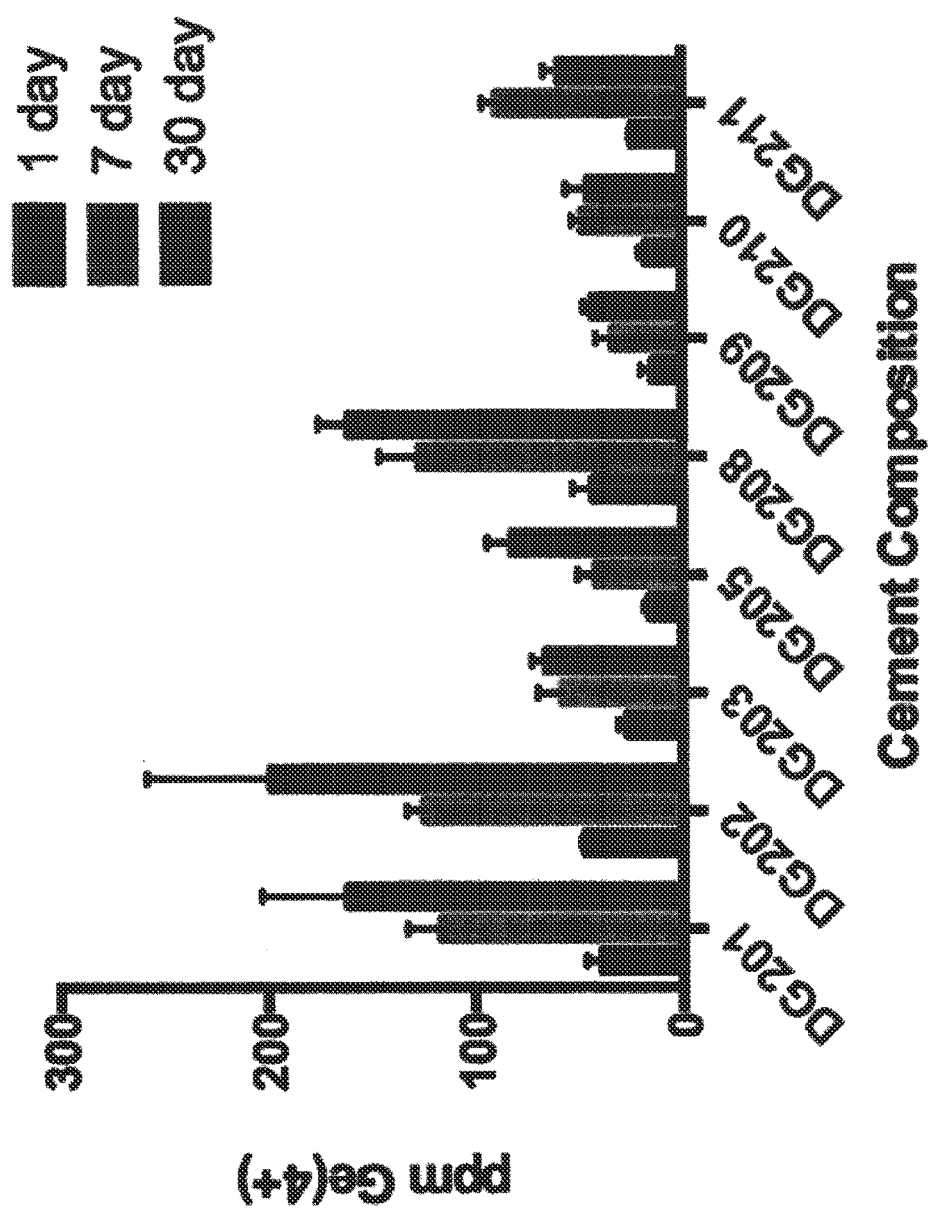
Figure 33C:
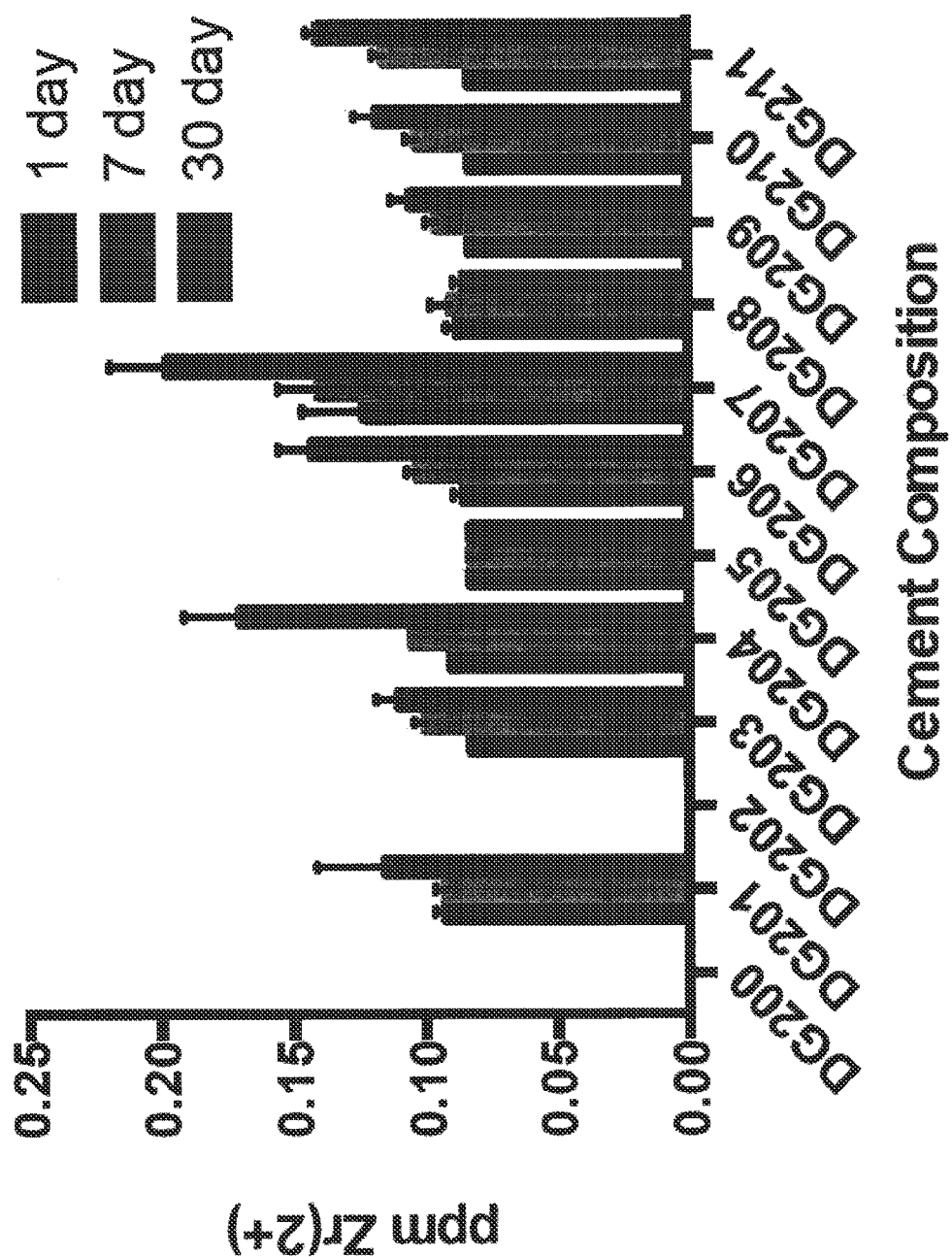
Figure 33D:
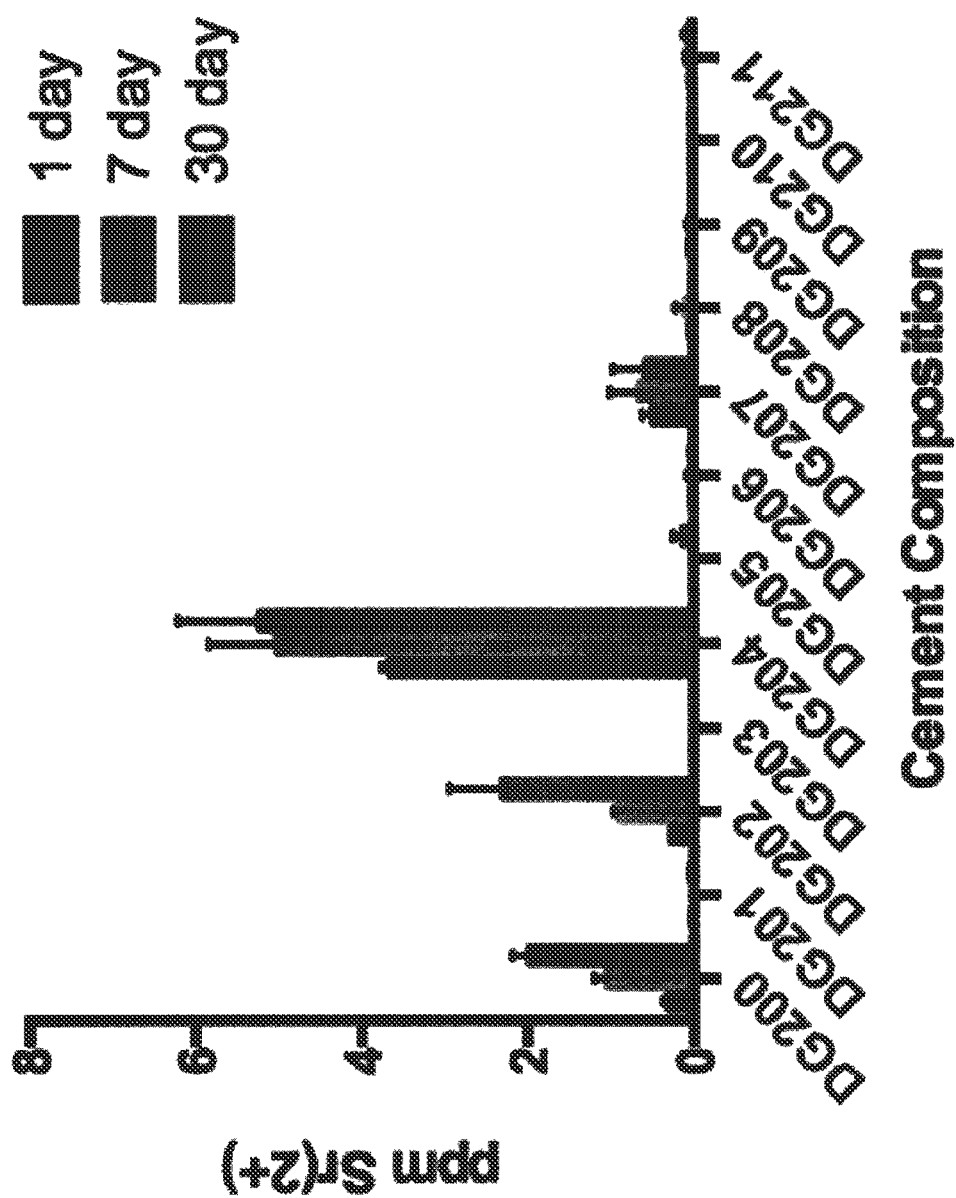

FIG. 31 demonstrates the viability test of glass extracts following incubation at 24 hours, 7 days, and 30 day, as compared with a seeded cell culture water negative control set at 100% viability. All tested cements demonstrated high cell viability. FIGS. 32A-C demonstrate viability of the cement extracts after 24 hours, 7 days and 30 days.

Degradation Product Analysis.

Figure 34A:
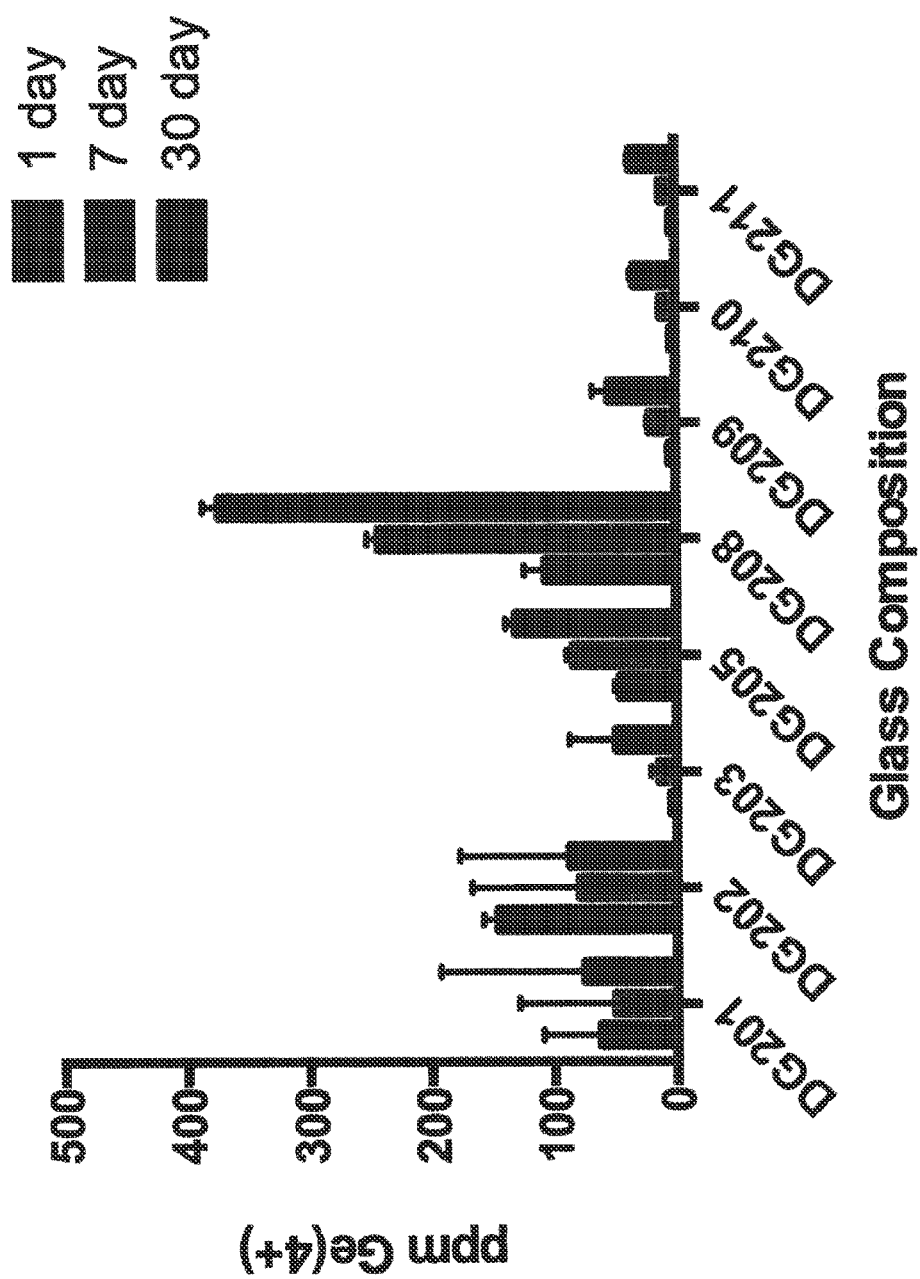
FIGS. 34A-C provide degradation data after 1, 7, and 30 days for glass extracts for Ge, Sr and Zn.
Figure 34B:
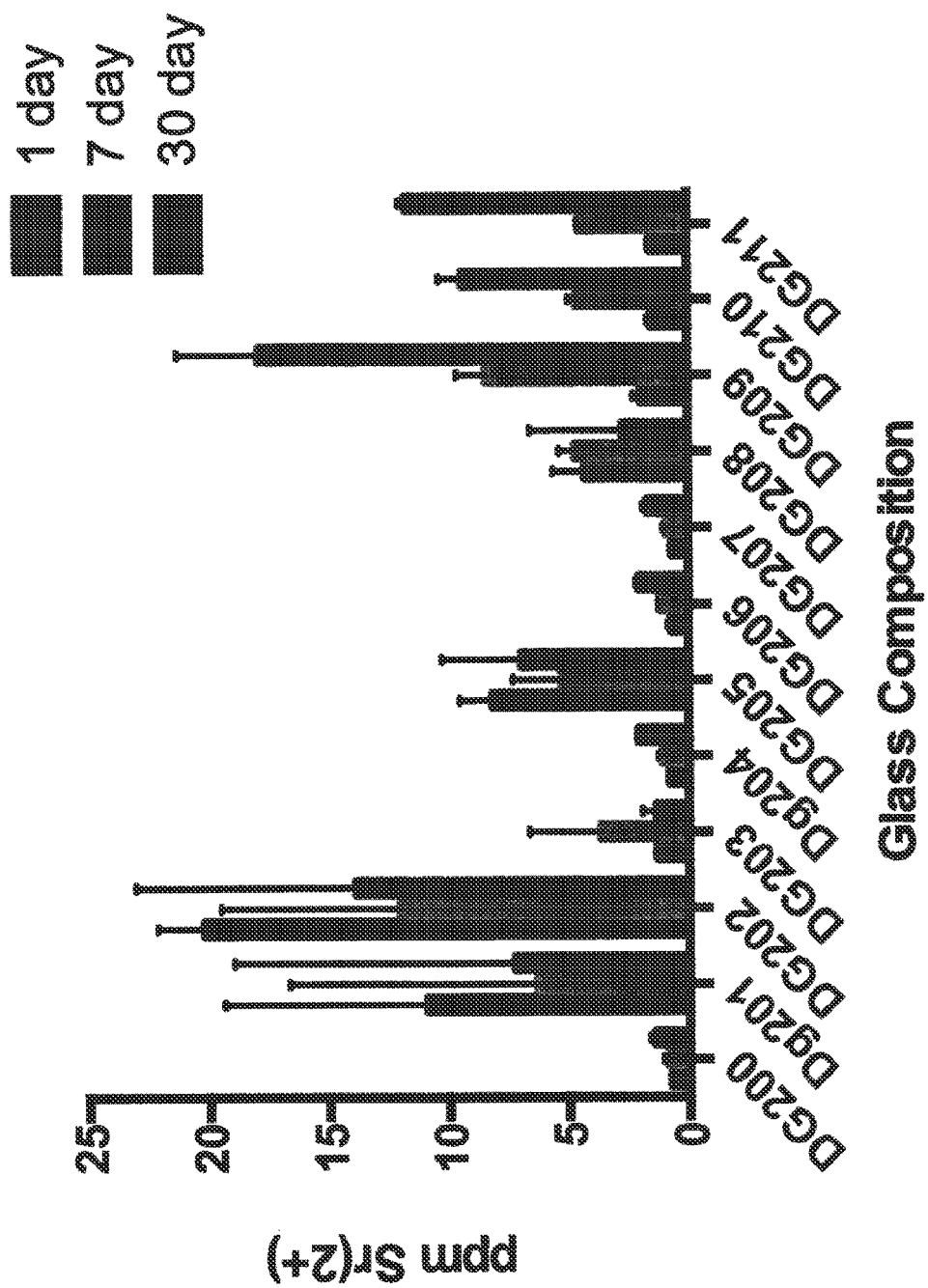
Figure 34C:
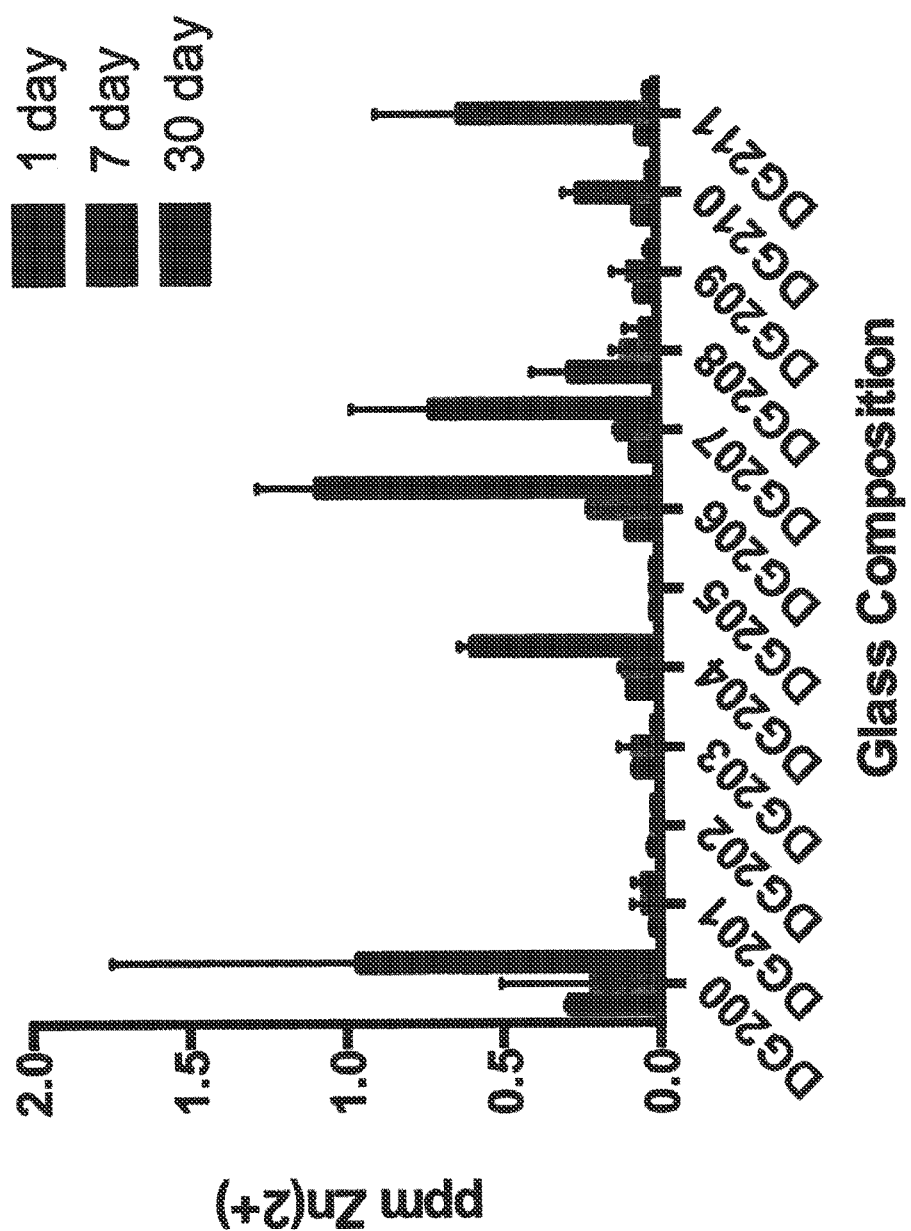

1 mL of each of the glass and cement extracts was diluted up to 7.5 mL with 2% (v/v) $HNO_3$. Calibration standards were prepared analytically in concentrations ranging from 0.001 mg/L to 50 mg/L in 2% (v/v) $HNO_3$ from stock solutions of 1000 mg/L zinc, strontium, silicon, germanium, zirconium, sodium, and calcium analytical standards (Perkin Elmer Atomic Spectroscopy Standards). Inductively coupled plasma optical emission spectroscopy (ICP-OES) was applied using a Perkin Elmer Optima 8000 optical emission spectrometer equipped with WinLab32 ICP software. Diluted extract concentrations were determined against empirical calibration curves for the following ions, listed along with their respective emission wavelengths: Zn (206.200 nm), Sr (407.771 nm), Si (251.611 nm), Ge (209.426 nm), Zr (343.823 nm), Na (589.592 nm) and Ca (317.933 nm). FIGS. 33A-D provide degradation data for Zn, Ge, Zr and Sr, respectively after 1, 7 and 30 days for cement extracts. FIGS. 34A-C provide degradation data for Ge, Sr and Zn respectively after 1, 7 and 30 days for glass extracts.

Assessment of Cell Cytotoxicity (LDH Assay).

Cell cytotoxicity can also be assessed in an LDH assay. The lactate dehydrogenase (LDH) assay is measured by a colorimetric lactate dehydrogenase (LDH) assay (TOX-7 (Product Code: 050M6079), Sigma Aldrich, Canada), according to recommendations from the supplier. The amount of LDH in the medium is proportional to the number of lysed/dead cells present; therefore, this assay can be used to estimate cell death. This assay measures membrane integrity as a function of the amount of cytoplasmic LDH released into the medium. Briefly, assay mixture is prepared by mixing equal amounts of LDH assay substrate (Catalog Number: L2402), cofactor (Catalog Number: L2527) and dye solutions (Catalog Number: L2277). For all cultures (70 µL), assay mixture is added to the medium in a proportion of two to one in 4×96-nontissue culture-treated polystyrene plates (CoStar, Corning, Canada). Each plate corresponds to medium dilutions of 25, 50, 75 and 100%, respectively. Samples are incubated at room temperature in the dark (each plate covered with Al foil) and through gentle rotation on a roller, the color reaction is stopped by 1 N HCl. Similar to the MTT assay, DMEM+5% FCS culture media plus sterile tissue culture water is used as a negative control and culture media plus cells plus sterile tissue culture water is used as a positive control. Absorbance is determined at 490 nm using a multidetection microplate reader (Synergy HT, BIO-TEK), with the background correction performed at 650 nm.

Statistical Analysis.

Each experiment is performed in triplicate and analysed using Prism 5.0 software (GraphPad software, Inc.) Results are expressed as mean±standard deviation of the triplicate determinations. One way analysis of variance (ANOVA) was carried out followed by a Tukey's post hoc test for comparisons between groups. The level of significance was set at $p<0.05$.

Example 13

Optimizing Cements for Minimum and Maximum Germanium Release

As shown above, zinc, zirconium and strontium are released at very low concentrations over all time periods. Germanium is released at higher amounts and thus having a composition optimized for both minimum and maximum release of germanium is useful. The responses were modeled using Scheffé's equations quadratically (working time and [$Ge^{4+}$]) as well as cubically (setting time). The general forms of the polynomials are shown below:

$$Output_Q = \sum_{i=1}^{q} \beta_i \chi_i + \sum_{i=1}^{q-1} \sum_{j=i+1}^{q} \beta_{ij} \chi_i \chi_j + e$$

wherein $\chi_i$ correspond to $i^{th}$ compositional factors, q=4, $\beta_i$ correspond to the effects of individual $\chi_i$, $\beta_{i,j}$ represent the effect of two-way interactions between $\chi_i$ and e is the residual.

$$Output_c = \sum_{i=1}^{q} \beta_i \chi_i + \sum_{i=1}^{q-1} \sum_{j=i+1}^{q} \beta_{ij} \chi_i \chi_j +$$

$$\sum_{i=1}^{q-1} \sum_{j=i+1}^{q} \gamma_{ij} \chi_i \chi_j (\chi_i - \chi_j) + \sum_{i=1}^{q-2} \sum_{j=i+1}^{q-1} \sum_{k=j+1}^{q} \beta_{ijk} \chi_i \chi_j \chi_l + e$$

where $\gamma_{ij}$ represent the coefficients of the cubic blending of binaries $\chi_i\chi_j(\chi_i-\chi_j)$, and $\beta_{ijk}$ represent the coefficients of the cubic blending of ternaries $\chi_i\chi_j\chi_l$. Table 8 provides the optimization criteria for maximizing [$Ge^{4+}$] release. The asterisks denote the importance of each criteria with more asterisks indicating higher importance.

TABLE 8

| Criteria Set | Working time | Setting time | 30 d Extract [GeO$_2$] |
|---|---|---|---|
| 1 | In range: 360-602 seconds ***** | In range: 900-1200 seconds *** | Maximize *** |
| 2 | In range: 360-602 seconds and target: 360 seconds ***** | In range: 900-1200 seconds *** | Maximize *** |
| 3 | In range: 360-602 seconds and target: 360 seconds ***** | In range: 900-1200 seconds and target: 900 seconds *** | Maximize *** |
| 4 | In range: 360-602 seconds and target: 450 seconds ***** | In range: 900-1200 seconds and target: 900 seconds *** | Maximize *** |
| 5 | In range: 360-602 seconds ***** | In range: 900-1200 seconds and target: 900 seconds *** | Maximize *** |

Using the above models and criteria, cements that would optimize release of germanium for each of the above criteria have the following:

| Criteria set | SiO$_2$ | GeO$_2$ | ZrO$_2$/Na$_2$O (combined mole fraction) | CaO | Desirability |
|---|---|---|---|---|---|
| 1 | 0 | 0.480 | 0.001 | 0.119 | 1.00 |
| 2 | 0.012 | 0.468 | 0.017 | 0.103 | 0.974 |
| 3 | 0.057 | 0.381 | 0.047 | 0.115 | 0.863 |
| 4 | 0.130 | 0.350 | 0.029 | 0.091 | 0.809 |
| 5 | 0.021 | 0.459 | 0.019 | 0.101 | 0.948 |

Zinc and strontium are added to each of the above combinations. In one embodiment those additions are 0.36 mole fraction ZnO and 0.04 mole fraction SrO. In some embodiments, the combined mole fraction ZrO$_2$/Na$_2$O is achieved by providing equal mole fractions of each of ZrO$_2$ and Na$_2$O.

When criteria 5 from Table 8 is used and the germanium release is instead to be minimized, an optimal glass has the composition:

| Criteria set | SiO$_2$ | GeO$_2$ | ZrO$_2$/Na$_2$O (combined mole fraction) | CaO | Desirability |
|---|---|---|---|---|---|
| 5 (but minimizing [Ge$^{4+}$]) | 0.318 | 0.162 | 0.032 | 0.088 | 0.914 |

Here also, zinc and strontium are added and in one embodiment it is in the amounts of 0.36 mole fraction ZnO$_2$ and 0.04 mole fraction SrO$_2$. In some embodiments, the combined mole fraction ZrO$_2$/Na$_2$O is achieved by providing equal mole fractions of each of ZrO$_2$ and Na$_2$O.

Example 14

Cadaveric Study

A maximum of twenty cadaveric thoracic vertebrae are disarticulated, cleaned of soft tissue and separated into four different groups. If the size or shapes of the posterior elements of the vertebrae prevent the loading of the specimens into the compression test fixture, than the posterior elements are removed, as others have done in the literature. Anterior, posterior, left and right lateral heights are recorded and averaged for each specimen. Impressions are made of the superior and inferior surfaces of each vertebra using a semi-cured molding material, to ensure even distribution of compressive load. Specimens will be incubated in 37° C. water for 24 hours. Specimens are loaded into the Instron 3344 mechanical testing machine with their respective molds. Specimens are compressed at a rate of 0.5 mm/s until a 25% reduction in height is seen. A height loss of 25% is part of the clinical definition of a vertebral body compression fractures. For all specimens, max load and stiffness are recorded. The max load is taken as the peak load during the trial, and stiffness is taken as the slope of the force-displacement curve.

Commercial cements are prepared according to manufacturer's instructions. The cements disclosed herein will be prepared according to Example 5.

Augmentation is conducted on a maximum of 15 fractured specimens, 5 for each cement type. Cement is injected through two 11-gauge bone biopsy needles into the fractured vertebral body. The volume of cement is determined at the time of testing, ensuring the same volume is administered to each specimen. Typical volumes are between 2 and 8 ml. Specimens are incubated in 37° C. water for 24 hours. Specimens are loaded into the Instron 3344 mechanical testing machine with their respective molds. New anterior, posterior, left and right lateral heights are recorded and averaged for each specimen. All specimens are recompressed (even the non-augmented controls, acting as untreated controls) at a rate of 0.5 mm/s until a further 25% reduction in height is seen. A height loss of 25% is part of the clinical definition of a vertebral body compression fractures. Post treatment max load is taken as the peak load during the trial. Stiffness is taken as the gradient of the force-displacement curve prior to failure. The results of the augmented specimens is normalized using the initial strengths and stiffness to determine the percent change in strength and stiffness of the vertebral body post injection. This allows comparison of performance of the novel cements to the commercial controls, limiting the influence of size variation (T2 vs. T12) on the strength and stiffness comparison.

Strength and stiffness of each will be collected from all samples for the initial compression, and compression after augmentation. This data will be collected using an Instron 3344 Single Column Testing System, with Bluehill 2 Materials Testing Software (Instron, Norwood, Mass., USA).

Example 15

Kits

Also provided are kits for preparing bone cement. Kits include glass powders having the disclosed ratios of components and instructions for preparing a cement from the glass powder.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the invention.

REFERENCES

1. Boyd, D., et al., *Zinc-based glass polyalkenoate cements with improved setting times and mechanical properties.* Acta biomaterialia, 2008. 4(2): p. 425-31.
2. Rajmohan, N., P. Frugier, and S. Gin, *Composition effects on synthetic glass alteration mechanisms: Part 1. Experiments.* Chemical Geology, 2010. 279(3,Äì4): p. 106-119.
3. Angeli, F., et al., *Influence of zirconium on the structure of pristine and leached soda-lime borosilicate glasses: Towards a quantitative approach by 17O MQMAS NMR.* Journal of Non-Crystalline Solids, 2008. 354(31): p. 3713-3722.
4. Neve, A. D., V. Piddock, and E. C. Combe, *The effect of glass heat treatment on the properties of a novel polyalkenoate cement.* Clinical Materials, 1993. 12(2): p. 113-115.

5. Boyd, D., et al., *Comparison of an experimental bone cement with surgical Simplex P, Spineplex and Cortoss*. Journal of materials science. Materials in medicine, 2008. 19(4): p. 1745-52.
6. Clarkin, O., D. Boyd, and M. R. Towler, *Strontium-based glass polyalkenoate cements for luting applications in the skeleton*. Journal of biomaterials applications, 2010. 24(6): p. 483-502.
7. Clarkin, O. M., D. Boyd, and M. R. Towler, *Comparison of failure mechanisms for cements used in skeletal luting applications*. Journal of materials science. Materials in medicine, 2009. 20(8): p. 1585-94.
8. ISO9917, Dentistry—Water-based cements, 2007.
9. Williams, J. A., R. W. Billington, and G. J. Pearson, *The effect of the disc support system on biaxial tensile strength of a glass ionomer cement*. Dental Materials, 2002. 18(5): p. 376-379.
10. Higgs, W. A. J., et al., *A simple method of determining the modulus of orthopedic bone cement*. Journal of biomedical materials research, 2001. 58(2): p. 188-195.
11. ISO6872, Dentistry—Ceramic materials, 2008.
12. Tsigkou O, Jones J R, Polak J M, Stevens M M. Differentiation of fetal osteoblasts and formation of mineralized bone nodules by 45S5 Bioglass ® conditioned medium in the absence of osteogenic supplements. Biomaterials. 2009; 30:3542-50.

The invention claimed is:

1. A composition comprising:
    an acid degradable glass powder comprising:
        0.1-0.75 mole fraction $GeO_2$;
            0.11-0.53 mole fraction ZnO; and
        0.02-0.48 mole fraction $SiO_2$;
            wherein the composition comprises no more than 0.01 mole fraction aluminosilicates.
2. The composition of claim 1 further comprising 0.025-0.12 mole fraction SrO.
3. The composition of claim 1 further comprising 0.005-0.08 mole fraction each of $ZrO_2$ and $Na_2O$.
4. The composition of claim 1 comprising 0.1-0.75 mole fraction $GeO_2$ and 0.005-0.04 mole fraction each of $ZrO_2$ and $Na_2O$.
5. The composition of claim 1 comprising 0.1-0.6 mole fraction $GeO_2$.
6. The composition of claim 1 comprising about 0.36 mole fraction ZnO.
7. The composition of claim 1 comprising 0.02-0.25 mole fraction $SiO_2$.
8. The composition of claim 2 comprising about 0.04 mole fraction SrO.
9. The composition of claim 1 comprising 0.01-0.35 mole fraction CaO.
10. The composition of claim 1 comprising 0.005-0.06 mole fraction each of $ZrO_2$ and $Na_2O$.
11. The composition of claim 1 wherein the composition is substantially free of aluminosilicates.
12. The composition according to claim 1:
    wherein the glass powder comprises:
        0.012 mole fraction $SiO_2$, 0.468 mole fraction $GeO_2$, 0.017 combined mole fraction $ZrO_2/Na_2O$, and 0.103 mole fraction CaO; or
        0.057 mole fraction $SiO_2$, 0.381 mole fraction $GeO_2$, 0.047 combined mole fraction $ZrO_2/Na_2O$, and 0.115 mole fraction CaO; or
        0.130 mole fraction $SiO_2$, 0.350 mole fraction $GeO_2$, 0.029 combined mole fraction $ZrO_2/Na_2O$, and 0.091 mole fraction CaO; or
        0.021 mole fraction $SiO_2$, 0.459 mole fraction $GeO_2$, 0.019 combined mole fraction $ZrO_2/Na_2O$, and 0.101 mole fraction CaO; or
        0.318 mole fraction $SiO_2$, 0.162 mole fraction $GeO_2$, 0.032 combined mole fraction $ZrO_2/Na_2O$, and 0.088 mole fraction CaO;
    wherein the glass powder further comprises zinc and strontium components.
13. The composition according to claim 12, wherein the zinc and strontium components comprise 0.36 mole fraction ZnO and 0.04 mole fraction SrO.
14. The composition according to claim 12, wherein the combined mole fraction $ZrO_2/Na_2O$ is equal mole fractions of $ZrO_2$ and $Na_2O$.
15. The composition according to claim 1 wherein the glass powder comprises:
    0.215 mole fraction $SiO_2$, 0.215 mole fraction $GeO_2$, 0.050 combined mole fraction $ZrO_2/Na_2O$, and 0.120 mole fraction CaO;
    wherein the glass powder further comprises zinc and strontium components.
16. The composition according to claim 15, wherein the zinc and strontium components comprise 0.36 mole fraction ZnO and 0.04 mole fraction SrO.
17. The composition according to claim 15, wherein the combined mole fraction $ZrO_2/Na_2O$ is equal mole fractions of $ZrO_2$ and $Na_2O$.
18. A composition according to claim 1 in combination with an aqueous solution of about 40%-60% by weight polyalkenoic acid wherein the composition and aqueous solution are in a ratio of about 2:1 to 1:1, for use as a bone cement,
    wherein the polyalkenoic acid has a weight average molecular weight (Mw) of about 1,150 to 1,500,000.
19. The composition of claim 1 comprising 0.2-0.5 mole fraction $GeO_2$.
20. The composition of claim 1 comprising 0.35-0.50 mole fraction $GeO_2$.
21. The composition of claim 1 comprising 0.02-0.2 mole fraction $SiO_2$.
22. The composition of claim 1 comprising 0.02-0.16 mole fraction CaO.
23. The composition of claim 1 comprising 0.02-0.12 mole fraction CaO.
24. The composition of claim 1 comprising 0.05-0.15 mole fraction CaO.
25. The composition of claim 1 comprising 0.07-0.13 mole fraction CaO.
26. The composition of claim 1 comprising 0.01-0.055 mole fraction each of $ZrO_2$ and $Na_2O$.
27. The composition of claim 1 comprising 0.02-0.04 mole fraction each of $ZrO_2$ and $Na_2O$.
28. The composition of claim 18 wherein the polyalkenoic acid has a weight average molecular weight (Mw) of about 1,150 to 383,000.
29. The composition of claim 18 wherein the polyalkenoic acid has a weight average molecular weight (Mw) of about 1,150 to 114,000.
30. The composition of claim 18 wherein the polyalkenoic acid has a weight average molecular weight (Mw) of about 1,150 to 22,700.

\* \* \* \* \*